United States Patent
Bachmann et al.

(10) Patent No.: US 10,696,996 B2
(45) Date of Patent: Jun. 30, 2020

(54) **BIOSYNTHESIS OF EVERNINOMICIN ANALOGS IN *MICROMONOSPORA CARBONACEA* VAR *

(56) References Cited

OTHER PUBLICATIONS

Arenz, et la., "Structures of the orthosomycin antibiotics avilamycin and evernimicin in complex with the bacterial 70S ribosome", Wilson group Proc. Natl. Acad. Sci. USA 2016, 113:7527.
Baizman, et al. "Antibacterial activity of synthetic analogues based on the disaccharide structure of moenomycin, an inhibitor of bacterial transglycosylase." Microbiology 146, 12, 3129-3140 (2000).
Balthaser, et al., "Bronsted acid-promoted glycosylations of disaccharide glycal substructures of the saccharomicins." Org Lett 11, 4850-4853 (2009).
Bartner, et al. "Structure elucidation of Everninomicin-6, a new oligosaccharide antibiotic, by chemical degradation and FAB-MS methods." J Am Soc Mass Spectrom 8, 1134-1140 (1997).
Bauer, et al., "Formation of both methylenedioxy groups in the alkaloid (S)-stylopine is catalyzed by cytochrom P450 enzymes." Tetrahedron Lett 30, 5257-5260 (1989).
Beau, et al., "Synthesis of the disaccharide C-D fragment found in everninomicin-C and -D, avalamycin-A and -C and curamycin-A: stereochemistry at the spiro-ortholactone center." Tetrahedron Lett 28, 1105-1108 (1987).
Belova, et al., "A novel site of antibiotic action in the ribosome: interaction of evernimicin with the large ribosomal subunit." Proc Nat Acad Sci USA 98, 3726-3731 (2001).
Berner, et al. "Genes and enzymes involved in caffeic acid biosynthesis in the actinomycete Saccharothrix espanaensis." J Bacteriol 188, 2666-2673 (2006).
Bierman, et al. "Plasmid Cloning Vectors for the Conjugal Transfer of DNA from *Escherichia coli* to *Streptomyces* Spp." Gene 116, 43-49 (1992).
Boal, et al., "Assembly of the unusual oxacycles in the orthosomycin antibiotics." Proc Nat Acad Sci USA 112, 11989-11990 (2015).
Boll, R. et al. "The active conformation of avilamycin A is conferred by AviX12, a radical AdoMet enzyme." J Biol Chem 281, 14756-14763 (2006).
Borowski, et al., "Mechanism for cyclization reaction by clavaminic acid synthase." Insights from modeling studies. Biochemistry 46, 3682-3691 (2007).
Boucher, et al., "In vivo activity of evernimicin (SCH 27899) against methicillin-resistant *Staphylococcus aureus* in experimental infective endocarditis." Antimicrob Agents Chemother 45, 208-211 (2001).
Butaye, et al., "Antimicrobial growth promoters used in animal feed: effects of less well-known antibiotics on gram-positive bacteria." Clin Microbiol Rev 16, 175-188 (2003).
Butaye, et al., "Differences in antibiotic resistance patterns of Enterococcus faecalis and Enterococcus faecium strains isolated from farm and pet animals." Antimicrob Agents Chemother 45, 1374-1378 (2001).
Butler, et al., "Antibiotics in the clinical pipeline in 2013." J Antibiot 66, 571-591 (2013).
Champney, "Evernimicin (SCH27899) Inhibits both Translation and 50S Ribosomal Subunit Formation in *Staphylococcus aureus* Cells." Antimicrob Agents Chemother 44, 1413-1417 (2000).
Chen, et al., "Multiple-Stage Mass Spectrometric Analysis of Complex Oligosaccharide Antibiotics (Everninomicins) in a Quadrupole Ion Trap." J Am Soc Mass Spectrom 13, 1313-1321 (2002).
Chen, L. et al. "Vancomycin analogues active against vanA-resistant strains inhibit bacterial transglycosylase without binding substrate." Proc Nat Acad Sci USA 100, 5658-5663 (2003).
Cheng, T. J. et al. "Domain requirement of moenomycin binding to bifunctional transglycosylases and development of high-throughput discovery of antibiotics." Proc Nat Acad Sci USA 105, 431-436 (2008).
Cheng, T. J. et al. "High-throughput identification of antibacterials against methicillin-resistant *Staphylococcus aureus* (MRSA) and the transglycosylase." Bioorg Med Chem 18, 8512-8529 (2010).
Chu, M. et al. "Isolation and Characterization of Novel Oligosaccharides Related to Ziracin." J Nat Prod 65, 1588-1593 (2002).
Chu, et al., "A novel everninomicin antibiotic active against multidrug-resistant bacteria." Tetrahedron Lett 41, 6689-6693 (2000).
CLSI. Methods for Dilution Antimicrobial Susceptibility Tests for Bacteria that Grow Aerobically; Approved Standard—Ninth Edition., vol. CLSI document M07-A9 (Clinical and Laboratory Standards Institute, 2012).
Cormican, et al., "Preliminary interpretive criteria for disk diffusion susceptibility testing of SCH 27899, a compound in the everninomicin class of antimicrobial agents." Diag Microbiol Inf Dis 23, 157-160 (1995).
Degwert, et al. "Studies on the biosynthesis of the alpha-glucosidase inhibitor acarbose: valienamine, a m-C7N unit not derived from the shikimate pathway." J Antibiot 40, 855-861 (1987).
Dever, et al., "In vitro activities of the everninomicin SCH 27899 and other newer antimicrobial agents against Borrelia burgdorferi." Antimicrob Agents Chemother 43, 1773-1775 (1999).
Diaz, et al. "Characterization of two methylenedioxy bridge-forming cytochrome P450-dependent enzymes of alkaloid formation in the Mexican prickly poppy Argemone mexicana." Arch Biochem Biophys 507, 186-193 (2011).
Duncan, et al., "Molecular networking and pattern-based genome mining improves discovery of biosynthetic gene clusters and their products from *Salinispora* species." Chem Biol 22, 460-471 (2015).
Eggert, et al. "Genetic basis for activity differences between vancomycin and glycolipid derivatives of vancomycin." Science 294, 361-364 (2001).
Eichhorn, et al., "Characterization of moenomycin antibiotics from medicated chicken feed by ion-trap mass spectrometry with electrospray ionization." Rap Comm Mass Spectrom 19 (2005).
Eichhorn, et al., "Fragmentation studies on the antibiotic avilamycin A using ion trap mass spectrometry." J Mass Spectrom 39, 1541-1553 (2004).
Farnet, et al. Genes and proteins for the biosynthesis of rosaramicin, Google Patents (2003).
Fehlhaber, et al. "Moenomycin-a—a Structural Revision and New Structure-Activity Relations." Tetrahedron 46, 1557-1568 (1990).
Fischbach, et al., "Antibiotics for emerging pathogens." Science 325, 1089-1093 (2009).
Flatt, et al., "Biosynthesis of aminocyclitol-aminoglycoside antibiotics and related compounds." Nat Prod Rep 24, 358-392 (2007).
Foster, et al., "Pharmacologic and bacteriologic properties of SCH-27899 (Ziracin), an investigational antibiotic from the everninomicin family." Pharmacotherapy 19, 1111-1117 (1999).
Funaishi, K. et al. "New analogues of rosaramicin isolated from a Micromonospora strain. I. Taxonomy, fermentation, isolation and physico-chemical and biological properties." J Antibiot 43, 938-947 (1990).
Fuse, S. et al. "Functional and structural analysis of a key region of the cell wall inhibitor moenomycin." ACS Chem Biol 5, 701-711 (2010).
Gaisser, S. et al. "Analysis of eryBI, eryBIII and eryBVII from the erythromycin biosynthetic gene cluster in Saccharopolyspora erythraea." Mol Gen Genet 258, 78-88 (1998).
Gaisser, et al., "Cloning of an avilamycin biosynthetic gene cluster from Streptomyces viridochromogenes Tu57." J Bacteriol 179, 6271-6278 (1997).
Gampe, et al, "Tuning the Moenomycin Pharmacophore to Enable Discovery of Bacterial Cell Wall Synthesis Inhibitors." J Am Chem Soc 135, 3776-3779 (2013).
Gampe, et al., "Modular synthesis of diphospholipid oligosaccharide fragments of the bacterial cell wall and their use to study the mechanism of moenomycin and other antibiotics." Tetrahedron 67, 9771-9778 (2011).
Ganguly, et al., Communications to the editor: structure of everninomicin B. J Antibiot 28, 707-709 (1975).
Ganguly, et al., "Letter: Structure of everninomicin C." J Antibiot 28, 710-712 (1975).
Ganguly, et al. "Electrochemical modification of everninomicin D." J Chem Soc Chem Comm 56-58 (1980).
Ganguly, A. K. et al. "Negative ion multiple-stage mass spectrometric analysis of complex oligosaccharides (everninomicins) in a quadrupole ion trap: Implications for charge-remote fragmentation." Arkivoc, 31-44 (2003).

(56) References Cited

OTHER PUBLICATIONS

Ganguly, A. K. et al. "The Structure of New Oligosaccharide." Antibiotics, 13-384 Component-1 and Component-5. Heterocycles 28, 83-88 (1989).
Ganguly, A. K., et al., "Ziracin, a novel oligosaccharide antibiotic." J Antibiot 53, 1038-1044 (2000).
Ganguly, A. K., et al, "Determination of the absolute stereochemistry at the C16 orthoester of everninomicin antibiotics; a novel acid-catalyzed isomerization of orthoesters." Tetrahedron Lett 38, 7989-7992, (1997).
Ganguly, A. K., et al, "Chemical Modifications and Structure Activity Studies of Ziracin and Related Everninomicin Antibiotics." Bioorg Med Chem Lett 9, 1209-1214 (1999).
Ganguly, A. K., et al., "Structure of Everninomicin D1." J Am Chem Soc 97, 1982-1985 (1975).
Ganguly, A. K., et al., "Structure of everninomicin-2." J Chem Soc Chem Comm 609-611 (1976).
Gavrish, et al., "A trap for in situ cultivation of filamentous actinobacteria." J Microbiol Meth 72, 257-262 (2008).
Geng, et al., "Two novel aminooligosaccharides isolated from the culture of Streptomyces coelicoflavus ZG0656 as potent inhibitors of alpha-amylase." Carb Res 343, 470-476 (2008).
Geng, et al. "Taxonomy of the Streptomyces strain ZG0656 that produces acarviostatin alpha-amylase inhibitors and analysis of their effects on blood glucose levels in mammalian systems." J Appl Microbiol 106, 525-533 (2009).
Geng, et al., "Profiling of acarviostatin family secondary metabolites secreted by Streptomyces coelicoflavus ZG0656 using ultraperformance liquid chromatography coupled with electrospray ionization mass spectrometry." Anal Chem 80, 7554-7561 (2008).
Geng, et al., "Four acarviosin-containing oligosaccharides identified from Streptomyces coelicoflavus ZG0656 are potent inhibitors of alpha-amylase." Carb Res 343, 882-892 (2008).
Goldman, et al., Inhibition of transglycosylation involved in bacterial peptidoglycan synthesis. Curr Med Chem 7, 801-820 (2000).
Goldman, et al., "Differential antibacterial activity of moenomycin analogues on gram-positive bacteria." Bioorg Med Chem Lett 10, 2251-2254 (2000).
Griffith, et al., "Model for Antibiotic Optimization via Neoglycosylation: Synthesis of Liponeoglycopeptides Active against VRE." J Am Chem Soc 129, 8150-8155 (2007).
Guo, X. et al., "Draft genome sequence of Streptomyces coelicoflavus ZG0656 reveals the putative biosynthetic gene cluster of acarviostatin family alpha-amylase inhibitors." Lett Appl Microbiol 55, 162-169 (2012).
Gust, B. et al., "Lambda red-mediated genetic manipulation of antibiotic-producing Streptomyces." Adv Appl Microbiol 54, 107-128 (2004).
Gust, B., et al., PCR-targeted Streptomyces gene replacement identifies a protein domain needed for biosynthesis of the sesquiterpene soil odor geosmin. Proc Nat Acad Sci USA 100, 1541-1546 (2003).
Hansen, J. L. et al. "The Structures of Four Macrolide Antibiotics Bound to the Large Ribosomal Subunit." Mol Cell 10, 117-128 (2002).
He, H, et al., "Isolation and structural elucidation of AC326-alpha, a new member of the moenomycin group." J Antibiot 53, 191-195 (2000).
Heaslet, et la, "Characterization of the active site of S. aureus monofunctional glycosyltransferase (Mtg) by site-directed mutation and structural analysis of the protein complexed with moenomycin." J Struct Biol 167, 129-135 (2009).
Hegg, et al., "The 2-His-l-carboxylate facial triad—an emerging structural motif in mononuclear non-heme iron(II) enzymes." Eur J Biochem FEBS 250, 625-629 (1997).
Hemker, M. et al. "Identification, cloning, expression, and characterization of the extracellular acarbose-modifying glycosyltransferase, AcbD, from Actinoplanes sp. strain SE50." J Bacteriol 183, 4484-4492 (2001).
Herzog, et al., "Chemistry of Antibiotics from Micromonospora. 3. Isolation and Characterization of Everninomicin D and B." Appl Microbiol 13, 515-520 (1965).
Hofmann, C. et al. "Genes encoding enzymes responsible for biosynthesis of L-lyxose and attachment of eurekanate during avilamycin biosynthesis." Chem Biol 12, 1137-1143 (2005).
Hosted, et al., "Characterization of the biosynthetic gene cluster for the oligosaccharide antibiotic, Evernimicin, in *Micromonospora carbonacea* var. *africana* ATCC39149." J Ind Microbiol Biotechnol 27, 386-392 (2001).
Hu, et al., "A unifying nitrososynthase involved in nitrosugar biosynthesis." J Am Chem Soc 130, 15756-15757 (2008).
Huang, et al. "Crystal structure of *Staphylococcus aureus* transglycosylase in complex with a lipid II analog and elucidation of peptidoglycan synthesis mechanism." Proc Nat Acad Sci USA 109, 6496-6501 (2012).
Huber, et al, "Moenomycin, an inhibitor of cell wall synthesis." Biochem Biophys Res Comm 30, 7-13 (1968).
Huong, N. L. et al. "Biotransformation of rosamicin antibiotic into 10,11-dihydrorosamicin with enhanced in vitro antibacterial activity against MRSA." J Microbiol Biotechnol 24, 44-47 (2014).
Iizaka, Y. et al. "Function of cytochrome P450 enzymes RosC and RosD in the biosynthesis of rosamicin macrolide antibiotic produced by Micromonospora rosaria." Antimicrob Agents Chemother 57, 1529-1531 (2013).
Islam, K. et al. "Bioorthogonal profiling of protein methylation using azido derivative of S- adenosyl-L-methionine." J Am Chem Soc 134, 5909-5915 (2012).
Iwata-Reuyl, et al, "β-Secondary Kinetic Isotope Effects in the Clavaminate Synthase-Catalyzed Oxidative Cyclization of Proclavaminic Acid and in Related Azetidinone Model Reactions." J Am Chem Soc 121, 11356-11368 (1999).
Jones, et al, "Effect of various levels of avilamycin on the performance of growing-finishing swine." J Anim Sci 65, 881-885 (1987).
Khare, D. et al. "Conformational switch triggered by alpha-ketoglutarate in a halogenase of curacin A biosynthesis." Proc Nat Acad Sci USA 107, 14099-14104 (2010).
Kong, F. et al. "Saccharomicins, Novel Heptadecaglycoside Antibiotics Effective against Multidrug-Resistant Bacteria." J Am Chem Soc 120, 13301-13311 (1998).
Koyama, et al, "Discovery of nosokophic acid, a predicted intermediate of moenomycins, from nosokomycin-producing *Streptomyces* sp. K04-0144." Bioorg Med Chem Lett 23, 860-863 (2013).
Kren, et al., "Glycosides in medicine: the role of glycosidic residue in biological activity." Curr Med Chem 8, 1303-1328 (2001).
Kudo, et al., "Biosynthetic genes for aminoglycoside antibiotics." J Antibiot (Tokyo) 62, 471-481 (2009).
Langenhan, et al. "Modifying the glycosidic linkage in digitoxin analogs provides selective cytotoxins." Bioorg Med Chem Lett 18, 670-673 (2008).
Langenhan, et al, "Enhancing the anticancer properties of cardiac glycosides by neoglycorandomization." Proc Nat Acad Sci USA 102, 12305-12310 (2005).
Lin, C. C. et al. Pharmacokinetics and metabolism of rosaramicin in humans. Antimicrob Agents Chemother 26, 522-526 (1984).
Lovering, et al, "Structural insight into the transglycosylation step of bacterial cell-wall biosynthesis." Science 315, 1402-1405 (2007).
Mahmud, T. "The C7N aminocyclitol family of natural products." Nat Prod Rep 20, 137-166 (2003).
Mahmud, T., et al., "Biosynthesis of unusual aminocyclitol-containing natural products." J Nat Prod 70, 1384-1391 (2007).
Makitrynskyy, R. et al. Genetic factors that influence moenomycin production in streptomycetes. J Ind Microbiol Biotechnol 37, 559-566 (2010).
Mann, et al., "EmtA, a rRNA methyltransferase conferring high-level evernimicin resistance." Mol Microbiol 41, 1349-1356 (2001).
Mann, et al., "The isolation of a second antibiotic from Streptomyces hygroscopicus." J Am Chem Soc 80, 2714-2716 (1958).
Marshall, et al., "Antimicrobial activity of SCH27899 (Ziracin), a novel everninomicin derivative, tested against *Streptococcus*spp.: disk diffusion/etest method evaluations and quality control guidelines." The Quality Control Study Group. Diag Microbiol Inf Dis 33, 19-25 (1999).

(56) References Cited

OTHER PUBLICATIONS

Mazodier, et al., "Intergeneric Conjugation between *Escherichia coli* and *Streptomyces* Species." J Bacteriol 171, 3583-3585 (1989).
McCranie, et al., "Bioactive oligosaccharide natural products." Nat Prod Rep 31, 1026-1042 (2014).
McCulloch, et al., "Oxidative cyclizations in orthosomycin biosynthesis expand the known chemistry of an oxygenase superfamily." Proc Nat Acad Sci USA 112, 11547-11552 (2015).
McDonough, et al. "Structure of human phytanoyl-CoA 2-hydroxylase identifies molecular mechanisms of Refsum disease." J Biol Chem 280, 41101-41110 (2005).
McNicholas, et al., "Effects of mutations in ribosomal protein L16 on susceptibility and accumulation of evernimicin." Antimicrob Agents Chemother 45, 79-83 (2001).
McNicholas, et al., "Evernimicin Binds Exclusively to the 50S Ribosomal Subunit and Inhibits Translation in Cell-Free Systems Derived from both Gram-Positive and Gram-Negative Bacteria." Antimicrob Agents Chemother 44, 1121-1126 (2000).
Mertz, et al., "Isolation and Structural Identification of Nine Avilamycins." J Antibiot Tokyo 39(7), 877-887 (1986).
Mikolajka, et al., "Differential effects of thiopeptide and orthosomycin antibiotics on translational GTPases." Chem Biol 18, 589-600 (2011).
Moremen, et al., "Vertebrate protein glycosylation: diversity, synthesis and function." Nat Rev Mol Cell Biol 13, 448-462 (2012).
Mosbacher, et al., "Crystal structure of the avilamycin resistance-conferring methyltransferase AviRa from *Streptomyces viridochromogenes*." J Mol Biol 329, 147-157 (2003).
Nakajima, et al., "New analogs of rosaramicin isolated from a Micromonospora strain. II. Structure determination." J Antibiot 43, 1006-1009 (1990).
Nakashio, et al., "Everninomicin, a new oligosaccharide antibiotic: its antimicrobial activity, post-antibiotic effect and synergistic bactericidal activity." Drugs Under Experimental & Clinical Research 21, 7-16 (1995).
Newman, D. J. & Cragg, G. M. "Natural products as sources of new drugs over the 30 years from 1981 to 2010." J Nat Prod 75, 311-335 (2012).
Nicolaou, K. C. et al. "Total Synthesis of Everninomicin 13,384-1-Part 1: Synthesis of the A(1)B(A)C Fragment." Angew Chem Int Ed Engl 38, 3334-3339 (1999).
Nicolaou, K. C., et al. "Total Synthesis of Everninomicin 13,384-1—Part 2: Synthesis of the FGHA(2) Fragment." Angew Chem Int Ed Engl 38(22): 3340-334 (1999).
Nicolaou, K. C. et al. "Total synthesis of everninomicin 13,384-1—Part 3: synthesis of the DE fragment and completion of the total synthesis." Chemistry 6, 3149-3165 (2000).
Nicolaou, K. C. et al. "Total synthesis of everninomicin 13,384-1—Part 4: explorations of methodology; stereocontrolled synthesis of 1,1'-disaccharides, 1,2-seleno migrations in carbohydrates, and solution- and solid-phase synthesis of 2-deoxy glycosides and orthoesters." Chemistry 6, 3166-3185 (2000).
Ostash, B. et al., "Moenomycin family antibiotics: chemical synthesis, biosynthesis, and biological activity." Nat Prod Rep 27, 1594-1617 (2010).
Ostash, B. et al., "Complete characterization of the seventeen step moenomycin biosynthetic pathway." Biochemistry 48, 8830-8841 (2009).
Ostash, B., et al., "ABC transporter genes from Streptomyces ghanaensis moenomycin biosynthetic gene cluster: roles in antibiotic production and export." Arch Microbiol 194, 915-922 (2012).
Ostash, B., et al., "A streamlined metabolic pathway for the biosynthesis of moenomycin a." Chem Biol 14, 257-267 (2007).
Palaniappan, N. et al. "Biosynthesis of the aminocyclitol subunit of hygromycin A in Streptomyces hygroscopicus NRRL 2388." Chem Biol 16, 1180-1189 (2009).
Pfaller, M. A. "Flavophospholipol use in animals: positive implications for antimicrobial resistance based on its microbiologic properties." Diag Microbiol Infect Dis 56, 115-121 (2006).
Pletcher, et al., "Synthesis of the saccharomicin fucose-aglycon conjugate and determination of absolute configuration." Org Lett 7, 4749-4752 (2005).
Price, et al., "Evidence for hydrogen abstraction from C1 of taurine by the high-spin Fe(IV) intermediate detected during oxygen activation by taurine:alpha-ketoglutarate dioxygenase (TauD)." J Am Chem Soc 125, 13008-13009 (2003).
Price, et al., "The first direct characterization of a high-valent iron intermediate in the reaction of an alpha-ketoglutarate-dependent dioxygenase: a high-spin FeIV complex in taurine/alpha-ketoglutarate dioxygenase (TauD) from *Escherichia coli*." Biochemistry 42, 7497-7508 (2003).
Proshlyakov, et al., "Direct detection of oxygen intermediates in the non-heme Fe enzyme taurine/alpha-ketoglutarate dioxygenase." J Am Chem Soc 126, 1022-1023 (2004).
Qin, X. et al. "Structures of human pancreatic alpha-amylase in complex with acarviostatins: Implications for drug design against type II diabetes." J Struct Biol 174, 196-202 (2011).
Rabyk, et al., "Streptomyces ghanaensis pleiotropic regulatory gene wblA(gh) influences morphogenesis and moenomycin production." Biotechnol Lett 33, 2481-2486 (2011).
Rebets, et al., "Production of avilamycin A is regulated by AviC1 and AviC2, two transcriptional activators." J Antiobiot 62, 461-464 (2009).
Ren, F. et al. "Insights into the Mechanism of the Antibiotic-Synthesizing Enzyme MoeO5 from Crystal Structures of Different Complexes." Ang Chem Int Ed Engl 51, 17, 4157-4160 (2012).
Reuter, K. et al. "Synthesis of 5-hydroxyectoine from ectoine: crystal structure of the non-heme iron(II) and 2-oxoglutarate-dependent dioxygenase EctD." PloS One 5, e10647, (2010).
Riggs-Gelasco, P. J. et al. "EXAFS spectroscopic evidence for an Fe=O unit in the Fe(IV) intermediate observed during oxygen activation by taurine:alpha-ketoglutarate dioxygenase." J Am Chem Soc 126, 8108-8109 (2004).
Roach, P. L. et al. "Structure of isopenicillin N synthase complexed with substrate and the mechanism of penicillin formation." Nature 387, 827-830 (1997).
Rockser, et al., "The gac-gene cluster for the production of acarbose from Streptomyces glaucescens GLA.O: identification, isolation and characterization." J Biotehchnol 140, 114-123 (2009).
Rudd, et al., "Glycosylation and the immune system." Science 291, 2370-2376 (2001).
Sanders, et al., "Microbiological characterization of everninomicin-B and everninomicin-D." Antimicrob Agents Chemother 6, 232-238 (1974).
Sato, N. et al. "Crystal structures of the reaction intermediate and its homologue of an extradiol-cleaving catecholic dioxygenase." J Mol Biol 321, 621-636 (2002).
Seeberger, et al., "Synthesis and medical applications of oligosaccharides." Nature 446, 1046-1051 (2007).
Shryock, T. R. "Will Avilamycin Convert Ziracine into Zerocine." Emerging Infectious Diseases 7, 488-489 (2001).
Siegrist, S. et al. "Mechanism of action of a 16-membered macrolide: Binding of rosaramicin to the *Escherichia coli* ribosome and its subunits." Eur J Biochem 115(2), 323-327 (1981).
Siegrist, S. et al. "Mechanism of action of a 16-membered macrolide: Characteristics of dihydrorosaramicin binding to *Escherichia coli* ribosome and the effecs of some competitors." J Antibiot (Tokyo) 35(7), 866-874 (1982).
Singh, et al., "The structural biology of enzymes involved in natural product glycosylation." Nat Prod Rep 29, 1201-1237 (2012).
Singh, et al., "Saccharomicins, novel heptadecaglycoside antibiotics produced by Saccharothrix espanaensis: antibacterial and mechanistic activities." Antimicrob Agents Chemother 44, 2154-2159 (2000).
Smith, J et al., "Rosaramicin: in-vitro activity against common bacterial isolates." J Antimicrob Chemother 7, 505-513 (1981).
Souli, et al., "In vivo activities of evernimicin (SCH 27899) against vancomycin-susceptible and vancomycin-resistant enterococci in experimental endocarditis." Antimicob Agents Chemother 44, 2733-2739 (2000).

(56) References Cited

OTHER PUBLICATIONS

Strobel, T. et al. "Complete genome sequence of Saccharothrix espanaensis DSM 44229T and comparison to the other completely sequenced Pseudonocardiaceae." BMC Genomics 13, 465 (2012).
Takahashi, S. et al. "Structure of Pholipomycin." Tetrahedron Lett 24, 499-502 (1983).
Taubes, G. "The Bacteria Fight Back." Science 321, 356-361 (2008).
Taylor, et al., "The total synthesis of moenomycin A." J Am Chem Soc 128, 15084-15085 (2006).
Thibodeaux, et al., "Natural-product sugar biosynthesis and enzymatic glycodiversification." Angew Chem Int Ed Engl. 47, 9814-9859 (2008).
Thibodeaux, et al., "Unusual sugar biosynthesis and natural product glycodiversification." Nature 446, 1008-1016 (2007).
Torikata, A. et al. "Pholipomycin, a new member of phosphoglycolipid antibiotics. III. Biological properties." J Antibiot 30, 1060-1063 (1977).
Treede, I. et al. Genes involved in formation and attachment of a two-carbon chain as a component of eurekanate, a branched-chain sugar moiety of avilamycin A. Appl Environ Microbiol 71, 400-406 (2005).
Treede, I. et al. "The avilamycin resistance determinants AviRa and AviRb methylate 23S rRNA at the guanosine 2535 base and the uridine 2479 ribose." Mol Microbiol 49, 309-318 (2003).
Uchida, R. et al. "Nosokomycins, new antibiotics discovered in an in vivo-mimic infection model using silkworm larvae. I: Fermentation, isolation and biological properties". J Antibiot 63, 151-155 (2010).
Uchida, R., et al., "Nosokomycins, new antibiotics discovered in an in vivo-mimic infection model using silkworm larvae. II: Structure elucidation." J Antibiot 63, 157-163 (2010).
Urban, C. et al., "Comparative in-vitro activity of SCH 27899, a novel everninomicin, and vancomycin." J Antimicrob Chemother 37, 361-364 (1996).
Varki, A. "Biological roles of oligosaccharides: all of the theories are correct." Glycobiology, 3, 97-130 (1997).
Vey, J. L. et al. "Structure and mechanism of ORF36, an amino sugar oxidizing enzyme in everninomicin biosynthesis." Biochemistry 49, 9306-9317 (2010).
Wagman, et al., "Antibiotics from Micromonospora." Ann Rev Microbiol 34, 537-557 (1980).
Waksman, et al., "Micrornonosporin, an Antibiotic Substance from a Little-known Group of Microorganisms." J Bacteriol 53, 355-357 (1947).
Wallhausser, et al., "Moenomycin, a new antibiotic. I. Fermentation and isolation." Antimicrob Agents Chemother (Bethesda) 5, 734-736 (1965).
Wehmeier, et al., "Biotechnology and molecular biology of the alpha-glucosidase inhibitor acarbose." Appl Microbiol Biotechnol 63, 613-625 (2004).
Weinstein, M. J. et al. "Purification and biological studies of everninomicin B." Antimicrob Agents Chemother (Bethesda) 5, 821-827 (1965).
Weinstein, M. J., et al., "Everninomicin, a New Antibiotic Complex from Micromonospora Carbonacea." Antimicrob Agents Chemother (Bethesda) 10, 24-32 (1964).
Weitnauer, et al. "An ATP-Binding Cassette Transporter and Two rRNA Methyltransferases Are Involved in Resistance to Avilamycin in the Producer Organism Streptomyces viridochromogenes Tu57", Antimicrobial Agents and Chemotherapy 2001, 45:690.
Weitnauer, G. et al. "Biosynthesis of the orthosoniycin antibiotic avilamycin A: deductions from the molecular analysis of the avi biosynthetic gene cluster of Streptomyces viridochromogenes Tu57 and production of new antibiotics." Chem Biol 8. 569-581 (2001).
Weitnauer, G., et al., "Analysis of a C-methyltransferase gene (aviG1) involved in avilamycin biosynthesis in Streptomyces viridochromogenes Tu57 and complementation of a Saccharopolyspora erythraea eryBIII mutant by aviG1." Microbiology 148, 373-379 (2002).
Weitnauer, G., et al., "Novel avilamycin derivatives with improved polarity generated by targeted gene disruption." Chem Biol 11, 1403-1411 (2004).
Welsch, M. "Bacteriostatic and Bacteriolytic Properties of Actinomycetes." J Bacteriol 44, 571-588 (1942)
Weymouth-Wilson, A.C. "The role of carbohydrates in biologically active natural products." Nat Prod Rep 14, 99-110 (1997).
Wilson, D. N. "The A-Z of bacterial translation inhibitors." Critic Rev Biochem Mol Biol 44, 393-43 (2009).
Wong, S. D. et al. "Elucidation of the Fe(IV)=O intermediate in the catalytic cycle of the halogenase SyrB2." Nature 499, 320-323 (2013).
Wright, D.E. "The orthosomycins, a new family of antibiotics." Tetrahedron 35, 1207-1237 (1979).
You, Z., et al., "Crystal structure of the non-heme iron dioxygenase Pt1H in pentalenolactone biosynthesis." J Biol Chem 282, 36552-36560 (2007).
Yu, D. et al. "An efficient recombination system for chromosome engineering in *Escherichia coli*." Proc Nat Acad Sci USA 97, 5978-5983 (2000).
Yuan, Y. et al. "Structural analysis of the contacts anchoring moenomycin to peptidoglycan glycosyltransferases and implications for antibiotic design." ACS Chem Biol 3, 429-436 (2008).
Zarazaga, M., et al., "Mutations in Ribosomal Protein L16 and in 23S rRNA in Enterococcus Strains for Which Evernimicin MICs Differ." Antimicrob Agents Chemother 46, 3657-3659 (2002).
Zehl, M., et al., "Characterization of moenomycin antibiotic complex by multistage MALDI-IT/RTOF-MS and ESI-IT-MS." J Am Soc Mass Spectrom 17, 1081- 1090 (2006).
Zhang, C. S., et al., "Natural product diversification using a non-natural cofactor analogue of S-adenosyl-L-methionine." J Am Chem Soc 128, 2760-2761 (2006).
Zhang, Z. et al. "Crystal structure of a clavaminate synthase-Fe(II)-2-oxoglutarate-substrate-NO complex: evidence for metal centered rearrangements." FEBS Lett 517, 7-12 (2002).
Zhang, Z. et al. "Structural origins of the selectivity of the trifunctional oxygenase clavaminic acid synthase." Nat Struct Biol 7, 127-133 (2000).
International Preliminary Report on Patentability issued for International Application No. PCT/US2016/065938, dated Jun. 21, 2018.
Extended Supplemental Search Report issued in EP 16873967.0 dated Jul. 3, 2019.

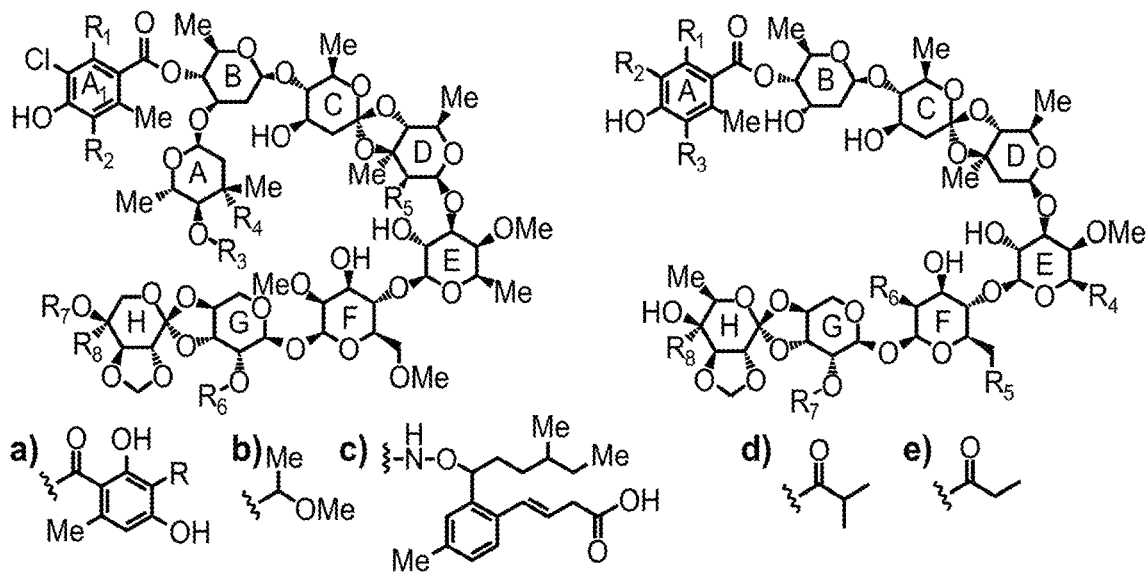

| Everninomicins | $R_1$ | $R_2$ | $R_3$ | $R_4$ | $R_5$ | $R_6$ | $R_7$ | $R_8$ | ( ) |
|---|---|---|---|---|---|---|---|---|---|
| Everninomicin A | OMe | Cl | Me | $NO_2$ | OH | H | a, R=H | H | $CH_2$ |
| Everninomicin B | OMe | Cl | Me | $NO_2$ | OH | Me | H | b | $CH_2$ |
| Everninomicin C | OMe | Cl | Me | $NO_2$ | H | Me | H | H | $CH_2$ |
| Everninomicin D | OMe | Cl | Me | $NO_2$ | H | Me | H | b | $CH_2$ |
| SCH58769 | OH | H | Me | $NO_2$ | OH | H | a, R=H | H | $CH_2$ |
| SCH58771 | OMe | H | Me | $NO_2$ | OH | H | a, R=H | H | $CH_2$ |
| SCH58773 | OMe | Cl | H | $NO_2$ | OH | H | a, R=H | H | $CH_2$ |
| SCH58775 | OMe | Cl | Me | $NO_2$ | OH | H | a, R=H | H | OCOH, H |
| Amino EverA | OMe | Cl | Me | $NH_2$ | OH | H | a, R=H | H | $CH_2$ |
| Ever-2 (No nitrosugar) | OMe | Cl | - | - | H | Me | H | b | $CH_2$ |
| 13-384-1 | OMe | Cl | Me | $NO_2$ | H | Me | a, R=H | H | $CH_2$ |
| 13-384-5 | OMe | Cl | Me | $NH_2$ | H | Me | a, R=H | H | $CH_2$ |
| SCH49088 | OMe | Cl | Me | c | OH | H | a, R=H | H | $CH_2$ |
| SCH58761 | OMe | Cl | Me | $NO_2$ | OH | H | a, R=Cl | H | $CH_2$ |
| Avilamycins | $R_1$ | $R_2$ | $R_3$ | $R_4$ | $R_5$ | $R_6$ | $R_7$ | $R_8$ | |
| Avilamycin A | OMe | Cl | Cl | Me | OMe | OMe | d | COMe | |
| Avilamycin A' | OMe | Cl | Cl | Me | OMe | OMe | e | H | |
| Avilamycin B | OMe | Cl | Cl | Me | OMe | OMe | COMe | COMe | |
| Avilamycin C | OMe | Cl | Cl | Me | OMe | OMe | d | CH(OH)Me | |
| Avilamycin $D_1$ | OMe | Cl | Cl | Me | OMe | OMe | H | COMe | |
| Avilamycin $D_2$ | OMe | Cl | Cl | Me | OMe | OMe | COMe | CH(OH)Me | |
| Avilamycin E | OMe | Cl | Cl | Me | OMe | OMe | H | CH(OH)Me | |
| Avilamycin F | OH | H | Cl | Me | OMe | OMe | d | COMe | |
| Avilamycin G | OMe | Cl | Cl | Me | OMe | OMe | $COC_4H_9$ | COMe | |
| Avilamycin H | OMe | Cl | H | Me | OMe | OMe | d | COMe | |
| Avilamycin I | OMe | Cl | Cl | Me | OMe | OMe | e | COMe | |
| Avilamycin J | OMe | Cl | Cl | Me | OH | OMe | d | COMe | |
| Avilamycin K | OMe | Cl | Cl | $CH_2OH$ | OMe | OMe | d | COMe | |
| Avilamycin L | OMe | Cl | Cl | Me | OMe | OMe | d | CHO | |
| Avilamycin M | OMe | Cl | Cl | H | OMe | OMe | d | COMe | |
| Avilamycin N | OMe | Cl | Cl | Me | OMe | OH | d | COMe | |

FIG. 1

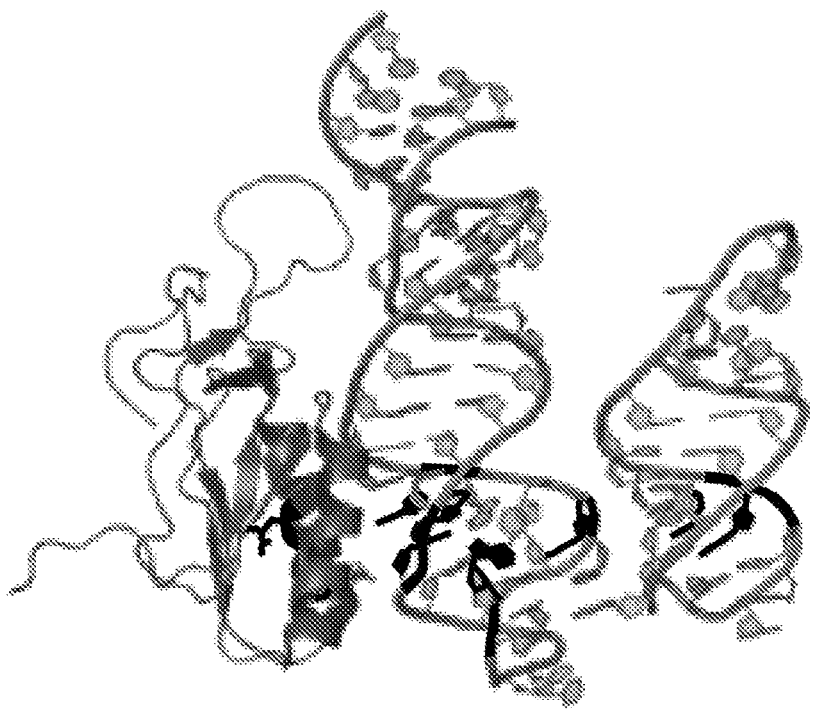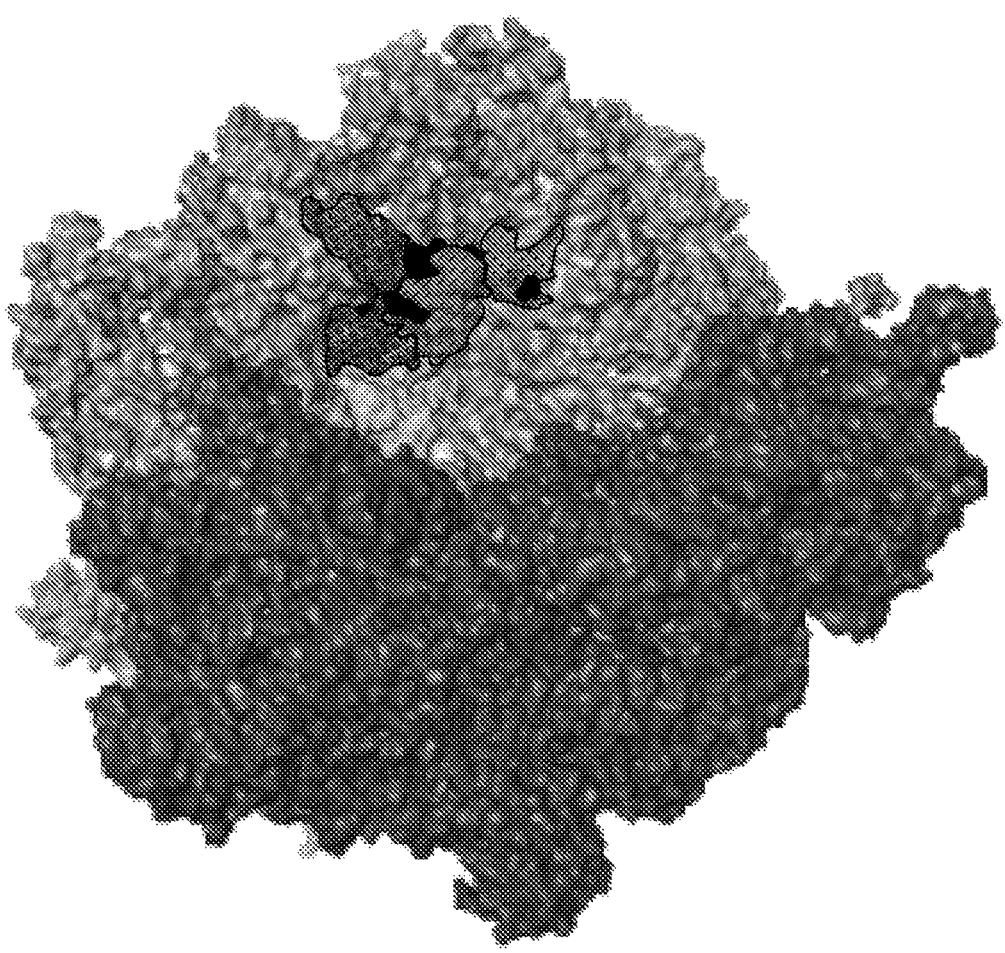
FIG. 2

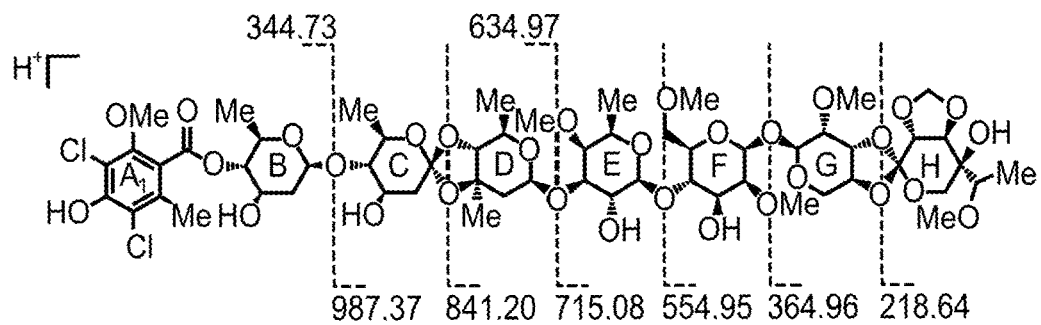
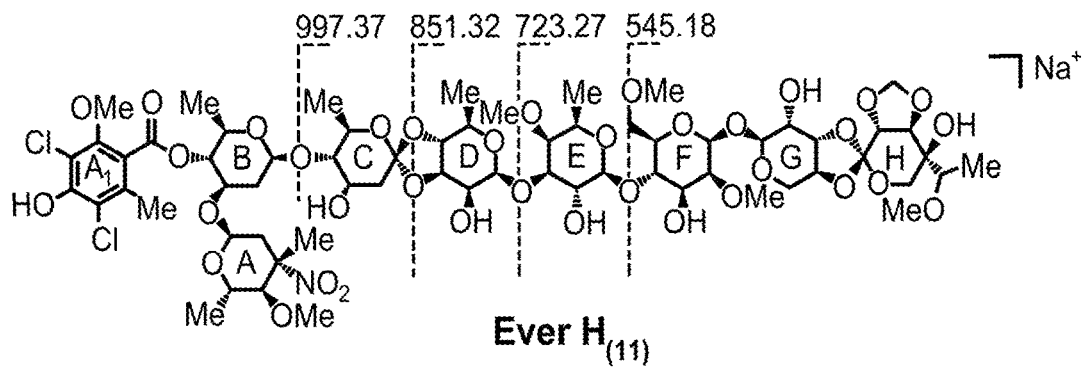
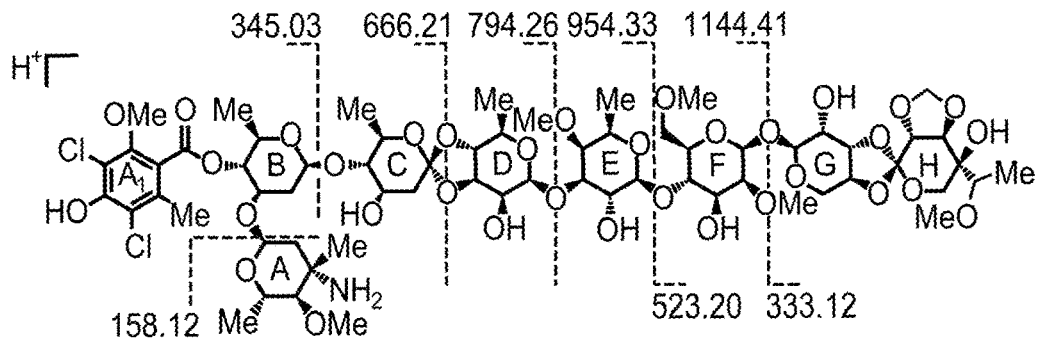
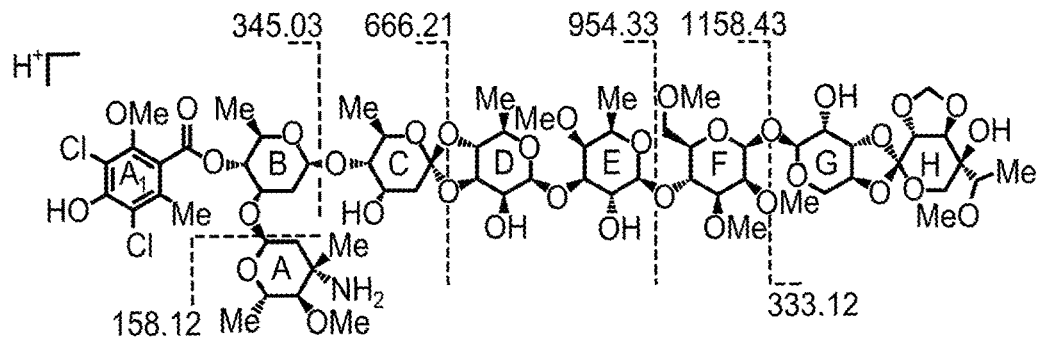
FIG. 3

| GenBank Accession # | Start/Stop (bp) | Gene | Size (aa) | Proposed function | Protein Homolog | Identity (%) | Gen Bank Accession # |
|---|---|---|---|---|---|---|---|
| AX574200 | 753-1 | EvdM1 | 250 | O-methyltransferase | ApoM1 (Nocardiopsis sp. FU40) | 71 | AEP40941 |
| | 1533-2861 | EvdU1 | 442 | Unknown | MCAG_03643 (Micromonospora sp. ATCC 39149) | 76 | ZP_04607386 |
| | 2898-4055 | EvdX1 | 385 | RNA methyltransferase | MCAG_03646 (Micromonospora sp. ATCC 39149) | 70 | ZP_04607389 |
| | 5529-4060 | EvdU2 | 489 | Unknown | MCAG_03647 (Micromonospora sp. ATCC 39149) | 77 | ZP_04607390 |
| | 6174-6998 | EvdM2 | 274 | O-methyltransferase | MCAG_03640 (Micromonospora sp. ATCC 39149) | 79 | ZP_04607383 |
| | 7040-8284 | EvdM3 | 429 | C-methyltransferase | MCAG_03641 (Micromonospora sp. ATCC 39149) | 72 | ZP_04607384 |
| | 8281-9465 | EvdM4 | 423 | O-methyltransferase | StfMIII O-methyltransferase (Streptomyces steffisburgensis) | 100 | CAJ43240 |
| | 9472-10491 | EvdGT1 | 339 | Glycosyltransferase | MCAG_03659 (Micromonospora sp. ATCC 39149) | 57 | ZP_0460742 |
| | 10595-11020 | EvdU3 | 137 | Unknown | AviX10 (Streptomyces viridochromogenes Tue57) | 80 | AAK83174 |
| | 12020-11076 | EvdS1 | 314 | 4-ketoreductase | ApoH3 (Nocardiopsis sp. FU40) | 63 | AEP40908 |
| | 13056-12061 | EvdM5 | 342 | O-methyltransferase | MCAG_03673 (Micromonospora sp. ATCC 39149) | 58 | ZP_04607416 |
| | 13912-13082 | EvdU4 | 276 | Unknown | MCAG_03672 (Micromonospora sp. ATCC 39149) | 69 | ZP_04607415 |
| | 14812-14015 | EvdX2 | 265 | RNA methyltransferase | VAB18032_26045 (Verrucosispora maris) | 57 | YP_004406907 |
| | 15102-16211 | EvdD1 | 344 | Acyltransferase | MCAG_03645 (Micromonospora sp. ATCC 39149) | 75 | ZP_04607388 |
| | 17045-16377 | EvdM6 | 240 | O-methyltransferase | MCAG_03636 (Micromonospora sp. ATCC 39149) | 67 | ZP_04607379 |
| | 18415-17099 | EvdGT2 | 438 | Glycosyltransferase | ApoGT3 (Nocardiopsis sp. FU40) | 76 | AEP40907 |
| | 19900-18683 | EvdS2 | 405 | Epimerase | MCAG_03642 (Micromonospora sp. ATCC 39149) | 74 | ZP_04607385 |
| | 20858-19917 | EvdO1 | 313 | Orthoester synthase | AviO3 (Streptomyces viridochromogenes) | 73 | AAK83187 |
| | 21589-20858 | EvdM7 | 243 | O-methyltransferase | Mtf (Catenuloplanes nepalensis) | 82 | ACL80144 |
| | 23031-21586 | EvdD2 | 481 | Halogenase | MCAG_03648 (Micromonospora sp. ATCC 39149) | 78 | ZP_04607391 |
| | 23372-24487 | EvdGT3 | 380 | Glycosyltransferase | MCAG_03663 (Micromonospora sp. ATCC 39149) | 61 | ZP_04607406 |
| | 24565-25542 | EvdU5 | 325 | Pyruvate dehydrogenase | Dhg (Catenuloplanes nepalensis) | 89 | ACL80142 |
| | 25547-26509 | EvdU6 | 344 | Pyruvate dehydrogenase | AviB2 (Streptomyces viridochromogenes) | 77 | AAK83191 |
| | 26515-27570 | EvdGT4 | 337 | Glycosyltransferase | AviGT3 (Streptomyces viridochromogenes) | 75 | AAK83192 |
| | 27567-28619 | EvdU7 | 350 | Unknown | MCAG_03660 (Micromonospora sp. ATCC 39149) | 64 | ZP_04607403 |
| | 29397-28639 | EvdO2 | 252 | Orthoester synthase | MCAG_03658 (Micromonospora sp. ATCC 39149) | 71 | ZP_04607401 |
| | 29752-30681 | EvdS3 | 309 | Epimerase/dehydratase | UUA_15808 (Rhodanobacter thiooxydans) | 42 | ZP_10205860 |
| | 30879-31946 | EvdS4 | 355 | Glucose-1-phosphate thymidylyltransferase | MCAG_03630 (Micromonospora sp. ATCC 39149) | 79 | ZP_04607373 |
| | 31946-32935 | EvdS5 | 329 | 4,6-dehydratase | MCAG_03631 (Micromonospora sp. ATCC 39149) | 78 | ZP_04607374 |
| | 32990-34018 | EvdS6 | 342 | 4-epimerase | AviQ2 (Streptomyces viridochromogenes) | 82 | AAK83170 |

FIG. 10 continued

| GenBank Accession # | Start/Stop (bp) | Gene | Size (aa) | Proposed function | Protein Homolog | Identity (%) | Gen Bank Accession # |
|---|---|---|---|---|---|---|---|
| | 34073-35425 | EvdOM1 | 450 | Oxidase/methyltransferase | MCAG_03633 (Micromonospora sp. ATCC 39149) | 77 | ZP_04607376 |
| | 39383-35580 | EvdD3 | 1267 | Polyketide synthase | AviM (Streptomyces viridochromogenes) | 65 | AAK83194 |
| | 39773-40612 | EvdU8 | 249 | Unknown | MCAG_03657 (Micromonospora sp. ATCC 39149) | 64 | ZP_04607400 |
| | 40609-41532 | EvdS7 | 307 | 4-ketoreductase | MCAG_03656 (Micromonospora sp. ATCC 39149) | 66 | ZP_04607399 |
| | 42326-41511 | EvdGT5 | 295 | Glycosyltransferase | MCAG_03655 (Micromonospora sp. ATCC 39149) | 80 | ZP_04607398 |
| AX574200 | 42708-42460 | EvdR1 | 82 | Regulator | MCAG_03654 (Micromonospora sp. ATCC 39149) | 82 | ZP_04607397 |
| | 44533-43532 | EvdS8 | 341 | 3-ketoreductase | MCAG_03652 (Micromonospora sp. ATCC 39149) | 68 | ZP_04607395 |
| | 45966-44554 | EvdS9 | 470 | 2,3-dehydratase | MCAG_03651 (Micromonospora sp. ATCC 39149) | 70 | ZP_04607394 |
| | 46910-45963 | EvdS10 | 346 | 4,6-dehydratase | MCAG_03650 (Micromonospora sp. ATCC 39149) | 76 | ZP_04607392 |
| | 47878-47207 | EvdX3 | 254 | RNA Methyltransferase | MCAG_03674 (Micromonospora sp. ATCC 39149) | 71 | ZP_04607417 |
| AX574200/1 | 48183-48070 | EvdS11 | 209 | UDP-glucose 4-epimerase | MCAG_03662 (Micromonospora sp. ATCC 39149) | 74 | ZP_04607405 |
| AX574202 | 1-1203 | EvdN1 | 400 | Nitrososynthase | ORF36 (Micromonospora sp. ATCC 39149) | 80 | ACF94630 |
| | 1200-2327 | EvdS12 | 375 | 3-aminotransferase | MCAG_03665 (Micromonospora sp. ATCC 39149) | 79 | ZP_04607408 |
| | 2357-36-7 | EvdM8 | 416 | C-methyltransferase | MCAG_03666 (Micromonospora sp. ATCC 39149) | 81 | ZP_04607409 |
| | 3616-4239 | EvdS13 | 207 | 3,5-epimerase | MCAG_03667 (Micromonospora sp. ATCC 39149) | 74 | ZP_04607410 |
| | 5169-4060 | EvdS14 | 369 | 4-ketoreductase | StaK (Streptomyces sp. TP-A0274) | 58 | BAC55215 |
| | 6086-5166 | EvdM9 | 306 | O-methyltransferase | MCAG_03669 (Micromonospora sp. ATCC 39149) | 71 | ZP_04607412 |
| | 7811-6261 | EvdU9 | 517 | Unknown | MCAG_00021 (Micromonospora sp. ATCC 39149) | 66 | ZP_04603764 |
| | 8746-7889 | EvdR2 | 286 | Regulator | Amir_6179 (Actinosynnema mirum) | 61 | YP_003103832 |
| | 10035-8764 | EvdR3 | 423 | Regulator | AMED_3740 (Amycolatopsis mediterranei) | 63 | YP_003765921 |

FIG. 10 continued

| GenBank Accession # | Start/Stop (bp) | Gene | Size (#aa) | Proposed function | Protein Homolog | Identity (%) | Gen Bank Accession # |
|---|---|---|---|---|---|---|---|
| AX574198 | 1-747 | EveU1 | 248 | Unknown | AMIS_53450 (Actinoplanes missouriensis) | 58 | YP_005465081 |
|  | 895-1962 | EveS1 | 355 | Glucose-1-phosphate thymidyltransferase | StaA (Streptomyces sp. TP-A0274) | 70 | BAC55207 |
|  | 1962-2951 | EveS2 | 329 | 4,6-dehydratase | AviE1 (Streptomyces viridochromogenes) | 76 | AAK83196 |
|  | 3054-4082 | EveS3 | 342 | 4-epimerase | AviQ2 (Streptomyces viridochromogenes) | 81 | AAK83179 |
|  | 4137-4874 | EveM1 | 245 | Methyltransferase | AviG5 (Streptomyces viridochromogenes) | 59 | AAK83180 |
|  | 4871-5545 | EveO1 | 224 | Oxidase (MDB) | AviO1 (Streptomyces viridochromogenes) | 66 | AAK83181 |
|  | 5598-6869 | EveGT1 | 423 | Glycosyltransferase | AviGT1 (Streptomyces viridochromogenes) | 70 | AAK83182 |
|  | 6946-7689 | EveM2 | 247 | Methyltransferase | AviG2 (Streptomyces viridochromogenes) | 59 | AAK83184 |
|  | 7735-8763 | EveS4 | 342 | Ketoreductase | AviZ1 (Streptomyces viridochromogenes) | 59 | AAK83185 |
|  | 8753-9526 | EveM3 | 257 | Methyltransferase | AviG6 (Streptomyces viridochromogenes) | 74 | AAK83186 |
|  | 9523-10467 | EveO2 | 314 | Orthoester synthase | AviO3 (Streptomyces viridochromogenes) | 75 | AAK83187 |
|  | 10464-11312 | EveM4 | 282 | Methyltransferase | AviG3 (Streptomyces viridochromogenes) | 75 | AAK83188 |
|  | 11314-12594 | EveM5 | 426 | C-methyltransferase | OSCI_3520020 (Oscillatoria sp. PCC 6506) | 50 | ZP_07112622 |
|  | 12627-13820 | EveS5 | 397 | Epimerase | AviX12 (Streptomyces viridochromogenes) | 79 | AAK83189 |
|  | 13867-15204 | EveU3 | 445 | Unknown | Tcp34 (Actinoplanes teichomyceticus) | 57 | CAE53375 |
| AX574199 | 3770-6 | EveD1 | 1254 | Polyketide synthase | AviM (Streptomyces viridochromogenes) | 68 | AAK83194 |
|  | 4893-3859 | EveD2 | 344 | Acyltransferase | AviN (Streptomyces viridochromogenes) | 66 | AAK83178 |
|  | 5247-6308 | EveX1 | 353 | RNA methyltransferase | Kfla_1517 (Kribbella flavida) | 50 | YP_003379414 |
|  | 7815-6313 | EveU4 | 500 | Unknown | Sros_0818 (Streptosporangium roseum) | 56 | YP_003336575 |
|  | 9421-7943 | EveD3 | 492 | Halogenase | Halogenase (Catenuloplanes nepalensis) | 67 | ACL80143 |
|  | 11111-9579 | EveU5 | 510 | Transporter | Putative exporter (Streptomyces auratus) | 53 | ZP_10547180 |
|  | 11767-12615 | EveS6 | 282 | 4,6-dehydratase | PimJ (Streptomyces natalensis) | 67 | CAC20923 |
|  | 12612-14066 | EveS7 | 384 | 2,3-dehydratase | PokS3 (Streptomyces diastatochromogenes) | 53 | ACN64829 |
|  | 14071-15105 | EveS8 | 344 | 3-ketoreductase | SaqT (Micromonospora sp. Tu 6368) | 55 | ACP19378 |
|  | 15140-16075 | EveS9 | 311 | 4-ketoreductase | PokS6 (Streptomyces diastatochromogenes) | 46 | ACN64824 |
|  | 17064-17312 | EveR1 | 82 | Regulator | AviC2 (Streptomyces viridochromogenes) | 68 | AAK83173 |
|  | 17463-18377 | EveGT2 | 304 | Glycosyltransferase | AviGT2 (Streptomyces viridochromogenes) | 72 | AAK83170 |
|  | 19301-18030 | EveS10 | 423 | Epimerase | ChaS4 (Streptomyces chartreusis) | 44 | CAH10166 |
|  | 20061-19309 | EveU6 | 250 | Unknown | SCAB_21471 (Streptomyces scabiei 87.22) | 44 | YP_003487825 |
|  | 20262-21023 | EveO3 | 253 | Orthoester synthase | CfE428DRAFT_0630 (Chthoniobacter flavus) | 48 | ZP_03127466 |
|  | 22144-21122 | EveGT3 | 340 | Glycosyltransferase | AviGT4 (Streptomyces viridochromogenes) | 66 | 2IV3_A |

FIG. 11 continued

| GenBank Accession # | Start/Stop (bp) | Gene | Size (#aa) | Proposed function | Protein Homolog | Identity (%) | Gen Bank Accession # |
|---|---|---|---|---|---|---|---|
| | 23214-22159 | EveU7 | 351 | Unknown | SCAB_21441 (Streptomyces scabiei 87.22) | 51 | YP_003487822 |
| | 24252-23211 | EveGT4 | 347 | Glycosyltransferase | AviGT3 (Streptomyces viridochromogenes) | 72 | AAK83192 |
| | 25189-24251 | EveS11 | 312 | 4-epimerase | AviQ1 (Streptomyces viridochromogenes) | 56 | AAK83169 |
| | 26343-25174 | EveGT5 | 389 | Glycosyltransferase | SaqGT5 (Micromonospora sp. Tu 6368) | 47 | ACP19370 |
| | 26599-27864 | EveN1 | 421 | Nitrososynthase | KijD3 (Actinomadura kijaniata) | 65 | 3M9V_A |
| | 27875-28996 | EveS12 | 373 | 3-aminotransferase | KijD2 (Actinomadura kijaniata) | 75 | ACB46490 |
| | 29105-30355 | EveM6 | 416 | 3-C-methyltransferase | KijD1 (Actinomadura kijaniata) | 71 | ACB46489 |
| | 30363-30965 | EveS13 | 200 | 3,5-epimerase | StaE (Streptomyces sp. TP-A0274) | 64 | BAC55217 |
| | 32002-30923 | EveS14 | 359 | 4-ketoreductase | StaK (Streptomyces sp. TP-A0274) | 58 | BAC55215 |
| | 32933-32004 | EveM7 | 309 | Methyltransferase | DacS7 (Dactylosporangium sp. SC14051) | 64 | AFU65919 |
| | 33190-34254 | EveU8 | 354 | Unknown | ANT_24670 (Anaerolinea thermophila UNI-1) | 44 | YP_004175093 |
| | 34375-35229 | EveU9 | 284 | Unknown | Rleg_3584 (Rhizobium leguminosarum) | 50 | YP_002977369 |
| | 35226-36314 | EveM8 | 362 | O-methyltransferase | KanP (Streptomyces kanamyceticus) | 49 | CAF60515 |
| | 36361-37116 | EveX2 | 251 | RNA methyltransferase | AviRa (Streptomyces viridochromogenes) | 56 | 1O9G_A |

FIG. 11 continued

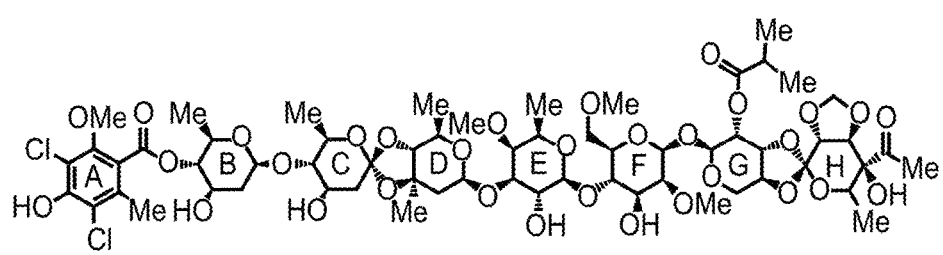
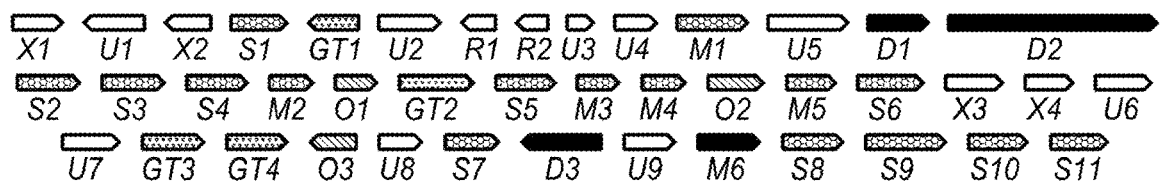
FIG. 12

| GenBank Accession # | Start/Stop (bp) | Gene | Size (#aa) | Proposed function | Protein Homolog | Identity (%) | Gen Bank Accession # |
|---|---|---|---|---|---|---|---|
| AX574197 | 1-858 | AvaX1 | 285 | RNA methyltransferase | AviRb (Streptomyces viridochromogenes) | 90 | Q9F5K6 |
| | 1847-816 | AvaU1 | 343 | Unknown | MCAG_03660 (Micromonospora sp. ATCC39149) | 64 | ZP_04607403 |
| | 2721-1969 | AvaX2 | 250 | RNA methyltransferase | AviRa (Streptomyces viridochromogenes) | 86 | Q9F5K5.2 |
| | 2966-3934 | AvaS1 | 322 | 4-epimerase | AviQ1 (Streptomyces viridochromogenes) | 86 | AAK83169 |
| | 4822-3986 | AvaGT1 | 278 | Glycosyltransferase | AviGT2 (Streptomyces viridochromogenes) | 88 | AAK83170 |
| | 5044-6114 | AvaU2 | 356 | Unknown | AviX9 (Streptomyces viridochromogenes) | 87 | AAK83171 |
| | 6641-6111 | AvaR1 | 176 | Regulator | AviC1 (Streptomyces viridochromogenes) | 70 | AAK83172 |
| | 7412-6936 | AvaR2 | 158 | Regulator | AviC2 (Streptomyces viridochromogenes) | 89 | AAK83173 |
| | 7639-8049 | AvaU3 | 136 | Unknown | AviX10 (Streptomyces viridochromogenes) | 93 | AAK83174 |
| | 8046-8741 | AvaU4 | 231 | Unknown | AviX11 (Streptomyces viridochromogenes) | 91 | AAK83175 |
| | 8738-9961 | AvaM1 | 407 | C-methyltransferase | AviG1 (Streptomyces viridochromogenes) | 91 | AAK83176 |
| | 9975-11390 | AvaU5 | 471 | Unknown | AviJ (Streptomyces viridochromogenes) | 85 | AAK83177 |
| | 11546-12580 | AvaD1 | 344 | Acyltransferase | AviN (Streptomyces viridochromogenes) | 85 | AAK83178 |
| | 12577-16431 | AvaD2 | 1284 | Polyketide synthase | AviM (Streptomyces viridochromogenes) | 86 | AAK83194 |
| | 16614-17690 | AvaS2 | 358 | Glucose-1-phosphate thymidyltransferase | AviD (Streptomyces viridochromogenes) | 89 | AAK83195 |
| | 17687-18763 | AvaS3 | 358 | 4,6-dehydratase | AviE1 (Streptomyces viridochromogenes) | 91 | AAK83196 |
| | 18842-19870 | AvaS4 | 342 | 4-epimerase | AviQ2 (Streptomyces viridochromogenes) | 94 | AAK83179 |
| | 19960-20676 | AvaM2 | 238 | Methyltransferase | AviG5 (Streptomyces viridochromogenes) | 82 | AAK83180 |
| | 20711-21394 | AvaO1 | 227 | Oxidase (MDB) | AviO1 (Streptomyces viridochromogenes) | 93 | AAK83181 |
| | 21451-22734 | AvaGT2 | 427 | Glycosyltransferase | AviGT1 (Streptomyces viridochromogenes) | 91 | AAK83182 |
| | 22731-23744 | AvaS5 | 337 | 4,6-dehydratase | AviE2 (Streptomyces viridochromogenes) | 90 | AAK83183 |
| | 23777-24469 | AvaM3 | 230 | Methyltransferase | AviG2 (Streptomyces viridochromogenes) | 90 | AAK83184 |
| | 24512-25228 | AvaM4 | 238 | Methyltransferase | AviG6 (Streptomyces viridochromogenes) | 91 | AAK83186 |
| | 25239-26183 | AvaO2 | 314 | Orthoester synthase | AviO3 (Streptomyces viridochromogenes) | 89 | AAK83187 |
| | 26177-27013 | AvaM5 | 278 | Methyltransferase | AviG3 (Streptomyces viridochromogenes) | 87 | AAK83188 |
| | 27037-28200 | AvaS6 | 378 | Epimerase | AviX12 (Streptomyces viridochromogenes) | 96 | AAK83189 |
| | 28197-29168 | AvaX3 | 323 | ABC transporter | AviABC1 (Streptomyces viridochromogenes) | 89 | AAG32068 |
| | 29165-29962 | AvaX4 | 265 | ABC transporter | AviABC2 (Streptomyces viridochromogenes) | 95 | AAG32069 |
| | 30003-30980 | AvaU6 | 325 | Pyruvate dehydrogenase | AviB1 (Streptomyces viridochromogenes) | 89 | AAK83190 |
| | 30980-31942 | AvaU7 | 320 | Pyruvate dehydrogenase | AviB2 (Streptomyces viridochromogenes) | 95 | AAK83191 |
| | 31939-32988 | AvaGT3 | 349 | Glycosyltransferase | AviGT3 (Streptomyces viridochromogenes) | 89 | AAK83192 |

FIG. 12 continued

| GenBank Accession # | Start/Stop (bp) | Gene | Size (#aa) | Proposed function | Protein Homolog | Identity (%) | Gen Bank Accession # |
|---|---|---|---|---|---|---|---|
| | 32985-34013 | AvaGT4 | 342 | Glycosyltransferase | AviGT4 (Streptomyces viridochromogenes) | 90 | 2IV3_A |
| | 34813-34061 | AvaO3 | 250 | Orthoester synthase | MCAG_03658 (Micromonospora sp. ATCC39149) | 69 | ZP_04607401 |
| | 35036-35737 | AvaU8 | 233 | Unknown | MCAG_03657 (Micromonospora sp. ATCC39149) | 62 | ZP_04607400 |
| | 35773-36678 | AvaS7 | 301 | 4-epimerase | MCAG_03656 (Micromonospora sp. ATCC39149) | 61 | ZP_04607399 |
| | 38237-36855 | AvaD3 | 460 | Halogenase | MCAG_03648 (Micromonospora sp. ATCC39149) | 76 | ZP_04607391 |
| | 38513-39367 | AvaU9 | 284 | Unknown | MCAG_03672 (Micromonospora sp. ATCC39149) | 72 | ZP_04607415 |
| | 39369-40415 | AvaM6 | 348 | O-methyltransferase | MCAG_03673 (Micromonospora sp. ATCC39149) | 59 | ZP_04607416 |
| | 40636-41682 | AvaS8 | 348 | 4,6-dehydratase | MCAG_03650 (Micromonospora sp. ATCC39149) | 74 | ZP_04607392 |
| | 41676-43076 | AvaS9 | 466 | 2,3-dehydratase | MCAG_03651 (Micromonospora sp. ATCC39149) | 67 | ZP_04607394 |
| | 43081-44091 | AvaS10 | 336 | Ketoreductase | MCAG_03652 (Micromonospora sp. ATCC39149) | 60 | ZP_04607395 |
| | 44081-45055 | AvaS11 | 324 | 4-ketoreductase | MCAG_03653 (Micromonospora sp. ATCC39149) | 53 | ZP_04607396 |

FIG. 12 continued

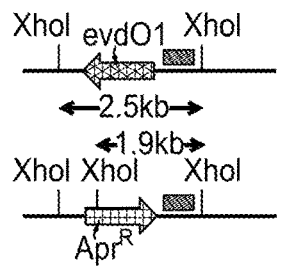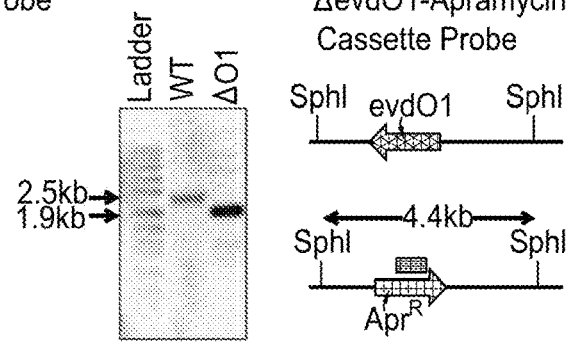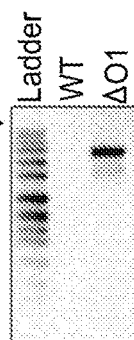
FIG. 18A
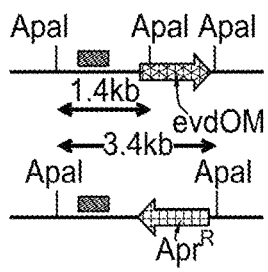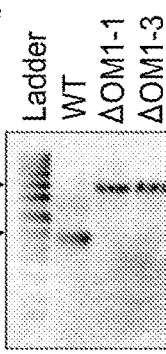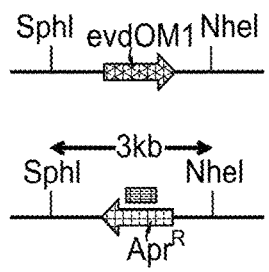
FIG. 18B
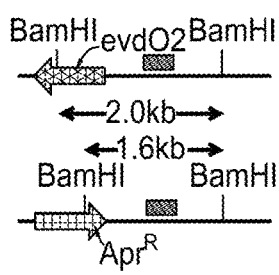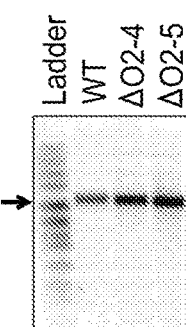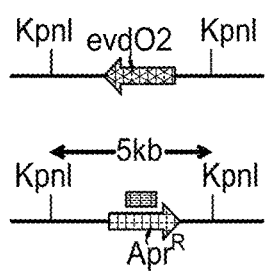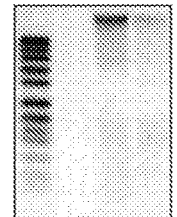
FIG. 18C

| Pos. | 13C | 1H | HMBC | NOESY |
|---|---|---|---|---|
| 1 | 155.7 | | | |
| 2 | 114.6 | | | |
| 3 | 153.9 | | | |
| 4 | 117.8 | | | |
| 5 | 134.2 | | | |
| 6 | 119.7 | | | |
| 7 | 61.1 | 3.88, 3H, s | 3 | |
| 8 | 17.4 | 2.36, 3H, s | 2, 3, 4, 5, 6 | |
| 9 | 166.7 | | | |
| 10 | 100.0 | 4.72, 1H, dd (9.4, 10.8 Hz) | 11, 19 | 11, 12, 14, 19 |
| 11 | 36.1 | 1.63, 1H, m | 10, 12 | |
| | | 2.45, 1H, ddd (3.8, 5.3, 11 Hz) | 10, 12, 13 | 10, 12, 22 |
| 12 | 72.7 | 3.97, 1H, overlap | 13, 22 | 10, 11, 14, 22 |
| 13 | 75.9 | 4.81, 1H, overlap | 9, 12, 13, 14, 15 | |
| 14 | 70.7 | 3.59, 1H, overlap | 10, 13, 15 | 10, 12, 15 |
| 15 | 17.3 | 1.35, 3H, d (6.4 Hz) | 13, 14 | |
| 16 | 176.8 | | | |
| 17 | 39.3 | 2.56, 2H, broad | 16, 18 | |
| 18 | 68.0 | 4.25, 1H, broad | | 19 |
| 19 | 84.0 | 3.53, 1H, overlap | 10 | 10 |
| 20 | 67.2 | 3.95, 1H, overlap | | 19 |
| 21 | 18.2 | 1.23, 3H, d (6.3 Hz) | 19, 20 | |
| 22 | 93.2 | 5.05, 1H, d (4.8 Hz) | 12, 24, 26 | 11, 12, 23 |
| 23 | 38.3 | 1.65, 1H, dd (1.9, 2.8 Hz) | 22, 24, 27 | |
| | | 2.86, 1H, overlap | 22, 24, 27 | |
| 24 | 73.9 | | | |
| 25 | 82.3 | 3.58, 1H, overlap | 26, 28 | 29 |
| 26 | 65.4 | 3.59, 1H, overlap | 25 | 27 |
| 27 | 18.9 | 1.65, 3H, s | 22, 23, 24, 25 | 22, 23, 26, 47 |
| 28 | 60.1 | 3.28, 3H, s | 25 | 29 |
| 29 | 16.7 | 0.79, 3H, d (5 Hz) | 25, 26 | |
| 30 | 172.9 | | | |
| 31 | 39.4 | 2.25, 1H, d (16.8 Hz) | 30, 33 | |
| | | 2.60, 1H overlap | 30, 32 | |

| Pos. | $^{13}C$ | $^{1}H$ | HMBC | NOESY |
|---|---|---|---|---|
| 32 | 66.3 | 3.83, 1H, broad (10.2 Hz) | 30, 31, 45 | 31, 34, 35 |
| 33 | 40.8 | 1.91, 1H, overlap | 34, 35 | |
| 34 | 82.5 | 3.67, 1H, broad (10 Hz) | 33, 35, 36, 45, 46, 53 | 32, 35, 47, 53 |
| 35 | 34.6 | 1.71, 1H, m | | |
| 36 | 32.3 | 1.51, 1H, overlap | 37, 40 | |
|  |  | 1.93, 1H | 37, 46, 48 | |
| 37 | 45.4 | 2.64, 1H, overlap | 38 | |
| 38 | 201.4 | | | |
| 39 | 123.2 | 6.68, 1H, d (15.7 Hz) | 38, 41 | 48, 49 |
| 40 | 150.6 | 6.45, 1H, d (15.7 Hz) | 38, 39, 42, 49 | 42 |
| 41 | 59.6 | | | |
| 42 | 68.2 | 2.84, 1H, d (9.6 Hz) | 40, 41, 43, 50 | |
| 43 | 37.6 | 1.74, 1H, m | 42, 44, 50 | |
| 44 | 76.8 | 4.86, 1H, overlap | 30, 43, 51, 52 | |
| 45 | 8.5 | 1.09, 3H, d (6.5 Hz) | 32, 33, 34 | |
| 46 | 30.0 | 2.51, 1H, overlap | | |
|  |  | 2.88, 1H, overlap | 47 | |
| 47 | 142.1 | 7.36, 1H, broad | 46 | 27, 34 |
| 48 | 16.3 | 1.17, 3H, d (7 Hz) | 36, 37, 38 | |
| 49 | 13.9 | 1.46, 3H, s | 40, 41, 42 | 39, 43 |
| 50 | 13.2 | 1.12, 3H, d (6.7 Hz) | 42, 43, 44 | |
| 51 | 24.2 | 1.54, 1H, overlap | 43, 44, 52 | |
|  |  | 1.83, 1H, m | 43, 52 | |
| 52 | 8.05 | 0.91, 3H, t (7.3 Hz) | 44, 51 | |
| 53 | 103.5 | 4.32, 1H, d (7.2 Hz) | 34, 55 | 34, 57 |
| 54 | 69.1 | 3.41, 1H, dd (7.2, 10.5 Hz) | 53, 55 | 59 or 60 |
| 55 | 65.3 | 3.30, 1H, overlap | 54 | 57 |
| 56 | 29.8 | 1.43, 1H, overlap | 57, 58 | |
|  |  | 1.92, 1H | | |
| 57 | 68.1 | 3.57, 1H, overlap | 59, 61 | 53 |
| 58 | 19.9 | 1.19, 3H, d (6.2 Hz) | 56, 57 | |
| 59 | 38.7 | 2.77, 3H, s | 55, 60 | |
| 60 | 38.7 | 2.77, 3H, s | 55, 59 | |

FIG. 19 continued

| Pos. | ¹³C | ¹H | HMBC |
|---|---|---|---|
| 1 | ? | | |
| 2 | 113.3 | | |
| 3 | 154.0 | | |
| 4 | ? | | |
| 5 | 133.7 | | |
| 6 | 121.1 | | |
| 7 | 60.7 | 3.87, 3H, s | 3 |
| 8 | 17.5 | 2.34, 3H, s | 4, 5, 6 |
| 9 | 166.8 | | |
| 10 | 100.3 | 4.73, 1H, dd (9.4, 10.8 Hz) | 11, 19 |
| 11 | 36.2 | 1.66, 1H, m | 10, 12 |
|  |  | 2.45, 1H, m | 10, 12 |
| 12 | 72.3 | 4.01, 1H, m | 11, 13, 14 |
| 13 | 74.9 | 4.85, 1H, overlap | 9, 12, 14 |
| 14 | 70.8 | 3.71, 1H, overlap | 13, 15 |
| 15 | 17.2 | 1.35, 3H, overlap | 14 |
| 16 | 120.2 | | |
| 17 | 39.9 | 1.73, 1H, | 16 |
|  |  | 2.25, 1H | 16, 18, 19 |
| 18 | 68.1 | 3.77, 1H, overlap | 17, 19 |
| 19 | 86.8 | 3.14, 1H, dd (8.9, 9.2 Hz) | 10, 18, 20, 21 |
| 20 | 70.0 | 3.77, 1H, overlap | 19, 21 |
| 21 | 16.5 | 1.26, 3H, overlap | 19, 20 |
| 22 | 102.0 | 5.05, 1H, overlap | 23, 31 |
| 23 | 43.2 | 1.78, 1H, dd (1.9, 2.8 Hz) | 24 |
|  |  | 2.35, 1H, overlap | 22, 24 |
| 24 | 78.7 | | |
| 25 | 85.0 | 3.34, 1H, overlap | |
| 26 | 68.1 | 3.83, 1H, overlap | 28 |
| 27 | 18.7 | 1.36, 3H, s | 23, 24, 25 |
| 28 | 17.4 | 1.29, 3H, d (6.5 Hz) | 25, 26 |

| Pos. | $^{13}$C | $^1$H | HMBC |
|---|---|---|---|
| 29 | 103.9 | 4.21, 1H, d (7.7 Hz) | 30, 39 |
| 30 | 70.1 | 3.51, 1H, overlap | |
| 31 | 82.7 | 3.59, 1H, overlap | 32 |
| 32 | 81.4 | 3.51, 1H, broad (10.2 Hz) | |
| 33 | 70.5 | 3.71, 1H, overlap | 35 |
| 34 | 60.7 | 3.57, 3H, s | 32 |
| 35 | 15.1 | 1.26, 3H, overlap | 33 |
| 36 | 95.9 | 4.82, 1H, overlap | 44 |
| 37 | 79.6 | 41 | |
| 38 | ? | | |
| 39 | 77.7 | 3.98, 1H, overlap | 29 |
| 40 | ? | | |
| 41 | 58.1 | 3.51, 3H, s | 37 |
| 42 | 70.5 | 3.75, 2H, overlap | |
| 43 | 57.9 | 3.38, 3H, s | 42 |
| 44 | 94.9 | 5.25, 1H, d (1.4 Hz) | 36, 45 |
| 45 | 72.5 | 3.97, 1H, overlap | 46 |
| 46 | 80.6 | 3.95, 1H, dd (2.5, 10.1 Hz) | |
| 47 | 69.1 | 4.26, 1H, ddd (4.4, 10, 15 Hz) | |
| 48 | 62.9 | 3.80, 1H, overlap | 46, 47 |
| | | 4.07, 1H, dd (4.7, 9.9 Hz) | 46 |
| 49 | 119.7 | | |
| 50 | 72.8 | 3.87, 1H, overlap | |
| 51 | 76.8 | 3.87, 1H, overlap | |
| 52 | 75.3 | | |
| 53 | 69.1 | 3.62, 1H, overlap | 49, 51, 52 |
| | | 3.92, 1H, d (12.2 Hz) | |
| 54 | 95.4 | 5.02, 1H, s | 50 |
| | | 5.06, 1H, s | |
| 55 | 79.5 | 3.31, 1H, d (6.2 Hz) | 56 |
| 56 | 56.3 | 3.34, 3H, s | 55 |
| 57 | 12.5 | 1.25, 3H, overlap | 52, 55 |
| 58 | 93.1 | 5.06, 1H, overlap | 12, 59 |
| 59 | 38.3 | 1.64, 1H, overlap | 60 |
| | | 2.85, 1H, overlap | 60, 63 |
| 60 | 73.9 | | |
| 61 | 82.3 | 3.57, 1H, overlap | 60, 64 |
| 62 | 65.5 | 3.63, 1H, overlap | 61, 65 |
| 63 | 19.1 | 1.65, 3H, s | 59, 60, 61 |
| 64 | 60.1 | 3.28, 3H, s | 61 |
| 65 | 16.8 | 0.82, 3H, d (6 Hz) | 61, 62 |
| 66 | 172.9 | | |
| 67 | 39.5 | 2.27, 1H, overlap | 66 |
| | | 2.61, 1H, overlap | 66 |
| 68 | 66.5 | 3.81, 1H, overlap | |
| 69 | 40.9 | 1.91, 1H, overlap | |
| 70 | 82.3 | 3.69, 1H, overlap | 89 |
| 71 | 34.6 | 1.72. 1H, overlap | |
| 72 | 32.1 | 1.50, 1H, overlap | |
| | | 1.93, 1H, overlap | |
| 73 | 45.4 | 2.64, 1H, overlap | 84 |

FIG. 20 continued

| Pos. | ¹³C | ¹H | HMBC |
|---|---|---|---|
| 74 | 201.6 | | |
| 75 | 123.3 | 6.69, 1H, d (16 Hz) | 74, 76 |
| 76 | 150.6 | 6.42, 1H, d (16 Hz) | 75, 77 |
| 77 | 59.8 | | |
| 78 | 68.2 | 2.85, 1H, overlap | 76, 79 |
| 79 | 37.6 | 1.75, 1H, overlap | 86 |
| 80 | 76.7 | 4.85, 1H, overlap | 79, 87 |
| 81 | 8.4 | 1.09, 3H, d (6.6 Hz) | |
| 82 | 29.8 | 2.50, 1H, overlap | |
| | | 2.91, 1H, m | |
| 83 | 142.2 | 7.40, 1H, broad | |
| 84 | 16.3 | 1.17, 3H, overlap | 72, 73, 74 |
| 85 | 13.9 | 1.46, 3H, overlap | 76, 77, 78 |
| 86 | 13.2 | 1.11, 3H, d (6.8 Hz) | 78, 79, 80 |
| 87 | 24.2 | 1.54, 1H, m | 80 |
| | | 1.82, 1H, overlap | |
| 88 | 8.1 | 0.91, 3H, t (7.4 Hz) | 80, 87 |
| 89 | 103.8 | 4.30, 1H, d (7.1 Hz) | 70 |
| 90 | 69.9 | 3.32, 1H, overlap | |
| 91 | 64.9 | 3.00, 1H, m | 95, 96 |
| 92 | 30.0 | 1.32, 1H, overlap | |
| | | 1.81, 1H, overlap | |
| 93 | 68.5 | 3.49, 1H, overlap | 94 |
| 94 | 20.1 | 1.16, 3H, overlap | 93 |
| 95 | 38.9 | 2.58, 3H, s | 91 |
| 96 | 38.9 | 2.62, 3H, s | 91 |

| Pos. | ¹³C | ¹H | HMBC |
|---|---|---|---|
| 1 | ? | | |
| 2 | 114.8 | | |
| 3 | 154.1 | | |
| 4 | 115.8 | | |
| 5 | 134.2 | | |
| 6 | 120.2 | | |
| 7 | 60.8 | 3.88, 3H, s | 3 |
| 8 | 17.4 | 2.34, 3H, s | 4, 5, 6 |
| 9 | 166.8 | | |
| 10 | 100.2 | 4.75, 1H, dd (4.7, 10 Hz) | 19 |
| 11 | 36.0 | 1.61, 1H, m | |
| | | 2.46, 1H, m | 10, 12, 13 |
| 12 | 72.3 | 3.99, 1H, overlap | 13 |
| 13 | 75.4 | 4.81, 1H, overlap | 9, 12, 14 |
| 14 | 70.8 | 3.72, 1H, m | |
| 15 | 17.3 | 1.38, 3H, d (6.4 Hz) | 13, 14 |
| 16 | 119.9 | | |
| 17 | 39.4 | 1.84, 1H, dd (9.7, 12.7 Hz) | 16, 18 |
| | | 2.33, 1H, dd (5, 12.7 Hz) | |
| 18 | 68.1 | 3.84, 1H, overlap | |
| 19 | 86.7 | 3.17, 1H, t (9 Hz) | 10, 18, 20, 21 |
| 20 | 69.9 | 3.73, 1H, m | |
| 21 | 16.7 | 1.26, 3H, overlap | 19, 20 |
| 22 | 102.5 | 4.80, 1H, overlap | 23, 30 |
| 23 | 68.3 | 4.41, 1H, dd (1.9, 2.8 Hz) | 22, 24, 25 |
| 24 | 78.3 | 3.78, 1H, overlap | 25 |
| 25 | 76.3 | 3.69, 1H, overlap | |
| 26 | 71.3 | 3.66, 1H, m | |
| 27 | 17.3 | 1.31, 3H, d (5.5 Hz) | 25, 26 |
| 28 | 103.5 | 4.24, 1H, d (7.8 Hz) | 38 |
| 29 | 70.13 | 3.57, 1H, overlap | 28, 30 |
| 30 | 82.8 | 3.67, 1H, overlap | 22, 32 |
| 31 | 81.2 | 3.51, 1H, overlap | 29, 30, 33 |
| 32 | 70.7 | 3.72, 1H, m | 31 |
| 33 | 60.7 | 3.61, 3H, s | 31 |
| 34 | 15.2 | 1.27, 3H, overlap | 31, 32 |
| 35 | 95.8 | 4.83, 1H, overlap | 36, 43 |
| 36 | 79.8 | 3.63, 1H, overlap | 37, 40 |
| 37 | 72.3 | 3.65, 1H, overlap | |
| 38 | 77.0 | 3.69, 1H, overlap | 28, 37, 39 |
| 39 | 74.6 | 3.45, 1H, m | |
| 40 | 60.7 | 3.56, 3H, s | 36 |
| 41 | 70.5 | 3.75, 2H, overlap | |
| 42 | 57.9 | 3.37, 3H, s | 41 |
| 43 | 97.5 | 5.15, 1H, overlap | 35, 44, 47 |
| 44 | 68.6 | 4.31, 1H, overlap | 45, 46 |
| 45 | 80.5 | 3.89, 1H, dd (2.7, 10.3 Hz) | |
| 46 | 68.8 | 4.34, 1H, overlap | |
| 47 | 63.0 | 3.82, 1H, overlap | |
| | | 4.08, 1H, dd (4.5, 9.7 Hz) | 43, 45, 46 |
| 48 | 119.8 | | |
| 49 | 72.8 | 3.88, 1H, overlap | 50 |

FIG. 21 continued

| Pos. | $^{13}C$ | $^{1}H$ | HMBC |
|---|---|---|---|
| 50 | 77.0 | 3.87, 1H, overlap | 49 |
| 51 | 75.7 | | |
| 52 | 68.9 | 3.61, 1H, overlap | 48, 50, 51 |
|  |  | 4.01, 1H, d (12.3 Hz) | 51 |
| 53 | 95.3 | 5.02, 1H, overlap | 49 |
|  |  | 5.06, 1H, overlap | 50 |
| 54 | 79.5 | 3.31, 1H, m | 50, 51, 52, 55 |
| 55 | 56.1 | 3.33, 1H, s | 54 |
| 56 | 12.6 | 1.25, 3H, overlap | 51, 54 |
| 57 | 92.8 | 5.03, 1H, dd | 59, 61 |
| 58 | 40.2 | 2.08, 1H, dd (1, 13 Hz) | 57, 59, 60 |
|  |  | 2.44, 1H, dd (5, 13.5 Hz) | 59, 62 |
| 59 | 89.9 | | |
| 60 | 84.4 | 3.60, 1H, overlap | 59, 61, 63 |
| 61 | 65.9 | 3.51, 1H, m | |
| 62 | 18.4 | 1.68, 3H, s | 58, 59, 60 |
| 63 | 59.7 | 3.30, 3H, s | 60 |
| 64 | 16.5 | 0.77, 3H, d (6 Hz) | 60, 61 | des-methyl Ever D $R_1$ = $NO_2$; $R_2$ = OH
des-methyl Ever E $R_1$ = $NH_2$; $R_2$ = OH
des-methyl Ever F $R_1$ = NHOH; $R_2$ = OH
des-methyl Ever G $R_1$ = NO; $R_2$ = OH Ever R $R_1$ = OH; $R_2$ = OH
Ever S $R_1$ = OH; $R_2$ = OMe Everninomicin Q

BIOSYNTHESIS OF EVERNINOMICIN ANALOGS IN *MICROMONOSPORA CARBONACEA* VAR *AURANTIACA*

CROSS REFERENCE TO RELATED APPLICATIONS

This application claims the benefit of priority to U.S. Provisional Application No. 62/265,126, filed Dec. 9, 2015, which is incorporated by reference herein in its entirety.

BACKGROUND

The increasing prevalence of drug-resistant bacteria in the clinical setting has necessitated the need for new antibacterial agents. According to the 2013 report by the Centers for Disease Control and Prevention, antibiotic resistance infections resulted in more than 2,049,442 illnesses and 23,000 deaths. Methicillin-resistant *Staphylococcus aureus* (MRSA) and vancomycin-resistant enterococci (VRE) alone are responsible for approximately 100,000 infections and about half of the deaths each year. With these dangerous infections raging in the clinic, there is a desperate need for new antibiotics. While modification of tried and true scaffolds is the simplest method for generating new antimicrobials, new scaffolds with novel targets are needed. Most current classes of antibiotics were discovered during the "golden era" of antibiotic research from the 1930s to the 1970s. However, from the early 1970s to 1999, only one new class of antibiotic was launched. Although the situation has improved somewhat with the approval of five new classes of antibiotics since 2000, the statistics presented above show that there is still a desperate need for new classes of antibiotics with novel modes of actions that will not exhibit cross-resistance with those currently on the market.

Orthosomycins, polysaccharides defined by an orthoester linkage, are an underexplored class of antibiotics. Everninomicins are broad spectrum orthosomycin antibiotics produced by the soil bacterium *Micromonospora carbonacea* and that display activity against a variety of Gram-positive organisms including MRSA and VRE. To date, fourteen everninomicins have been reported. FIG. 1 shows the variety of everninomicins isolated from *Micromonospora carbonacea*. All everninomicins, with the exception of Ever-2, which lacks the A ring nitrosugar, are octasaccharides containing dichloroisoeverninic acid. The majority of everninomicins also contain orsellinic acid at the opposite end of the saccharide chain. Everninomicins possess three unique oxidative features. The first is a methylenedioxy bridge attached to ring F. The second is its namesake orthoester linkages located between rings C and D and rings G and H. Finally, L-evernitrose (ring A) is a nitrosugar unique to everninomicins. In contrast with the other polysaccharides, the everninomicins contain a large proportion of deoxy sugars. Rings A, B (D-olivose), and C (D-olivose), and sometimes ring D (D-evalose) are all 2,6-dideoxy sugars while ring E (4-O-methyl-D-fucose) is 6-deoxygenated. Ring F is 2,6-di-O-methyl-D-mannose, ring G is L-lyxose, and ring H is eurekanate.

Avilamycins, produced by *Streptomyces viridochromogenes* Tü57, are heptasaccharides similar to everninomicin but lacking the nitrosugar. At least sixteen avilamycins have been characterized to date (FIG. 1). Avilamycins have the same seven-sugar core as the everninomicins. All avilamycins contain dichloroisoeveminic acid but lack orsellinic acid at the eastern side of the molecule. The main points of differentiation among the avilamycins are the decorations of rings G and H. As in the everninomicins, the avilamycins also contain a methylenedioxy bridge and two orthoester linkages located between rings C and D and rings G and H.

Interest in the everninomicins peaked in the early 2000s when Schering-Plough Corporation (now Merck & Co.) was developing everninomicin A (Ziracin) as an antimicrobial agent. Everninomicin A (1) advanced to phase III clinical trials before being discontinued due to a poor balance between efficacy and safety. However, investigation of the orthosomycins is still of interest as members of this class possess potent activity against clinically important strains such as methicillin-resistant staphylococci, glycopeptide-resistant enterococci, vancomycin-resistant enterococci, and penicillin-resistant streptococci, and may be effective for treating infective endocarditis.

The orthosomycins act as bacterial translation inhibitors; although, they target a different site on the large ribosomal subunit than other antibiotics currently on the market. Everninomicin has been shown to bind to a unique site on the 50S ribosomal subunit and prevent formation of the 70S initiation complex in an IF2 dependent manner thereby inhibiting bacterial translation. Specifically, everninomicin appears to interact with ribosomal protein L16 and r23S RNA helices 89 and 91 (FIG. 2). Everninomicin is also a potent inhibitor of back-translocation by inhibiting the GTPase activity of EF-4.

Due to their activity against a variety of drug-resistant Gram-positive bacteria as well as their novel bacterial targets, the orthosomycins can be clinically useful drugs. Nature has already provided a variety of everninomicins to begin understanding their structure-activity relationship. This is encouraging as the natural pathway appears to contain some flexibility and promiscuity as to substrates. Unfortunately, making analogs by chemical synthesis is impractical as the total synthesis involves over 130 steps. Therefore, there is a need to access new eveminomicin congeners with pharmacological and biological properties. The methods and compositions disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to methods of preparing evemi-nomicin analogs by genetic alteration of *Micromonospora carbonacea*. Everninomicin analogs prepared by these methods and methods of using these analogs to treat infections are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 1 contains structures of everninomicins and avilamycins.

FIG. 2 shows the ribosomal binding site of orthosomycin antibiotics. Small ribosomal subunit (PDB 2J00) is shown in dark grey and large subunit (PDB 2J01) is shown in lighter grey. The A and P sites are shown in salmon. Ribosomal protein L16 is shown in green (chain Q), helix 89 (chain A, residues 2454-2498) in blue, and helix 91 (chain A, residues 2520-2545) in magenta. Amino acid residues and nucleotides known to interact with everninomicin and avilamycin are highlighted in yellow.

FIG. 3 contains structures of new everninomicins Ever-2, and Ever-H (11), Ever J (12), and Ever-K (13). Also shown are the mass spectra fragmentation patterns. Dashed lines indicate position of cleavage during fragmentation experiments.

FIG. 6A shows activity of everninomicin A against *S. aureus* subsp. *aureus* Rosenbach at various concentrations. FIG. 6B shows activity of full-length everninomicin-rosaramicin conjugate against *S. aureus* subsp. *aureus* Rosenbach at various concentrations. FIG. 6C shows activity of truncated everninomicin-rosaramicin conjugate against *S. aureus* subsp. *aureus* Rosenbach at various concentrations.

FIG. 12 is a depiction and deduced functional assignment of ORFs from the ava gene cluster of *S. mobaraensis*.

FIGS. 18A-18C show results from Southern hybridization of targeted deletion mutants verifying a double crossover event. FIG. 18A is a Southern blot analysis of ΔevdO1::aac(3)IV. Diagrams depict the relative shifts expected for replacement of evdO1 with the apramycin cassette. Blots show predicted shifts were observed experimentally, thus confirming the double crossover. FIG. 18B is a Southern blot analysis of ΔevdMO1::aac(3)IV. Diagrams depict the relative shifts expected for replacement of evdMO1 with the apramycin cassette. Blots show predicted shifts were observed experimentally, thus confirming the double crossover. FIG. 18C is a Southern blot analysis of ΔevdO2::aac(3)IV. Diagrams depict the relative shifts for replacement of evdO2 with the apramycin cassette. Blots do not have predicted shifts showing that the gene replacement was not successful. Ladder is DNA molecular weight marker VII, DIG-labeled (product no. 11669940910; Roche Life Sciences). WT is wild-type *M. carbonacea* var *aurantiaca*. ApaI, KpnI, NheI, XhoI, SphI, and BamHI are restriction endonucleases used to cleave the genomic DNA into predictably sized fragments. Blots show predicted shifts were observed experimentally, thus confirming the double crossover.

FIG. 22A is a chromatogram showing summed ion intensities in negative mode for everninomicins D-G and novel metabolites. FIG. 22B shows the structure for ΔevdM5::aac(3)IV metabolites. FIG. 22C shows the fragmentation pattern for des-methyl Ever F.

FIG. 23A is a chromatogram showing summed ion intensities in negative mode for everninomicins D-G and novel metabolites. FIG. 23B shows structure for ΔevdD2::aac(3)IV metabolites.

IV). FIG. 24A is a chromatogram showing summed ion intensities in negative mode for everninomicins D-G and novel metabolites. FIG. 24B shows fragmentation pattern for everninomicin Q.

DETAILED DESCRIPTION

Figure 4:
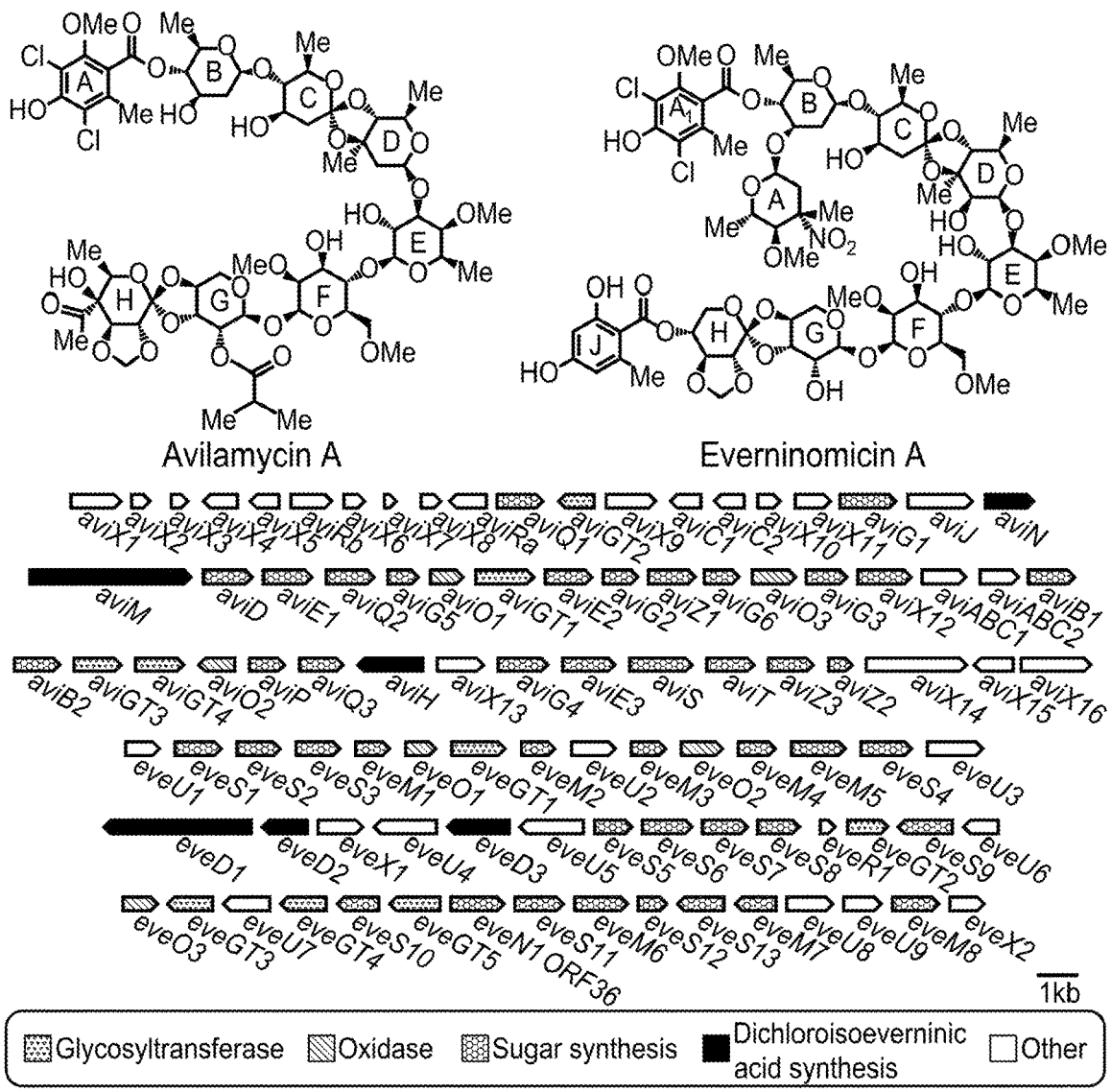
FIG. 4 shows the structures of avilamycin A and everninomicin A. Avi gene cluster from *S. viridichromogenes* Tü57 and eve gene cluster from *M. carbonacea* var *africana*. Genes are shaded according to putative functions.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an antibiotic" includes mixtures of two or more such antibiotics, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., bacterial growth or infection). It is understood that this is typically in relation to some standard or expected value, in other words it is relative, but that it is not always necessary for the standard or relative value to be referred to. For example, "reduces bacterial growth" means decreasing the amount of bacteria relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as bacterial growth or infection), diminishment of extent of infection, stabilized (i.e., not worsening) state of infection, preventing or delaying spread of the infection, preventing or delaying occurrence or recurrence of infection, and delay or slowing of infection progression.

The term "patient" preferably refers to a human in need of treatment with an antibiotic or treatment for any purpose, and more preferably a human in need of such a treatment to treat bacterial infection. However, the term "patient" can also refer to non-human animals, preferably mammals such as dogs, cats, rabbits, horses, cows, pigs, sheep, goats, and non-human primates, among others, that are in need of treatment with an antibiotics. In other examples, the term "patient" can refer to poultry.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol as described herein.

The symbols $A''$ is used herein as merely a generic substituent in the definitions below.

The term "alkoxy" as used herein is an alkyl group bound through a single, terminal ether linkage; that is, an "alkoxy" group can be defined as $—O^{A^1}$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol as described herein.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol as described herein.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O—.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN.

The term "azido" as used herein is represted by the formula —$N_3$.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methyl-glucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to infection, an effective amount comprises an amount sufficient to cause a bacterial cell to shrink and/or to decrease the growth rate of the cells (such as to suppress bacterial growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of infection, the effective amount of the drug or composition may: (i) reduce the number of bacterial cells; (ii) inhibit, retard, slow to some extent and preferably stop bacterial cell infiltration into peripheral organs; (iii) inhibit bacterial growth; (iv) prevent or delay occurrence and/or recurrence of infection; and/or (v) relieve to some extent one or more of the symptoms associated with the infection.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Biology Definition

The use of italics indicates a nucleic acid molecule (e.g., enrJ cDNA, gene, etc.); normal text indicates the polypeptide or protein.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar unction may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, ad even more preferably at least 90%, and which has the same or substantially similar properties or functions as the native or parent protein or enzyme to which it is compared.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. The term "variant" may also be used to indicate a modified or altered gene, DNA sequence, enzyme, cell, etc., i.e., any kind of mutant.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when the encoded polypeptides are at least 35-40% similar as determined by one of the algorithms disclosed herein, preferably at least about 60%, and most preferably at least about 90 or 95% in a highly conserved domain, or, for alleles, across the entire amino acid sequence. Sequence comparison algorithms include BLAST (BLAST P, BLAST N, BLAST X), FASTA, DNA Strider, the GCG (Genetics Computer Group, Program Manual for the GCG Package, Version 7, Madison, Wis.) pileup program, etc. using the default parameters provided with these algorithms. An example of such a sequence is an allelic or species variant of the specific everninomicin biosynthetic genes of the invention. Sequences that are substantially homologous can be identified by comparing the sequences using standard software available in sequence data banks, or in a Southern hybridization experiment under, for example, stringent conditions as defined for that particular system.

"Amplification" of DNA, as used herein, denotes the use of polymerase chain reaction (PCR) to increase the concentration of a particular DNA sequence within a mixture of DNA sequences. For a description of PCR see Saiki et an, Science, 239:487, 1988.

A "nucleic acid molecule" refers to the phosphate ester polymeric form of ribonucleosides (adenosine, guanosine, uridine or cytidine; "RNA molecules"); or deoxyribonucleosides (deoxyadenosine, deoxyguanosine, deoxythymidine, or deoxycytidine; "DNA molecules"); or any phosphoester analogs thereof, such as phosphorothioates and thioesters, in either single stranded form, or a double-stranded helix; or "protein nucleic acids" (PNA) formed by conjugating bases to an amino acid backbone; or nucleic acids containing modified bases, for example thiouracil, thio-guanine and fluoro-uracil. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Furthermore, the polynucleotides herein may also be oligonucleotides modified with a label capable of providing a detectable signal, either directly or indirectly. Exemplary labels include radioisotopes, fluorescent molecules, biotin, and the like.

A "coding sequence" or a sequence "encoding" an expression product, such as a RNA, polypeptide, protein, or enzyme, is a minimum nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG, though as shown herein, alternative start codons can be used) and a stop codon.

The term "gene", also called a "structural gene" means a DNA sequence that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including a 5'-untranslated region (UTR) and 3'-UTR, as well as the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease Si), as well as protein binding domains (consensus sequences) responsible for the binding of RNA polymerase.

A coding sequence is "under the control of" or "operably (or operatively) associated with" transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as mRNA or a protein. The expression product itself, e.g. the resulting mRNA or protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a heterologous nucleic acid into a host cell. The term "transformation" means the introduction of a heterologous gene, DNA or RNA sequence to a host cell, so that the host cell will express the introduced gene or sequence to produce a desired product. The introduced gene or sequence may also be called a "cloned" or "heterologous" gene or sequence, and may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which heterologous DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra. In a preferred aspect, a host cell of the invention is an actinomycete, preferably of the genus *Streptomyces* (e.g., a host cell as described in Ziermann and Betlach, BioTechniques, 1999, 26:106) or alternatively *Micromonospera*. Additional examples include, but are not limited to, the strains *S. pristinaespiralis* (ATCC 25486), *S. antibioticus* (DSM 40868), *S. bikiniensis* (ATCC 11062), *S. parvulus* (ATCC 12434), *S. glauescens* (ETH 22794), *S. actuosus* (ATCC 25421), *S. coelicolor* (A3(2)), *S. ambofaciens*, *S. lividans*, *S. griseofuscus*, *S. limosus*, and the like (see also Smokvina et al., Proceedings, 1:403-407).

The term "expression system" means a host cell and compatible vector under suitable conditions, e.g., for the expression of a protein coded for by foreign DNA carried by the vector and introduced to the host cell. Common expression systems include *E. coli* host cells and plasmid vectors, although the actinomycte host cell expression systems are preferred for biosynthesis of everninomicin and related products.

The term "heterologous" refers to a combination of elements not naturally occurring. For example, heterologous DNA refers to DNA not naturally located in the cell, or in a chromosomal site of the cell. A heterologous gene is a gene in which the regulatory control sequences are not found naturally in association with the coding sequence. In the context of the present invention, an EV biosynthetic enzyme gene is heterologous to the vector DNA in which it is inserted for cloning or expression, and it is heterologous to a host cell containing such a vector, in which it is expressed, e.g., a K562 cell.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of EV biosynthetic enzyme, or to detect the presence of nucleic acids encoding EV biosynthetic enzyme. In a further embodiment, an oligonucleotide of the invention can form a triple helix with a EV biosynthetic enzyme DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Reference will now be made in detail to specific aspects of the disclosed materials, compounds, compositions, articles, and methods, examples of which are illustrated in the accompanying Examples and Figures.

Compounds

To date four everninomicin congeners, Ever D-G 2-5, have been reported from *M. carbonacea* var *aurantiaca* all of which vary in the oxidation state of the nitrogen on the A ring. Disclosed herein, in certain examples, are everninomicin-rosaramicin conjugates 8 and 9. Rosaramicin (7) is a glycosylated macrolactone also produced by *M. carbonacea*.

(7)
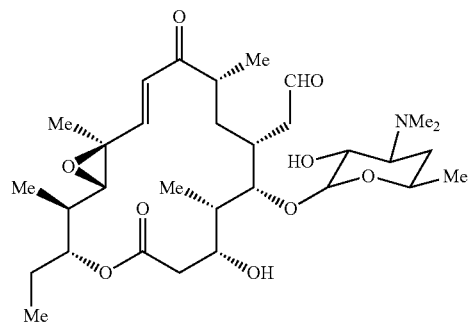
Rosaramicin
(8)
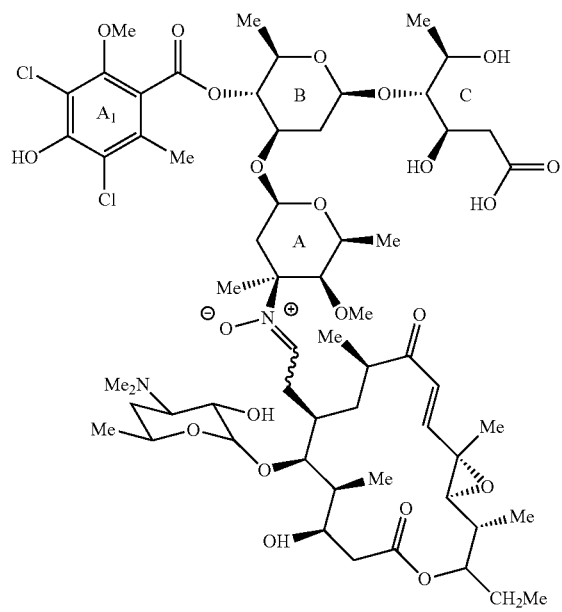
Truncated Everninomicin-Rosaramicin
(9)
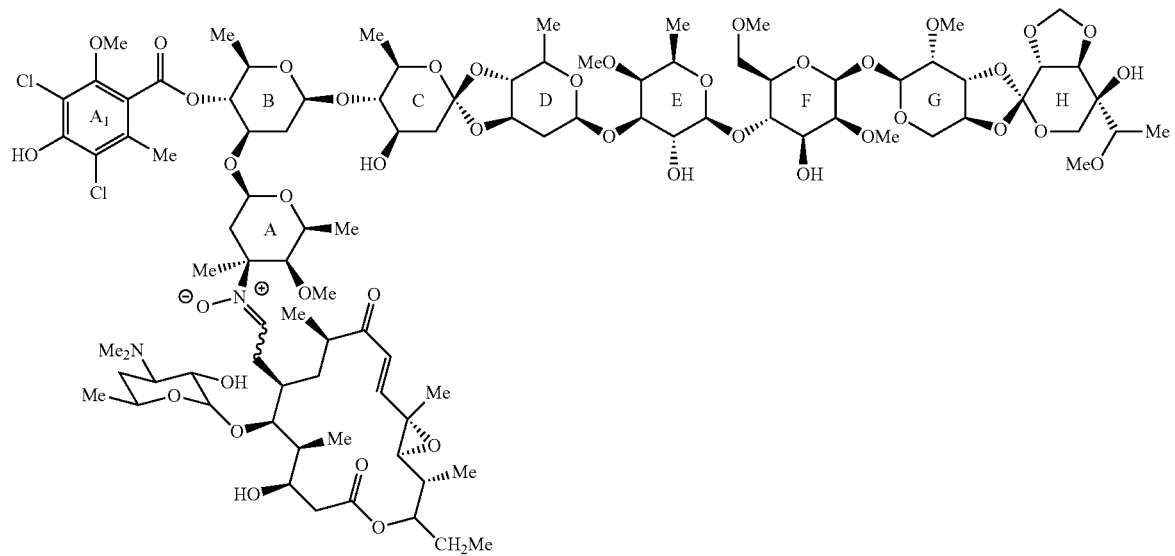
Everninomicin-Rosaramicin The hydroxyl amino functionality of everninomicin F (4) reacts with the aldehyde moiety of rosaramicin to generate a nitrone linkage/to create a nitrone which links the two natural products. The full length everninomicin-rosaramicin conjugate 9 is the intact precursor to the degraded saccharide complex 8. The chemical precedent for formation of the nitrone is well established and the data herein have shown that 9 degrades to 8 when exposed to normal culture conditions. The structures are shown as having either or both cis and trans geometries at the nitrone, thus contemplated herein are the cis, trans, and mixtures thereof. Excitingly, trapping of everninomicins by rosaramicins via nitrone formation results in increased ionization which aids in mass spec identification of new everninomicins. Although Nature has provided natural everninomicin congeners to begin to study the relationship between structure and activity, there is still a need to make non-natural analogs for further study. As chemical synthesis of new analogs is not practical, new analogs are prepared herein by modification of the everninomicin gene cluster.

Disclosed in certain examples are compounds having the structure:

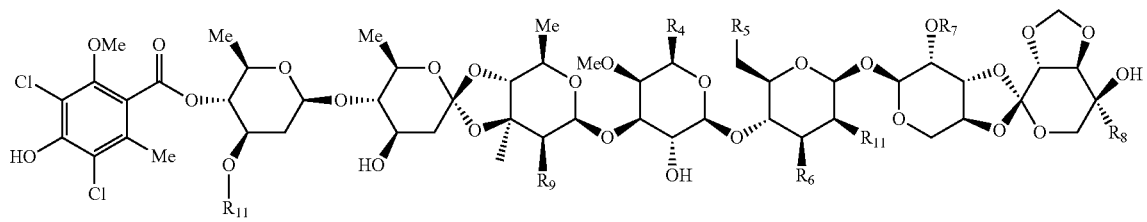

wherein $R_4$-$R_6$ are each, individually, H, OH, $OCH_3$, $CH_2OH$, CHO, $CO_2H$, $CO_2R_{12}$, $C(O)R_{12}$, or substituted $C_1$-$C_6$ alkyl;

$R_7$ is H, $CH_3$, $CH_2OH$, $C(O)R_{12}$, substituted C1-C6 alkyl; or orsellinyl;

$R_8$ is H, OH, $OCH_3$, $CH_2OH$, CHO, $CO_2H$, $CO_2R_{12}$, $C(O)R_{12}$, or substituted $C_1$-$C_6$ alkyl;

$R_9$ is H, OH, $OCH_3$, $CH_2OH$, CHO, $CO_2H$, $CO_2R_{12}$, $C(O)R_{12}$, or substituted $C_1$-$C_6$ alkyl;

$R_{11}$ is H, $NH_2$, $NO_2$, NOH, OMe, $C_1$-C6 alkyl, optionally substituted with alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol, or a 1-20 atom linker bound to rosaramicin; and $R_{12}$ is $C_1$-$C_6$ alkyl, optionally substituted with alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol, or a pharmaceutically acceptable salt thereof.

For example, discloses is a compound having the structure:

(10)

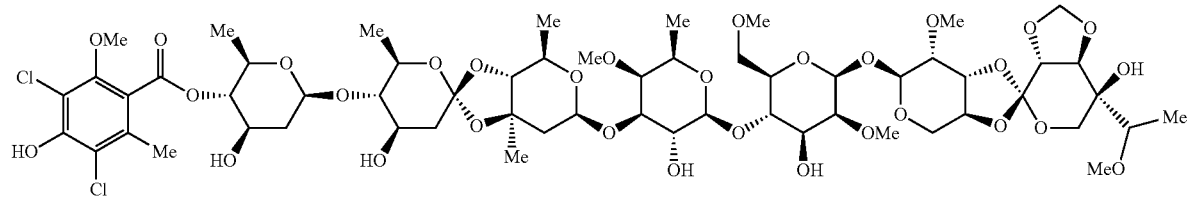

Ever-2 or a pharmaceutically acceptable salt thereof.

Also disclosed are compounds having the structure:

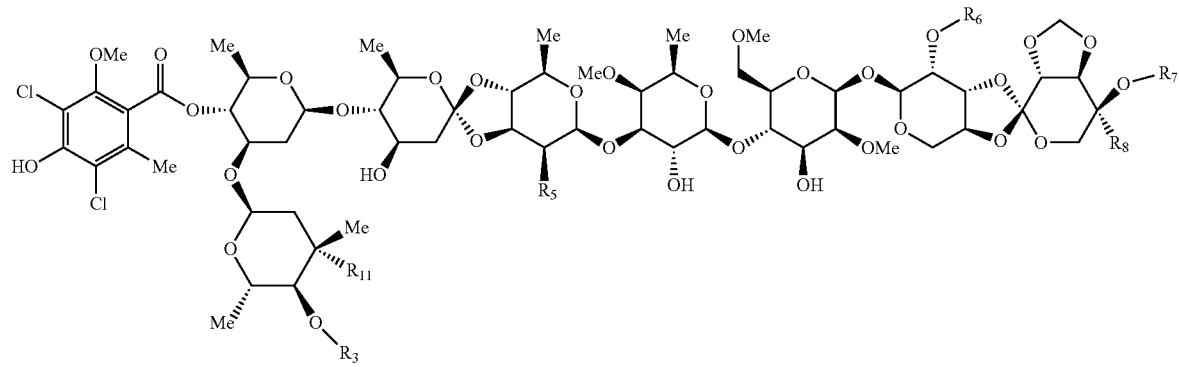

wherein
- $R_3$ and $R_5$ are each, individually, H, OH, $OCH_3$, $CH_2OH$, CHO, $CO_2H$, $CO_2R_{12}$, $C(O)R_{12}$, or substituted $C_1$-$C_6$ alkyl;
- $R_6$ is H, OH, $OCH_3$, $CH_2OH$, CHO, $CO_2H$, $CO_2R_{12}$, $C(O)R_{12}$, substituted $C_1$-$C_6$ alkyl; or orsellinyl;
- $R_7$ is H, OH, $OCH_3$, $CH_2OH$, CHO, $CO_2H$, $CO_2R_{12}$, $C(O)R_{12}$, or substituted $C_1$-$C_6$ alkyl;
- $R_8$ is OH, $OCH_3$, $CH_2OH$, CHO, $CO_2H$, $CO_2R_{12}$, $C(O)R_{12}$, or substituted $C_1$-$C_6$ alkyl;
- $R_{11}$ is H, OMe, $NH_2$, $NO_2$, NOH, $C_1$-$C_6$ alkyl, optionally substituted with alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol, or a 1-20 atom linker bound to rosaramicin; and
- $R_{12}$ is $C_1$-$C_6$ alkyl, optionally substituted with alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol, or a pharmaceutically acceptable salt thereof.

For example, disclosed are compounds having the structure:

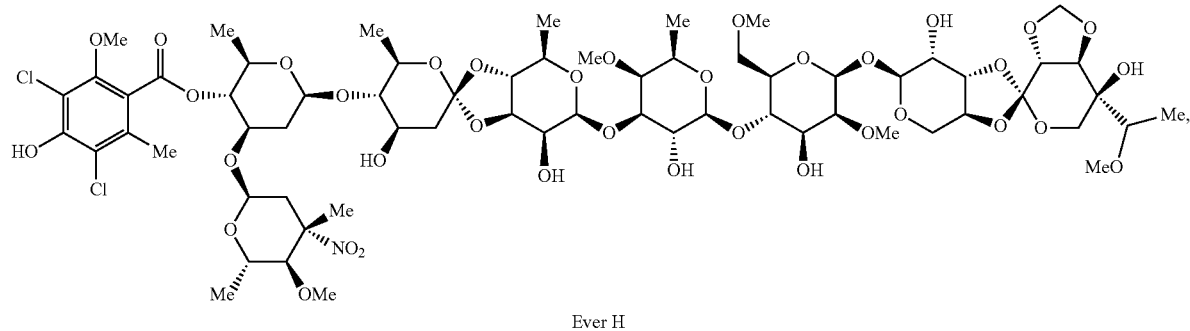

Ever H (11)

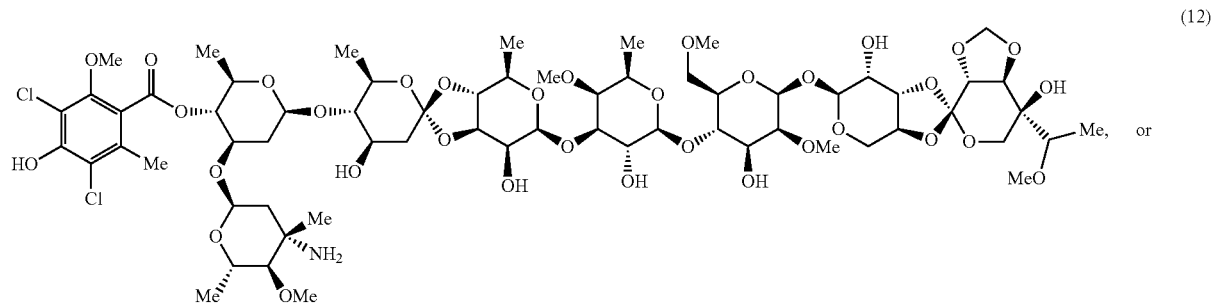

Ever J (12)

or (13)

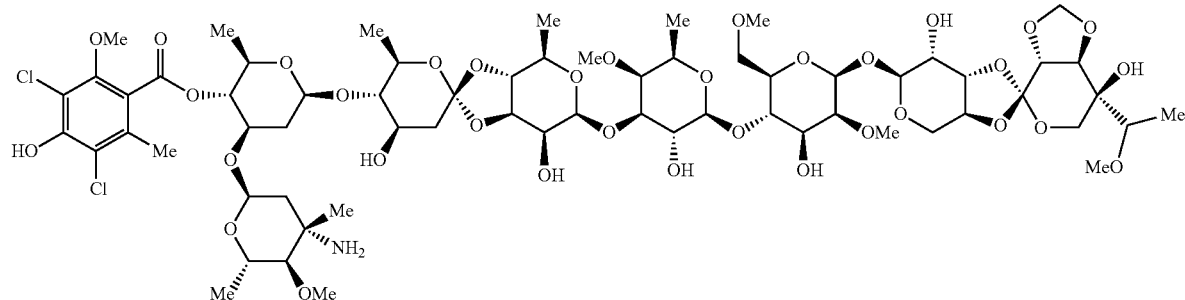

Ever K or a pharmaceutically acceptable salt thereof.

Also disclosed are compound having the structure:

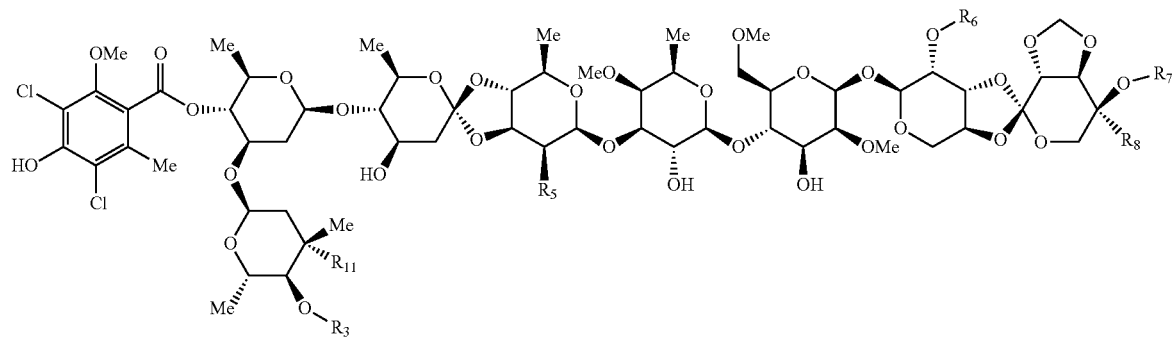

wherein
- $R_3$ and $R_5$ are each, individually, H, OH, $OCH_3$, $CH_2OH$, CHO, $CO_2H$, $CO_2R_{12}$, $C(O)R_{12}$, or substituted $C_1$-$C_6$ alkyl;
- $R_6$ is H, OH, $OCH_3$, $CH_2OH$, CHO, $CO_2H$, $CO_2R_{12}$, $C(O)R_{12}$, substituted $C_1$-$C_6$ alkyl; or orsellinyl;
- $R_7$ is H, OH, $OCH_3$, $CH_2OH$, CHO, $CO_2H$, $CO_2R_{12}$, $C(O)R_{12}$, or substituted $C_1$-$C_6$ alkyl;
- $R_8$ is OH, $OCH_3$, $CH_2OH$, CHO, $CO_2H$, $CO_2R_{12}$, $C(O)R_{12}$, or substituted $C_1$-$C_6$ alkyl;
- $R_{11}$ is H, OMe, $NH_2$, $NO_2$, NOH, $C_1$-$C_6$ alkyl, optionally substituted with alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol, or a 1-20 atom linker bound to rosaramicin; and
- $R_{12}$ is $C_1$-$C_6$ alkyl, optionally substituted with alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol, or a pharmaceutically acceptable salt thereof.

Specific examples include the following structures:

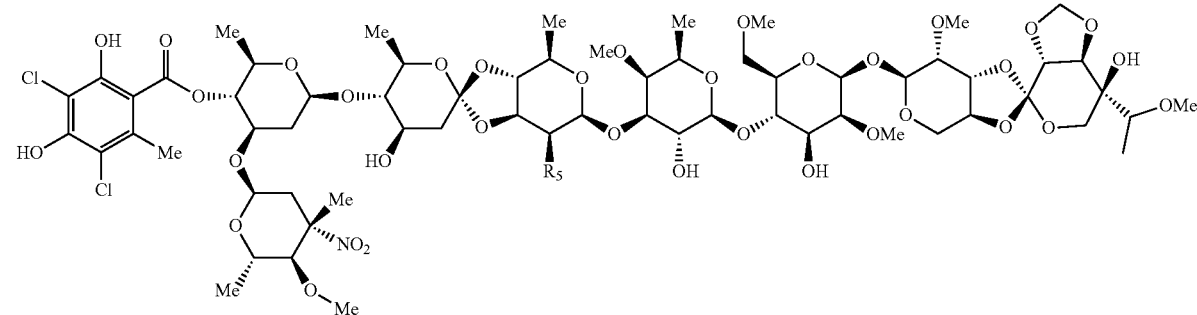

des-methyl Ever-D

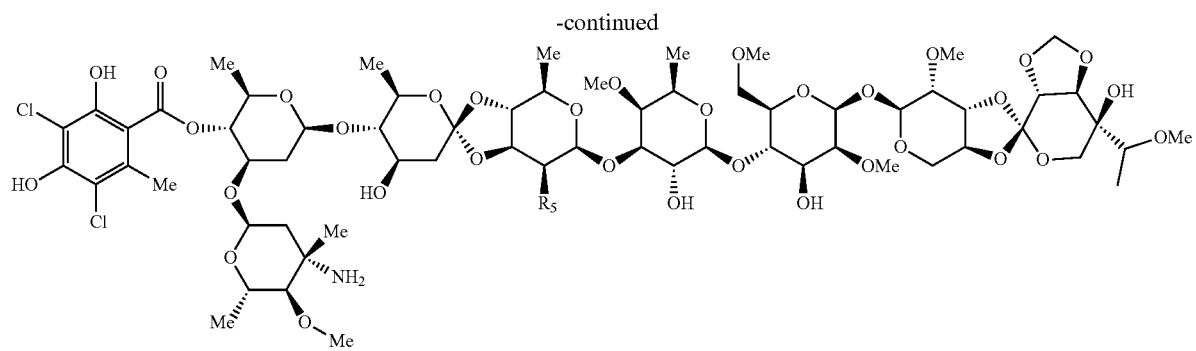

des-methyl Ever E

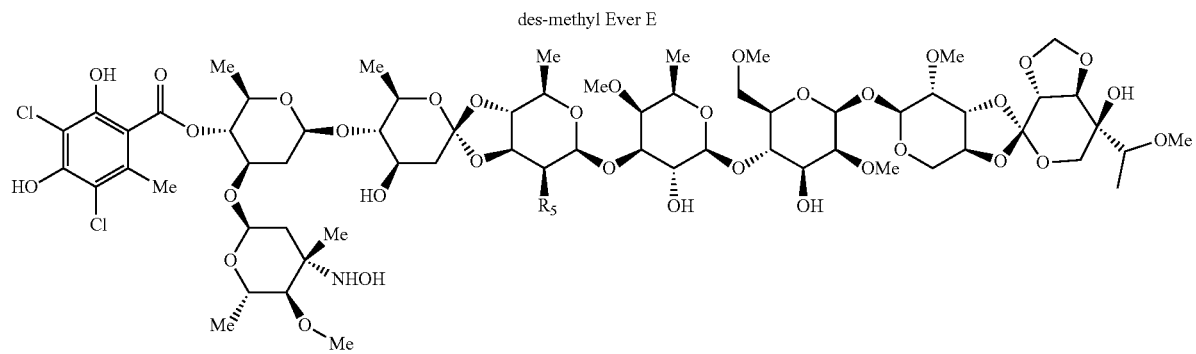

des-methyl Ever-F

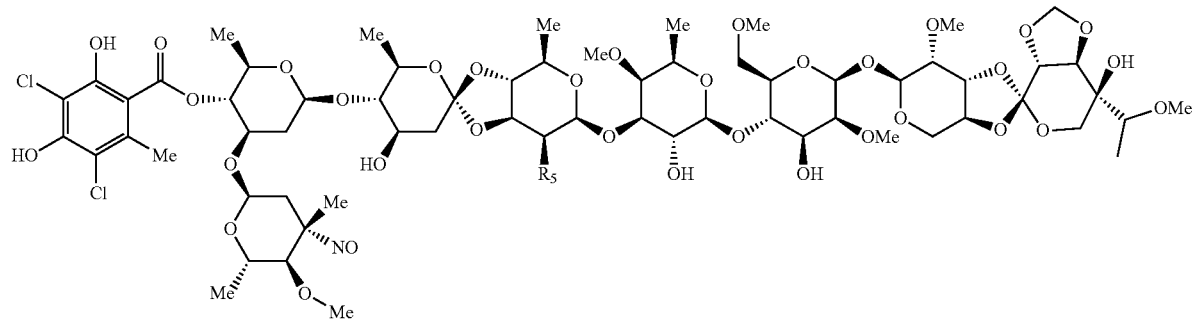

des-methyl Ever G and pharmaceutically salts thereof.

Also disclosed are compounds having the following structure:

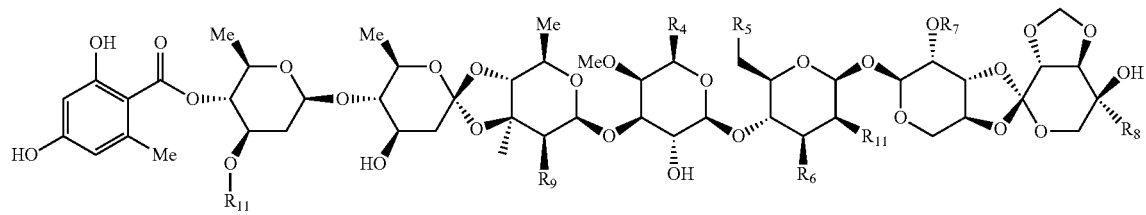

wherein $R_4$-$R_6$ are each, individually, H, OH, $OCH_3$, $CH_2OH$, CHO, $CO_2H$, $CO_2R_{12}$, $C(O)R_{12}$, or substituted $C_1$-$C_6$ alkyl;

$R_7$ is H, $CH_3$, $CH_2OH$, $C(O)R_{12}$, substituted $C_1$-$C_6$ alkyl; or orsellinyl;

$R_8$ is H, OH, $OCH_3$, $CH_2OH$, CHO, $CO_2H$, $CO_2R_{12}$, $C(O)R_{12}$, or substituted $C_1$-$C_6$ alkyl;

$R_9$ is H, OH, $OCH_3$, $CH_2OH$, CHO, $CO_2H$, $CO_2R_{12}$, $C(O)R_{12}$, or substituted $C_1$-$C_6$ alkyl;

$R_{11}$ is H, OMe, $C_1$-$C_6$ alkyl, optionally substituted with alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol, or a 1-20 atom linker bound to rosaramicin; and $R_{12}$ is $C_1$-$C_6$ alkyl, optionally substituted with alkyl, alkoxy, alkenyl, alkynyl, aryl, heteroaryl, aldehyde, amino, azido, carboxylic acid, cyano, ester, ether, halide, hydroxy, ketone, nitro, silyl, sulfo-oxo, sulfonyl, sulfone, sulfoxide, or thiol, or a pharmaceutically acceptable salt thereof.

Specific examples of these compounds are:

$R_7$ is H, OH, $OCH_3$, $CH_2OH$, CHO, $CO_2H$, $CO_2R_{12}$, $C(O)R_{12}$, or substituted $C_1$-$C_6$ alkyl;

$R_8$ is OH, $OCH_3$, $CH_2OH$, CHO, $CO_2H$, $CO_2R_{12}$, $C(O)R_{12}$, or substituted $C_1$-$C_6$ alkyl; and $R_{12}$ is $C_1$-$C_6$ alkyl, optionally substituted with alkyl, alkoxy, alkenyl, alkynyl, aryl, heteroaryl, aldehyde, amino, azido,

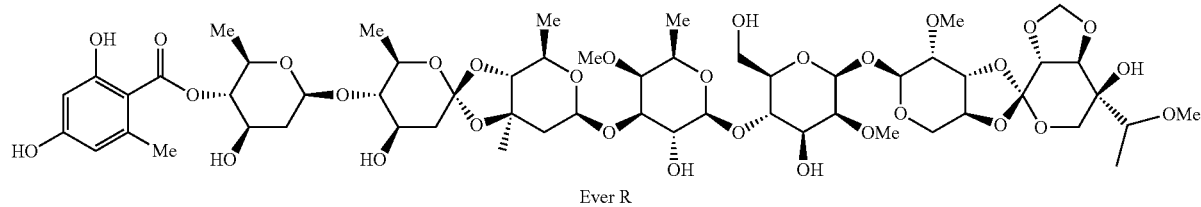
Ever R

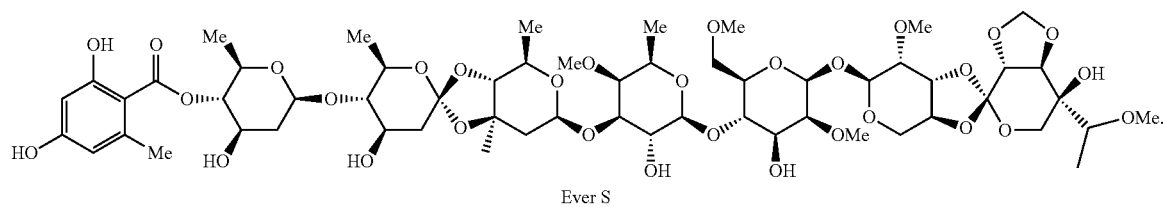
Ever S

Also disclosed are compounds having the structure:

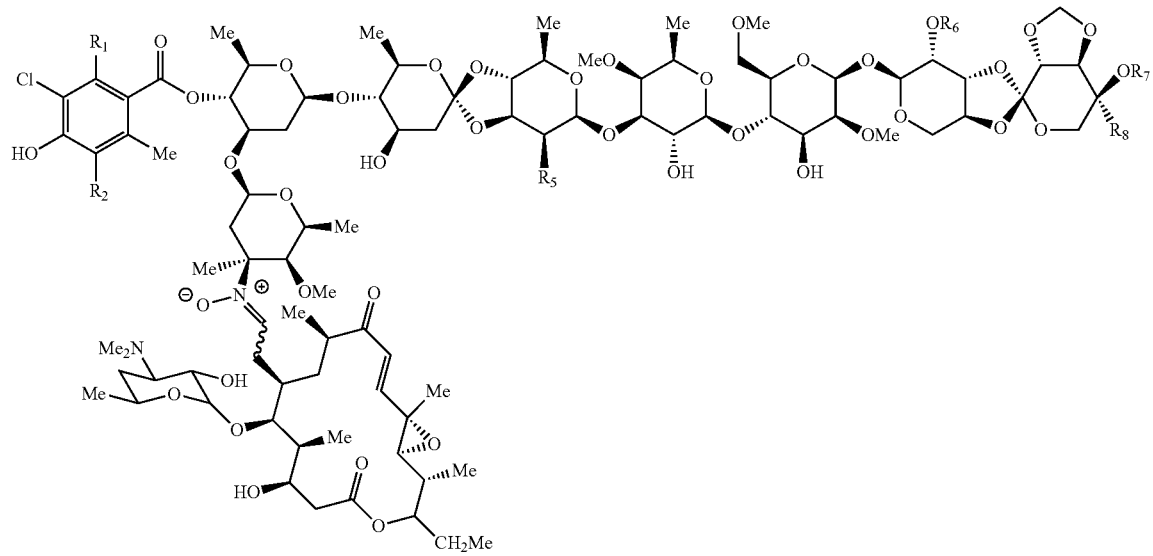

wherein
$R_1$, $R_3$ and $R_5$ are each, individually, H, OH, $OCH_3$, $CH_2OH$, CHO, $CO_2H$, $CO_2R_{12}$, $C(O)R_{12}$, or substituted C1-C6 alkyl;

$R_2$ is H or Cl;

$R_6$ is H, OH, $OCH_3$, $CH_2OH$, CHO, $CO_2H$, $CO_2R_{12}$, $C(O)R_{12}$, substituted $C_1$-$C_6$ alkyl; or orsellinyl;

carboxylic acid, cyano, ester, ether, halide, hydroxy, ketone, nitro, silyl, sulfo-oxo, sulfonyl, sulfone, sulfoxide, or thiol, or a pharmaceutically acceptable salt thereof.

For example, disclosed are compounds having the following structure:

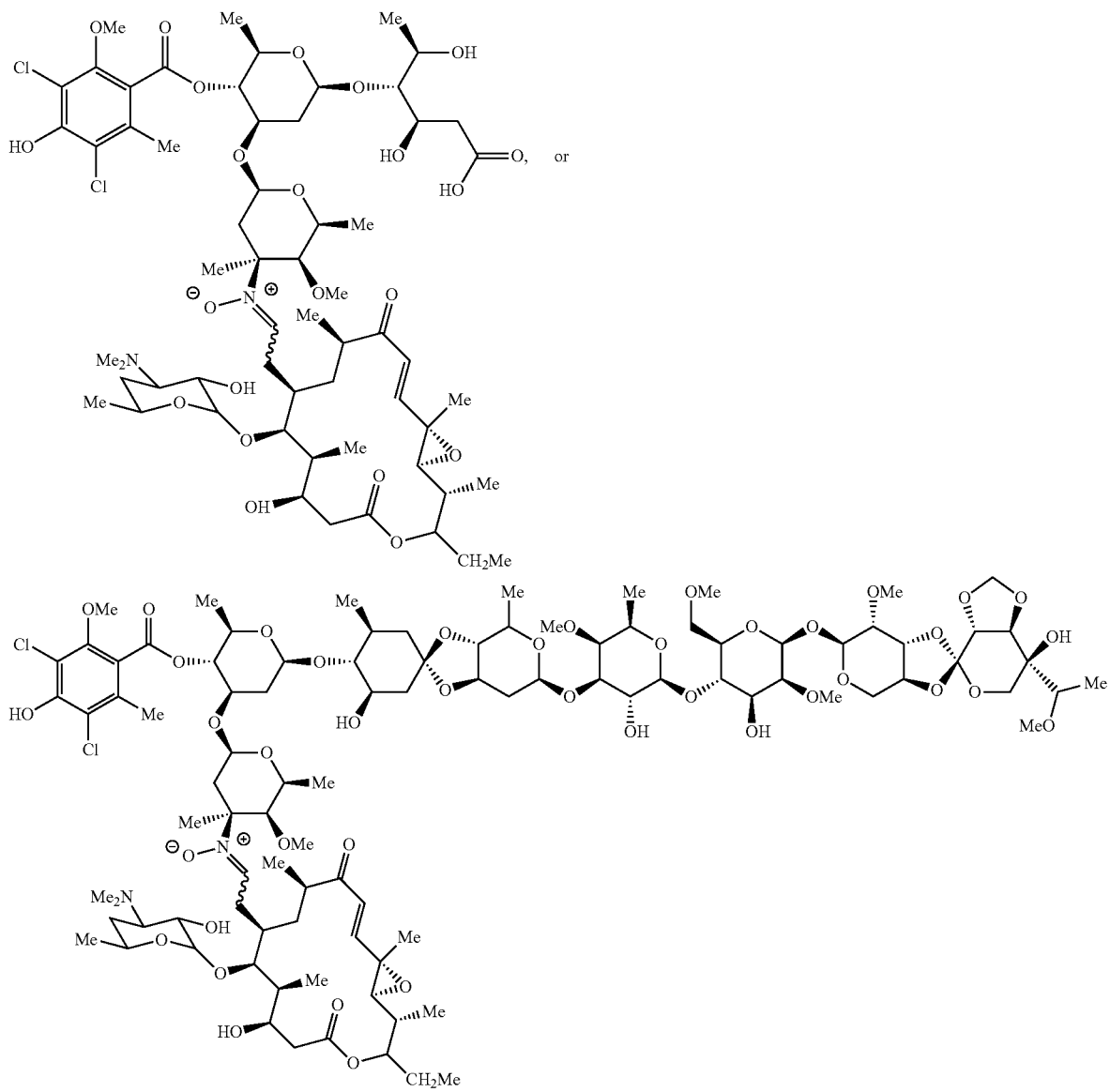

or a pharmaceutically acceptable salt thereof. Also disclosed are, individually, the cis nitrone and the trans nitrone structures.

In specific examples of the disclosed compounds $R_1$ is $OCH_3$. In other examples $R_1$ is Cl. In other specific examples of the disclosed compounds $R_2$ is Cl. In still further examples, $R_3$ is H, $CH_3$, or Cl. In still other examples, $R_4$ is $NO_2$, $NH_3$, $CH_2OH$, $CH_3$. In other examples, $R_5H$, OH, or $OCH_3$. In other examples, R6 is H, CH3, or OCH3. In further examples, $R_7$ is h, Cl, $COCH_3$, $COC_2H_9$, or a ketone. In other examples, $R_8$ is H or $COCH_3$.

Methods of Making

The chemical synthesis of orthosomycins is complex and requires over 100 steps. Thus, disclosed herein is an alternative to chemical synthesis of analogs whereby the biosynthetic pathway responsible for production of everninomicins is altered. By deleting, adding, or modifying enzymes in the pathway, new analogs can be created. Here translated sequence similarities were used to deduce the function of each enzyme in the everninomicin biosynthetic pathway from *M. carbonacea* var *aurantiaca*. Additionally, two additional orthosomycin gene clusters, eve and ava, were annotated to provide a fuller picture of orthosomycin biosynthesis. Targeted gene replacement of 3 genes from the everninomicin pathway in *M. carbonacea* var *aurantiaca* provided the first functional assessment of this gene cluster and resulted in the accumulation of 5 new everninomicin congeners. By providing information about the mutability of the gene cluster as well as tolerance of the biosynthetic enzymes for non-natural substrates, the work presented here provides a method for constructing everninomicin analogs with improved efficacy and pharmacological properties through manipulation of the biosynthetic pathway.

The avilamycin A biosynthetic gene cluster from *Streptomyces viridochromogenes* Tü57 was first reported in 1997. Inactivation of two genes confirmed the role of this cluster in avilamycin biosynthesis. This large cluster appears to contain 4 glycosyltransferases, 22 sugar synthesis and tailoring genes, 2 genes for orsellinic acid biosynthesis, 1 halogenase, 3 oxygenases, 5 genes involved in regulation and transport, and 2 genes responsible for avilamycin resistance (FIG. 4).

Four genes from the avilamycin cluster have been implicated in dichloroisoeverninic acid biosynthesis. AviM is responsible for orsellinic acid synthesis while AviN may control the starter unit. Inactivation of aviG4 resulted in loss of a methyl group from dichloroisoeverninic acid confirming it as an O-methyltransferase. Additionally, inactivation of the halogenase aviH resulted in an avilamycin analog lacking the two chlorine atoms of ring A.

The exact function of the remaining three O-methyltransferases was determined by gene inactivation. AviG2 methylates the C6 oxygen of ring F, AviG5 is responsible for O-methylation of ring E, and AviG6 methylates the C2 hydroxyl of ring F (Scheme 1, B). Bechthold and coworkers generated double and triple mutant combinations of these methyltransferases to produce an array of avilamycin analogs termed gavibamycins. Disruption of the gene encoding the putative C-methyltransferase, AviG1, resulted in abolished avilamycin production. However, complementation of a C-methyltransferase eryBIII mutant with aviG1 from the erythromycin pathway in *Saccharopolyspora erythraea* resulted in restored erythromycin production. This experiment confirmed the role of AviG1 as a C-methyltransferase likely involved in the synthesis of ring D.

Scheme 1: Orthosomycin biosynthesis

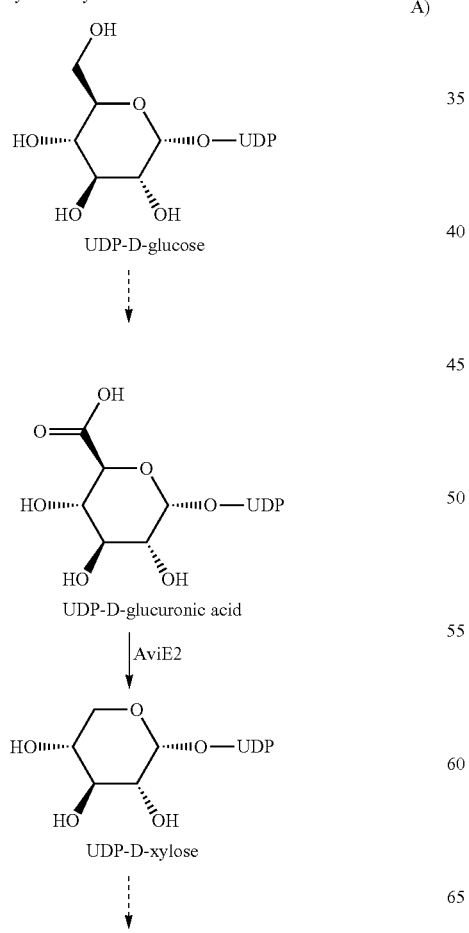

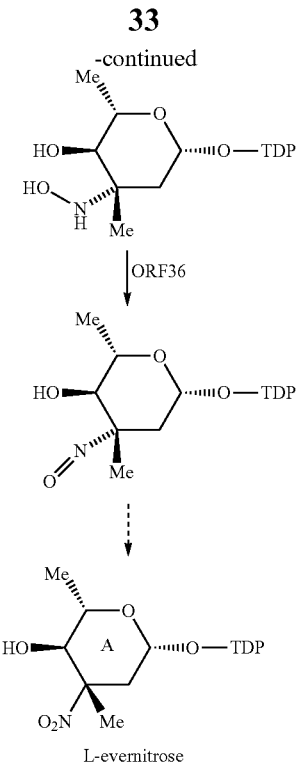

L-evernitrose

In Scheme 1, column A is a proposed scheme for formation of ring G, L-lyxose. AviE2 has been shown to catalyze the decarboxylation of UDP-D-glucuronic acid to UDP-D-xylose. In column B, is a scheme formation of 2,6-di-O-methyl-D-mannose from 6-O-methyl-D-glucose. AviX12 catalyzes a unique radical epimerization. In column C is a scheme showing the formation of L-evernitrose from L-epi-vancosamine. ORF36 catalyzes the oxidation of the nitrogen from the amino to the nitroso oxidation state. It is likely spontaneous oxidation of the nitroso congener which leads to the nitro form.

In vitro characterization of AviE2 revealed that it is a UDP-D-glucuronic acid decarboxylase involved in conversion of UDP-D-glucuronic acid to UDP-D-xylose. This results indicate that the pentose L-lyxose is originally derived from UDP-D-glucose. Two additional epimerization steps are necessary to convert D-xylose to L-lyxose (Scheme 1, A). The authors hypothesize that aviQ1, aviQ2, or aviQ3 may encode the necessary chemistries for these epimerizations. This is the first description of a UDP-glucuronic acid decarboxylase involved in secondary metabolism.

Inactivation of aviX12 resulted in formation of an avilamycin analog containing D-glucose rather than D-mannose (ring F) which possess different stereochemistries at C2. Additionally the C2 hydroxyl was not methylated suggesting that epimerization precedes methylation of this position. As mentioned above, epimerization of the hydroxyl at C2 results in complete loss of antibiotic activity. Therefore, AviX12 is necessary for formation of an active avilamycin. However, this epimerization is notable as it takes place at an unactivated carbon (Scheme 1, B). Upon characterization of its [Fe—S] cluster, AviX12 was determined to be a member of the radical AdoMet family, and AviX12 appears to be the first reported member of the radical AdoMet family involved in epimerization of a sugar.

Gene inactivation experiments suggest that AviO2 and AviB1 are involved in eurekanate biosynthesis. Loss of aviO2 and aviB1 resulted in an avilamycin derivative proposed to have lost the acetyl residue at position C4 of ring H. It was hypothesized that AviB1 and AviB2 are part of an incomplete pyruvate decarboxylase complex that catalyzes the conversion of pyruvate to an acetyl carbanion which is subsequently attached to the saccharide chain through the action of AviO2.

However, it has been previously proposed that AviO1, AviO2, and AviO3 were oxidases involved in orthoester and methylenedioxy bridge formation. Their original analysis of the avilamycin gene cluster found that these three genes had homology to non-heme iron, α-ketoglutarate dependent oxidases which are not likely involved in deoxysugar biosynthesis. Inactivation of aviO1 and aviO3 resulted in abolished production although, as detailed above, inactivation of aviO2 resulted in a putative de-acetylated avilamycin analog. These results are curious in light of inspection of the everninomicin gene clusters from *M. carbonacea* var *africana* (GenBank accession number AX195929) (FIG. 4) and *M. carbonacea* var *aurantiaca* (GenBank accession numbers AX574200-2). Although everninomicin contains orsellinic acid attached to eurekanate rather than an acetyl group, its gene cluster still contains a close homolog of aviO2. Based on translated sequence similarities, putative functions for the genes have been proposed (see FIG. 4). Additionally all known class I orthosomycins gene clusters contain three oxidases with striking homology to the three from the avi cluster. The class II orthosomycin hygromycin B gene cluster also contains a putative non-heme iron, α-ketoglutarate dependent oxidase, HygX. Based on this evidence, the family of α-ketoglutarate dependent oxidases is believed to be responsible for orthoester and methylenedioxy bridge formation.

Gene inactivation of aviGT4 resulted in an avilamycin derivative which lacked the terminal eurekanate moiety. Interestingly, eurekanate is attached to the saccharide chain via an orthoester linkage in all orthosomycins. The lack of this linkage suggests that either AviGT4 alone is responsible for orthoester formation or, more likely, glycosylation precedes orthoester formation.

The eveminomicin gene cluster from *M. carbonacea* var *africana* ATCC39149 was reported in 2001. Insertional inactivation of everJ, everF, and everW resulted in abolished everninomicin production confirming the role of this gene cluster in everninomicin biosynthesis. Although few biosynthetic studies of the everninomicin gene cluster have been reported, the nitrososynthase ORF36 from *M. carbonacea* var *africana* has been well characterized. Analysis of two everninomicin gene clusters and two avilamycin gene clusters accompanied by subtractive analysis identified a cassette of genes involved in L-evernitrose formation (FIG. 4, genes N1-M7). Of particular interest is ORF36 (N1) a flavin-dependent monooxygenase which has been shown to oxidize the amino sugar L-TDP-epi-vancosamine to the nitroso form (Scheme 1, C). Fermentation under aphotic conditions also results in accumulation of the nitroso compound indicating that full oxidation to the nitro may not be enzymatically catalyzed. A five-enzyme in vitro pathway was constructed to test the catalytic competence of ORF36. ORF36 was able to convert TDP-L-epi-vancosamine progenitors to the hydroxylamine oxidation state. $^{18}O_2$ labelling experiments revealed that molecular oxygen is incorporated into the hydroxylamine and nitroso products. Additionally, an X-ray crystal structure of ORF36 was solved revealing a tetrameric enzyme with a fold similar to that of class D flavin-containing monooxygenases. The structure also revealed an unusually open active site which may explain their promiscuity. Inactivation of aviP, a putative phosphatase, did not influence avilamycin production. However, inactivation of aviD, aviO1, aviO3, aviE2, aviG1, everJ, everF, and everW resulted in abolished orthosomycin production.

Each cluster contains a putative glucose-1-phophate thymidyltransferase (EvdS4, EveS1, and AvaS2) responsible for formation of dTDP-glucose, a proposed precursor for all sugar residues. After formation of dTDP-glucose, a variety of enzymes are necessary to produce the deoxy- and dideoxysugars of the orthosomycins. In each of the eveminomicin clusters, there are two putative 4,6 dehydratases (EvdS5, Evd10, EveS2, and EveS6) and one 2,3-dehydratase (EvdS9 and EveS7). In the avilamycin cluster, there are three putative 4,6-dehydratases (AvaS3, AvaS5, and AvaS8) and one 2,3-dehydratase (AvaS9). These dehydratases in the ava pathway correspond to the number and type of dehydratases proposed for the avi cluster. Each eveminomicin cluster contains 5 putative epimerases (EvdS2, EvdS3, EvdS6, EvdS11, EvdS13, EveS3, EveS5, EveS10, EveS11, and EveS13). The ava cluster only contains 4 putative epimerases (AvaS1, AvaS4, AvaS6, and AvaS7) as it lacks the epimerase needed for formation of evernitrose. Based on homology to AviX12 in the avilamycin pathway, functions of EvdS2 (71% identity), EveS5 (79% identity), and AvaS6 (96% identity) were assigned as epimerases, which act on the C-2 position of ring F. Additionally, in each of the everninomicin clusters, there are four genes which encode putative ketoreductases (evdS1, evdS7, evdS8, evdS14, eveS4, eveS8, eveS9, and eveS14). However, only two genes encoding putative ketoreductases were found in the ava cluster (avaS10 and avaS11). This is in contrast to the avi cluster which putatively encodes 4 ketoreductases. Due the large number of deoxysugars present in everninomicin and avilamycin, it is difficult to propose exact functions for each enzyme.

For formation of the dichloroisoeverninic acid moiety, a polyketide synthase, an acyltransferase, a halogenase, and an O-methyl transferase are necessary. Based on translated sequence similarities, evdD3, eveD1, and avaD2 encode polyketide transferases. EvdD1, EveD2, and AvaD1 are putative acyltransferases. Notably, in the eve, ava, and avi gene clusters, the acyltransferase directly precedes the polyketide synthase, while in the evd gene cluster they are separated by 16 genes. EvdD2, EveD3, and AvaD3 are putative halogenases with homology to AviH (78, 72, and 92% identities respectively) which has been shown to chlorinate isoeveminic acid. Finally, evdM5, eveM8, and avaM6 encode putative aromatic O-methyltransferases. These genes have high homology to aviG4 (60, 61, and 87% identities respectively), which has been shown to methylate the ortho position of dichloroisoeverninic acid.

Unlike the other sugar residues, the genes responsible for evernitrose formation are clustered together at the end of the everninomicin gene clusters. Notably, no homologs of these genes are found in the pathways for avilamycin production which does not contain evernitrose. Previous work has shown that EveN1 (also known as ORF36) is responsible for oxidation of the amine to the nitroso. Consequently, the homolog in the evd cluster evdN1 is also proposed to be a nitrososynthase. EvdM8 and eveM6 appear to encode C-3-methyltransferases (both have 71% identity to kijD1). Based on sequence similarity to the O-methyltransferase from the rubradirin pathway, RubN7, EvdM9 (61% identity) and eveM7 (61% identity) encode O-methyltransferases responsible for methylating the C-3-OH of evernitrose. Other enzymes proposed to be involved in evernitrose biosynthesis include the 3-aminotransferase (EvdS12 and EveS12), a 3,5-epimerase (EvdS13 and Eve S 13), and a 4-ketoreductase (EvdS14 and EveS14).

Interestingly, the number of glycosyltransferases in each cluster does not correspond directly to the number of glycosidic linkages. Each everninomicin and avilamycin contain two more glycosidic linkages than the number of glycosyltransferases. In each of the eveminomicin pathways, 5 putative glycosyltransferases (EvdGT1, EvdGT2, EvdGT3, EvdGT4, EvdGT5, EveGT1, EveGT2, EveGT3, EveGT4, and EveGT5) were identified. There were four putative glycosyltransferases in the ava cluster (AvaGT1, AvaGT2, AvaGT3, and AvaGT4) corresponding to four proposed glycosyltransferases in the avi cluster. Based on homology to AviGT4, a glycosyltransferase characterized from the avilamycin pathway, EvdGT1, EveGT3, and AvaGT4 are responsible for glycosidic attachment of ring H. The fact the number of glycosyltransferase does not correlated directly with the number of sugar linkages suggests that some glycosyltransferases act iteratively or that another type of enzyme is responsible for both glycosidic linkage and orthoester linkage formation. A conserved family of oxygenases has been identified in each pathway (EvdO1, EvdO2, EvdMO1, EveO1, EveO2, EveO3, AvaO1, AvaO2, and AvaO3). Their role in the formation of the orthoester linkages and methylenedioxy bridges of the orthosomycins is be discussed herein.

Genes Involved in Tailoring

The orthosomycins are highly decorated oligosaccharides which require a large number of tailoring enzymes. The evd cluster putatively encodes 8 O-methyltransferases (evdM1, evdM2, evdM4, evdM5, evdM6, evdM7, evdM9, and evdMO1) and 2 C-methyltransferases (evdM3 and evdM8). Notably, evdMO1 appears to be a fusion of an O-methyltransferase and an oxygenase. The eve cluster putatively encodes 6 O-methyltransferases (eveM1, eveM2, eveM3, eveM4, eveM7, and eveM8) and 2 C-methyltransferases (eveM5 and eveM6). Generation of fully decorated eveminomicin requires 9 methylation events. The evd cluster contains one additional methyltransferase which could be responsible for alternative everninomicin analogs. Notably, the evd cluster and eve cluster have been shown to produce different everninomicin analogs, and this explains the variation in the number of methyltransferases found in each cluster. The ava cluster putatively encodes 5 O-methyltransferases (avaM2, avaM3, avaM4, avaM5, and avaM6) and 1 C-methyltransferase (avaM1). This corresponds to number and types of methyltransferases predicted in the avi gene cluster. Each avilamycin gene cluster appears to contain one extra methyltransferase than the number of required methylation events for formation of avilamycin A.

Figure 13:
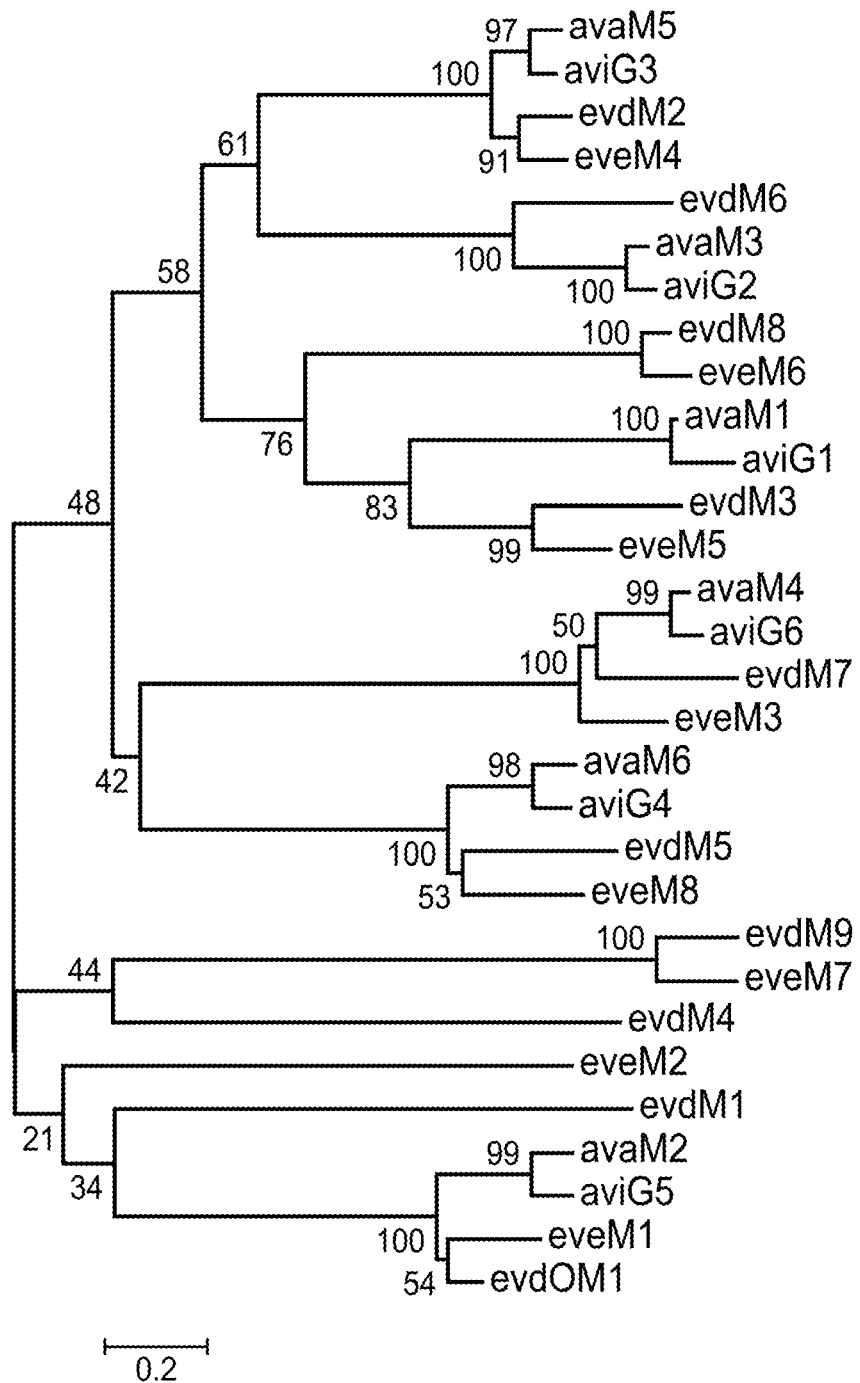
FIG. 13 is a phylogenetic analysis of methyltransferases from four class I orthosomycin gene clusters, evd, eve, ava, and avi.

Based on phylogenetic analysis of methyltransferases from the four class I orthosomycin gene clusters, evd, eve, ava, and avi, the studies of the avi cluster were extrapolated to putatively assign the function of seven classes of methyltransferases (FIG. 13). For the sake of simplicity, this section will focus on the putative function of the methyltransferases from the evd cluster. EvdM3 is homologous to aviG1 (45% identity) from the avilamycin pathway which encodes a C-methyltransferase responsible for methylating the C-3 of the D ring. As discussed previously, evdM5 is homologous to aviG4 and is proposed to methylate the hydroxyl of dichloroisoeverninic acid. EvdM6 is homologous (57% identity) to aviG2 which has been shown to methylate the C-6 hydroxyl of the F ring. EvdM7 shares 66% sequence identity with AviG6 which has been shown to methylate the C-2 hydroxyl of the F ring. As discussed herein, evdM8 and evdM9 are responsible for methylation of evernitrose. Finally, evdMO1 encodes a C-terminal O-methyltransferase with homology to aviG5, the product of which has been shown to methylate the C-4 hydroxyl of the E ring of avilamycin.

Genes Involved in Regulation and Resistance.

Resistance genes are commonly clustered with biosynthetic genes for bacterial secondary metabolites. Indeed, in the orthosomycin pathways, there are several genes which appear to be involved in resistance. In the evd pathway, evdX1, evdX2, and evdX2 appear to encode RNA methyltransferases. In the eve pathway, evdX1 and eveX2 appear to encode RNA methyltransferases. In the ava pathway, avaX1 and avaX2 have homology to aviRb and aviRa respectively. AviRa and AviRb have been shown to methylate 23S rRNA and confer resistance to avilamycin. Additional, the ava pathway encodes two putative ABC transporters, AVAX3 and AvaX4.

The evd cluster putatively encodes 3 regulators, EvdR1, EvdR2, and EvdR3. Interestingly, the eve cluster only appears to encode one regulator, EveR1. The ava cluster putatively encodes two regulators, AvaR1 and AvaR2, which have homology to AviC1 and AviC2 in the avilamycin pathway. AviC1 and AviC2 have been shown to be transcriptional activators of the avilamycin pathway in *S. viridochromogenes* Tü57.

Construction of Gene Replacement Mutants

In the disclosed methods, everninomicins are produced from *M. carbonacea* var *aurantiaca*. Alteration of production parameters results in a drastic increase in production levels and allowed for the identification of new everninomicin congeners each varying in the N-oxidation state of the nitro sugar. Additionally, unusual everninomicin-rosaramicin conjugates were identified which retained potency against *Staphylococcus aureus*. To investigate the biosynthesis of everninomicins, methods were developed for the genetic manipulation of *M. carbonacea* and for facile analysis of everninomicin analogs.

A classical conjugation method for *Streptomyces* developed by Bierman and Mazodier did not produce *M. carbonacea* transformants, thus a new method was developed and disclosed herein. For the conjugal transfer of DNA into actinomycetes, *Escherichia coli* is commonly used as the donor bacterium. As many actinomycetes are methyl-restricting, DNA is passaged through a non-methylating strain, *E. coli* 12567, prior to transfer. Vectors containing oriT can then be mobilized into *M. carbonacea* by *E. coli* 12567 containing the non-transmissible plasmid pUZ8002. *E. coli* 12567/pUZ8002 was employed as the donor strain but modified other parameters of the Bierman protocol including temperature, mode of selection, and preparation of recipient *M. carbonacea* strains. Additionally, as no suitable vector was available for genetic complementation of gene replacements, so a new vector system was designed and implemented for the successful transformation of *M. carbonacea*.

Further, a modified protocol for genetic manipulation of *M. carbonacea* was used to produce transformants. Modifications to the preparation of recipient bacterium, method of exconjugant isolation, and incubation temperature resulted in much higher conjugation efficiencies. Development of a membrane-washer assembly now allows for quick isolation of exconjugants. Previously, low concentrations of nalidixic acid were used to stunt the growth of the donor *E. coli*. Isolation of colonies using these conditions was tedious and required multiple steps to obtain pure *M. carbonacea* colonies with *E. coli* frequently overtaking the slower-growing *M. carbonacea* colonies. A membrane allows the mycelia of *M. carbonacea* to penetrate beneath to the agar while the larger *E. coli* are trapped on top of membrane. Removal of the membrane after the appropriate incubation time reveals colonies which do not have to be further separated from *E. coli*. The washer-membrane assembly greatly simplifies the isolation procedure and reduces the time it takes to obtain pure exconjugants.

In specific examples, disclosed herein are methods for producing an everninomicin congener that comprise culturing in a fermentor a *Micromonospora carbonacea* var. *aurantiaca* bacterium in a production medium to thereby produce a fermentation culture; obtaining from the fermentation culture an extract containing the everninomicin congener; and isolating and purifying the everninomicin congener from the fermentation culture extract. These methods can be used to produce everninomicin congers comprising a everninomicin conjugated to a rosaramicin, such as compounds 8 and 9 disclosed herein.

In specific examples, disclosed herein are methods for producing an everninomicin congener that comprise culturing in a fermentor a *Micromonospora carbonacea* bacterium in a production medium to thereby produce a fermentation culture, wherein the bacterium has altered or deleted O-methyltransferase, C-methyltransferase, and/or nitrososynthase activity; obtaining from the fermentation culture an extract containing the everninomicin congener; and isolating and purifying the everninomicin congener from the fermentation culture extract. In certain examples, the bacterium can comprise one or more mutations in a gene of the evd gene cluster. In other examples, the bacterium can comprise one or more mutations in a gene selected from the group consisting of evdM2, evdM3, evdN1, and evdO1. In still other examples, bacterium can comprise *Micromonospora carbonacea* var. *aurantiaca*.

Also disclosed are methods of transforming *Micromonospora*, comprising contacting one side of a membrane with a conjugation composition comprising a donor bacterium and a recipient *Micromonospora* bacterium, wherein them membrane is able to be penetrated by *Micromonospora* mycelia but not the donor bacterium; incubating the composition for a time and temperature sufficient to grow colonies of *Micromonospora* which penetrate the membrane; and removing the membrane and donor bacterium, thereby leaving the transformed *Micromonospora*. In certain examples, the donor bacterium is *E. coli*. In other examples wherein the recipient *Micromonospora* is *M. carbonacea*. In still other examples wherein the *M. carbonacera* is *M. carbonacera* var *aurantiaca*. In further examples wherein the membrane forms the bottom of a container, which holds the conjugation composition. In certain examples, the transformed *Micromonospora* can comprise one or more mutations in a gene of the evd gene cluster. In certain examples the transformed *Micromonospora* can comprise one or more mutations in a gene selected from the group consisting of evdM2, evdM3, evdN1, and evdO1.

Further, disclosed are methods of culturing *Micromonospora*, comprising: incubating *Micromonospora* at from 28 to 34° C. for from 8 to 12 days in a media comprising less than 2% lactose and at least 2% glucose. For example, incubating can be at 30° C. In other examples, incubating can be for 10 days. In certain examples, the media can comprise 3% or more glucose and substantially no lactose.

Figure 14:
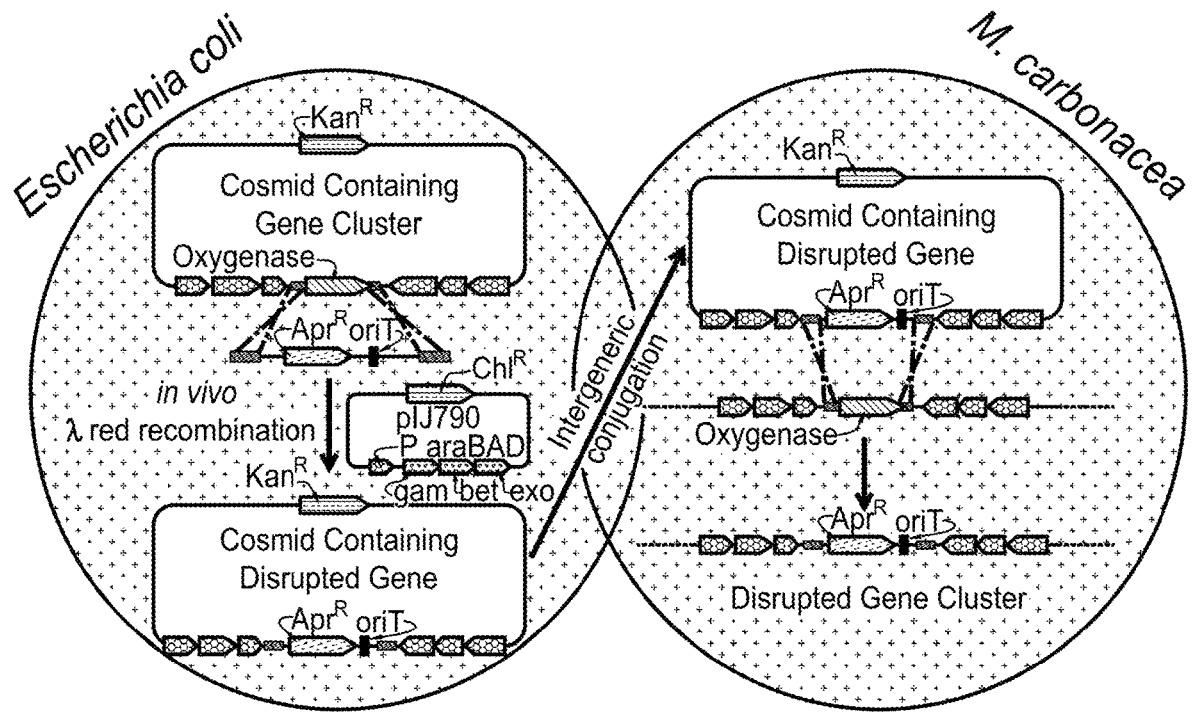
FIG. 14 is a scheme for two step targeted gene disruptions.

For the first time, the evd cluster was experimentally verified to be responsible for biosynthesis of everninomicin by construction of gene replacements in *M. carbonacea* var *aurantiaca*. Targeted gene replacements of evdN1, evdM3, and evdM2 were accomplished using a two-step PCR targeting strategy (FIG. 14). The gene replacements were first prepared on a cosmid in *E. coli* using λ-Red recombination. The cassette, encoding apramycin resistance and an origin of transfer, was designed with 39 base pair extensions that have homology to regions flanking the target gene. Induction of the three genes of the λ-Red recombination system (gam, bet, and exo) stimulated homologous recombination between the PCR-generated linear cassette and the cosmid containing the gene of interest in *E. coli* to generate the desired gene replacement. Gene replacements were confirmed by PCR amplification of the cassette and sequencing.

Due to the methylation sensitivity of actinomycetes, the cosmid was then transformed via electroporation into ET12567, a non-methylating strain of *E. coli* containing plasmid pUZ8002 which is responsible for transmission of the cosmid during conjugation. The de-methylated cosmid was subsequently transformed into *M. carbonacea* var *aurantiaca* by conjugation with a donor *E. coli* strain harboring a cosmid with the desired gene replacement. As discussed herein, a new method for isolating exconjugants was developed. This method used a 0.4 μm membrane which the mycelia of *M. carbonacea* could penetrate while the donor *E. coli* remained trapped beneath.

Figure 15:
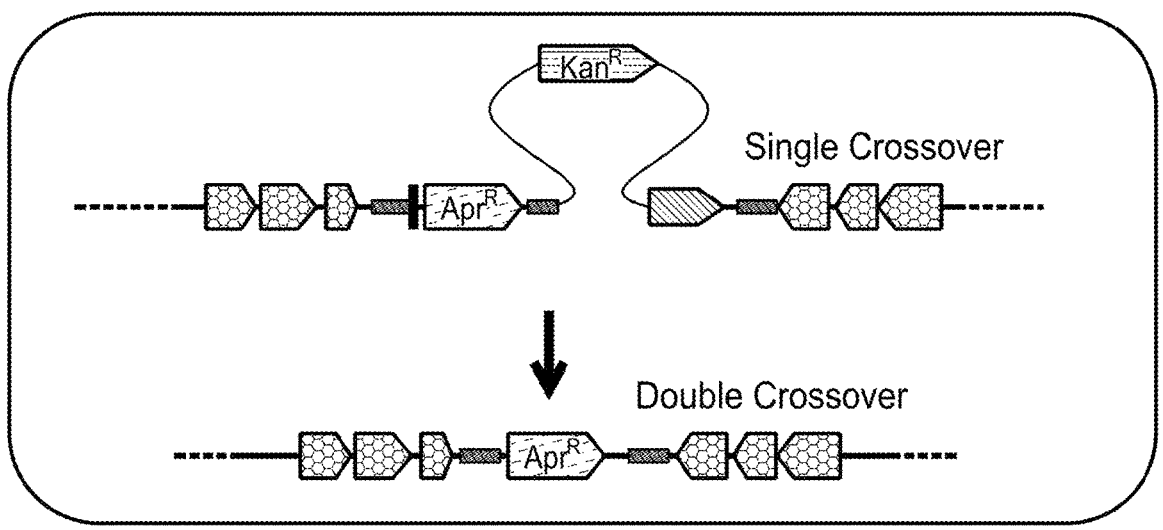
FIG. 15 is a depiction of a single crossover versus a double crossover replacement.
Figure 16:
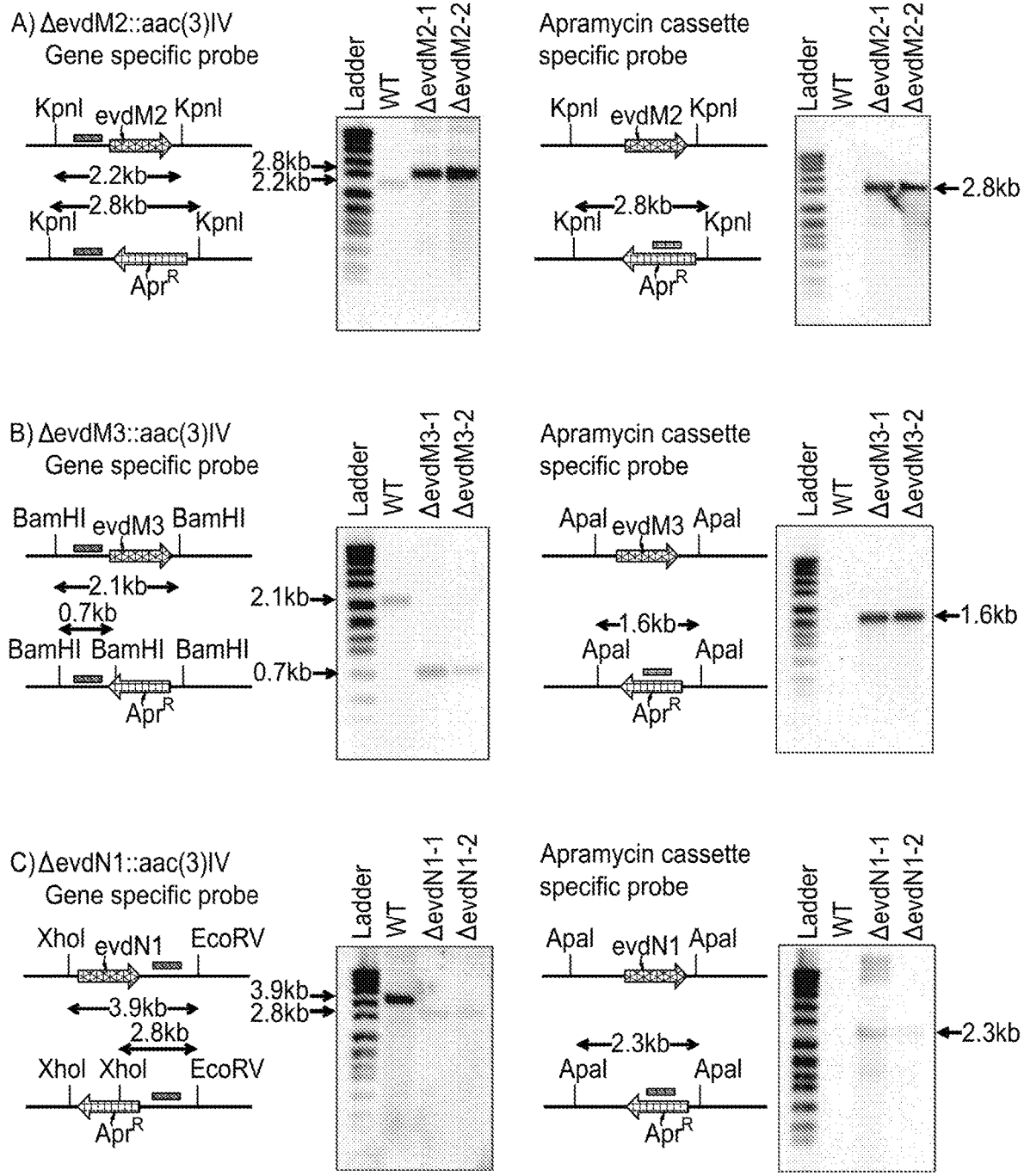
FIG. 16 shows the results from Southern hybridization of targeted replacement mutants verifying a double crossover event. All blots show predicted shifts were observed experimentally, thus confirming the double crossovers. Panel A shows the Southern blot analysis of ΔevdM2::aac(3)IV. Diagrams depict the relative shifts expected for replacement of evdM2 with the apramycin cassette. Panel B shows the Southern blot analysis of ΔevdM3::aac(3)IV. Diagrams depict the relative shifts expected for replacement of evdM3 with the apramycin cassette. Panel C shows the Southern blot analysis of ΔevdN1::aac(3)IV. Diagrams depict the relative shifts for replacement of evdN1 with the apramycin cassette. Ladder is DNA molecular weight marker VII, DIG-labeled (product no. 11669940910; Roche Life Sciences). WT is wild-type *M. carbonacea* var *aurantiaca*. ApaI, KpnI, BamHI, XhoI, and EcoRV are restriction.

Upon transformation of the cosmid into *M. carbonacea*, two rounds of homologous recombination must take place to generate a double crossover mutant (FIG. 15). The first recombination event yielded a single crossover where the entire cosmid was incorporated into the gene cluster. The insertion of such a large amount of DNA in a gene cluster can lead to polar effects and disruption of the entire gene cluster. Therefore, a double crossover generated by a second round of recombination was desirable. To select for double crossover mutants, exconjugants which were apramycin resistant and kanamycin sensitive were chosen for further analysis. These mutant strains were then analyzed via PCR amplification of the apramycin and kanamycin resistance genes to verify the double-crossover. Using this method of verification, evdN1, evdM1, and evdM2 appeared to have been successfully disrupted in *M. carbonacea* var *aurantiaca*. However, as PCR cannot verify the genomic position of the crossover, a Southern blot analysis was used to confirm the replacement mutants (FIG. 16). Digoxigenin (DIG) probes were designed upstream of each putative gene replacement. Genomic DNA from wildtype *M. carbonacea* and each mutant stain was isolated and digested with appropriate endonucleases to give predictably sized fragments. Blots were analyzed for specific shift of probe-labeled fragments for wildtype *M. carbonacea* and each mutant strain. Gene replacements were confirmed for evdN1, evdM3 and evdM2 as predictable band shifts were observed (FIG. 16).

To assess the effect of the three gene replacements on everninomicin production, tandem liquid chromatography mass spectral (LC/MS) analysis of the crude extracts of mutant strains was employed. Analysis of LC/MS data revealed abolished production of everninomicins D-G in all three gene replacement strains. These results provide the first experimental confirmation of the everninomicin gene cluster in *M. carbonacea* var *aurantiaca*.

Role of evdN1 in Everninomicin Biosynthesis

The nitrososynthase, ORF36, of the *M. carbonacea* var *africana* everninomicin gene cluster was previously characterized in vitro. Biochemical characterization revealed that ORF36 catalyzes the double oxidation of the amino sugar of everninomicin E to the corresponding nitroso sugar of everninomicin G. In order to characterize the nitrososynthase in vivo, evdN1 was replaced with the apramycin cassette to generate ΔevdN1::aac(3)IV. Analysis of extracts of this mutant revealed loss of production of full length everninomicins D-G (1-4), but accumulation of everninomicin-2 (5) which lacked the nitrosugar. Of note, the everninomicin-rosaramicin conjugates (6 and 7) were no longer formed due to loss of the hydroxylamino functionality. The structure of Ever-2 was confirmed by mass spectrometric fragmentation (FIG. 3). Genetic complementation did not result in restored production of wild type everninomicins indicating that, although the replacement was precise, polar effects caused loss of activity of downstream genes. Examination of the everninomicin gene cluster revealed that the genes for biosynthesis of the nitrosugar cluster in one operon with evdN1 at the beginning of the operon. Because of polar effects from the gene replacement of the nitrososynthase, complete functional loss of the nitro sugar operon and therefore the A-ring was observed.

Role of evdM3 in Everninomicin Biosynthesis

As stated previously, evdM3 was proposed to encode a C-3methyltransferase with homology to AviG1 from the avilamycin pathway in *S. viridochromogenes* Tü57. Previous in vitro work with AviG1 has shown that it is a C-methyltransferase which can complement the activity of EryBIII, a C-3-methyltransferase involved in L-mycarose biosynthesis in the erythromycin pathway. When AviG1 was deleted in the avilamycin producer, *S. viridochromogenes* the Bechthold group reported abolished production of all avilamycins.[15] However, when evdM3 was inactivated in *M. carbonacea*, three new metabolites accumulated which are termed everninomicins H, J, and K (FIG. 3).

Everninomicin H is the major metabolite in this mutant strain and its structure was determined by NMR and confirmed by mass spectrometric fragmentation. Structure determination of minor metabolites Ever J and Ever K was accomplished using high-resolution mass spectrometric fragmentation (FIG. 3). Each of these metabolites lacked the C-3 methyl of the D-ring as well as the O-methyl on C-2 of the G-ring. Additionally, a hydroxyl was added to the C-2 position of the D-ring. A hydroxyl in this position has been identified in other everninomicins but was not identified in previous everninomicins produced by *M. carbonacea* var *aurantiaca*. Downstream of evdM3 is evdM4 which has homology to O-methyltransferases. Likely, polar effects from gene replacement of evdM3 caused loss of function of evdM4 in turn resulting in loss of the O-methyl on the G-ring. Intriguingly, Ever K gained a methyl on the F-ring which has not been observed before in the everninomicins.

Genetic complementation with evdM3 resulted in production of a metabolite which is termed Ever L (10) that had a mass corresponding to addition of a methyl group. Unfortunately, low production levels of Ever L precluded precise structural assignment. However as this metabolite only appeared after complementation with the C-methyltransferase evdM3, it is likely that complementation restored the C-methyl of the D ring. These results are consistent with the predicted function of evdM3 as a C-3 methyltransferase and with polar effects causing loss of function of evdM4 that are not restored with genetic complementation of evdM3.

Excitingly, everninomicin H maintained activity against *S. aureus* subsp. *aureus* Rosenbach with an MIC of 16 μg/mL. Although everninomcin H is less potent than everninomicin A (Ziracin™, MIC=1 μg/mL), it is still moderately active against *S. aureus*, and can provide important information about the structure-activity relationship of the everninomicins.

Role of evdM2 in Everninomicin Biosynthesis

Based on translated sequence similarities, evdM2 encodes a sugar O-methyltransferase. To determine the function of this putative methyltransferase, the gene replacement ΔevdM2::aac(3)IV was constructed. Upon analysis of the mutant's extracts, no desmethyl analogs were identified. However, the truncated everninomicin-rosaramicin conjugate (6) was detected. Unfortunately, genetic complementation with evdM2 did not restore the production of any additional metabolites. Although the exact function for EvdM2 is uncertain, sequence similarities and the gene replacement data presented here indicate that EvdM2 installs an O-methyl on the eastern side of the molecule, likely the methylene of the methylenedioxy bridge.

Mutability of the Everninomicin Gene Cluster

Targeted gene replacement of evdN1, evdM3, and evdM2 confirmed the role of the evd gene cluster in everninomicin biosynthesis as everninomicins D-G were not produced by these mutants. Furthermore, 5 new everninomicin analogs were generated and the role of evdM3 as a C-3 methyltransferase responsible for methylating the C-3 position of the D ring of everninomicin was assigned. Notably, polar effects drastically effected downstream genes and resulted in accumulation of unexpected metabolites.

Analysis of the gene replacement mutants revealed that when the first gene in an operon is replaced with the cassette, disruptive polar effects cause loss of function of the entire operon. In the case of ΔevdN1::aac(3)IV, replacement of evdN1, which encodes a nitrososynthase, resulted in loss of the evernitrose entirely. As evidenced by the fact that everninomicins of various N-oxidation states are produced by the wild type strain, full oxidation of the sugar is not required for glycosylation. Thus, replacement of the nitrososynthase should have yielded the amino sugar. However, as evdN1 is at the first gene in an operon which encodes the enzymes necessary for evernitrose formation, it is likely that polar effects from the gene replacement disrupted many downstream genes and resulted in abolished production of evernitrose.

Additionally, analysis of the ΔevdM2::aac(3)IV mutant revealed loss of the entire eastern portion of the molecule. This result is curious as evdM2 is proposed to encode an O-methyltransferase, and loss of evdM2 would be expected to result in a desmethyl compound. However, evdM2 is also the first gene in an operon which encodes two additional methyltransferases, a glycosyltransferase, and a gene of unknown function. Replacement of evdM2 with the cassette caused polar effects which resulted in loss of function of downstream genes leading to altered everninomicin production.

Replacement of evdM3 resulted in the production of three new metabolites, everninomicins H, J, and K. Notably, all of these metabolites are lacking the C-3 methyl of the D ring which is consistent with the proposed function of EvdM3. However, additional modifications were observed, such as hydroxylation of C-2 of the D-ring and loss of the O-methyl from C-2 of the G ring. Intriguingly, the C-3 hydroxyl of the F ring was methylated which has never before been observed in everninomicins. Inspection of the genomic surroundings of evdM3 provided some insight into one of these unexpected changes. As evdM3 was not the first gene in the operon, its replacement did not result in entire loss of the operon as replacement of evdM2 or evdN1 did. However, directly downstream of evdM3 is another methyltransferase, evdM4. EvdM4 is proposed to be an O-methyltransferase but has no homology to genes in the avilamycin pathways. As the new metabolites are lacking an O-methyl on the G ring and this same position has a different decoration in the avilamycins, it is likely that polar effects resulted in the loss of function of evdM4, and that EvdM4 is responsible for methylation of the C-2 hydroxyl of the G ring.

The metabolites produced by the gene replacement mutants provided helpful information about the tolerance of everninomicin biosynthetic enzymes toward unnatural substrates. Most intriguingly, despite the loss of the methyl group at C-3 of the D ring, the orthoester linkage between the C and D rings was still formed. This result is evidence that the orthoestersynthase can tolerate large changes to its substrate as the loss of a methyl group directly at the site of modification did not affect its enzymatic capabilities. Additionally, other changes to the structure, such as the loss of the O-methyl of the G ring, addition of the O-methyl on the F ring, and loss of evernitrose, were also well tolerated by the glycosyltransferases and other biosynthetic machinery as the structure was still fully assembled and elaborated.

Analysis of the structures can also provide information about timing of orthosomycin biosynthesis. Specifically, as Ever-2 is a fully elaborated heptasaccharide lacking only evernitrose, this nitrosugar must be the last sugar residue to be attached to the oligosaccharide chain. Additionally, the 1,1-linkage between rings F and G must be assembled first to provide the appropriate glycosyl acceptor for addition of subsequent sugar residues. After coupling of the F and G rings, the chain would then be assembled from this bidirectional glycosyl acceptor terminating with addition of evernitrose.

Role of Oxygenases from Orthosomycin Clusters

Using translated sequence similarities, 13 open reading frames were identified from five orthosomycin gene clusters which putatively encode non-heme iron, α-ketoglutarate dependent oxygenases among the five orthosomycin gene clusters. The number of putative oxygenases directly correlates with how many anticipated oxidative cyclizations are required for orthoester linkage and methylenedioxy bridge formation in each orthosomycin. The everninomicin and avilamycin gene clusters each contain three of these oxygenases which correspond to the two orthoester linkages and the methylenedioxy bridge found in each molecule. Conversely, only one of these putative oxygenases was found in the biosynthetic cluster for hygromycin B which only contains one orthoester linkage. Furthermore, these are the only enzymes within each gene cluster that appear to have sufficient catalytic capacity for these oxidations.

Figure 17:
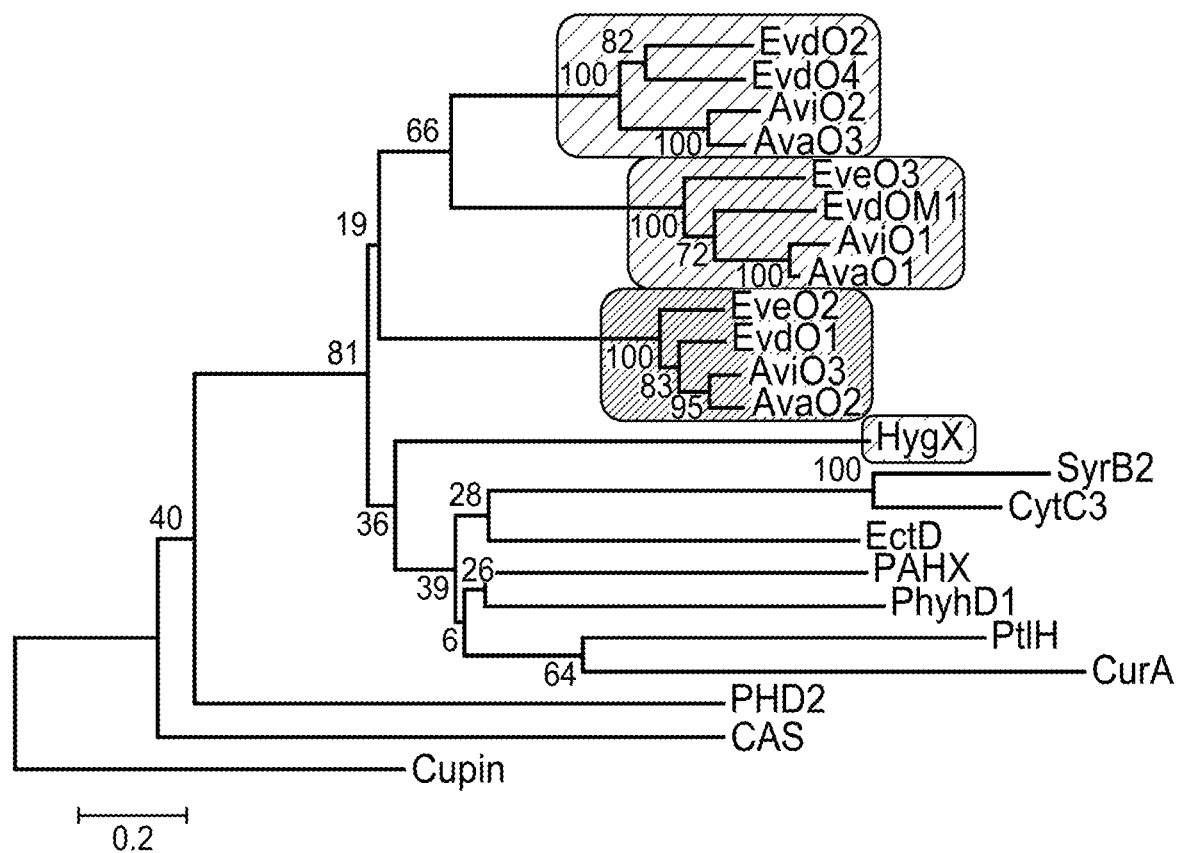
FIG. 17 shows a phylogenetic analysis of orthosomycin-associated oxygenases. Analysis was conducted using MEGA 5 as described in the methods section. Class I orthosomycin-associated oxygenases formed three distinct group with each group containing one oxygenase from each pathway. The Class II-associated oxygenase, HygX, did not cluster with the others oxygenases.

Phylogenetic analysis of the thirteen orthosomycin-associated oxygenases form a distinct subfamily of non-heme iron, α-ketoglutarate dependent oxygenases most closely related to the phytanoyl-CoA 2-hydroxylase (PhyH) subfamily (FIG. 17). The PhyH subfamily encodes enzymes with varying enzymatic capabilities including halogenations, dioxygenations, and hydroxylations. The orthosomycin-associated oxygenase subfamily can be further separated into subgroups. Three subgroups contain one oxygenase from each of the avilamycin and everninomicin gene clusters. The fourth subgroup contains only HygX from the hygromycin gene cluster. Sequence identity between enzymes of different subgroups is 22-43% which is consistent with a related mechanism but different substrates. Enzymes belonging to the same subgroup have much higher sequence identities of 65-93%. This high sequence identity suggests that oxygenases within subgroups catalyze the same reaction on closely related substrates. Sequence identities can be found in Table 3.

TABLE 3

Comparison of sequence identities (% identity) among the 13 orthosomycin-associated oxygenases.

|        | EvdO1 | EveO2 | AvaO2 | AviO3 | EvdO2 | EveO3 | AvaO3 | AviO2 | EvdMO1 | EveO1 | AviO1 | AvaO1 | HygX |
|--------|-------|-------|-------|-------|-------|-------|-------|-------|--------|-------|-------|-------|------|
| EvdO1  | —     | 70    | 73    | 73    | 26    | 24    | 24    | 23    | 26     | 30    | 28    | 28    | 24   |
| EveO2  | 70    | —     | 73    | 75    | 23    | 26    | 23    | 22    | 24     | 27    | 30    | 30    | 24   |
| AvaO2  | 73    | 73    | —     | 89    | 26    | 23    | 25    | 25    | 24     | 25    | 29    | 29    | 25   |
| AviO3  | 73    | 75    | 89    | —     | 24    | 35    | 43    | 27    | 23     | 25    | 29    | 30    | 23   |
| EvdO2  | 26    | 23    | 26    | 24    | —     | 71    | 66    | 66    | 29     | 30    | 29    | 30    | 36   |
| EveO3  | 24    | 26    | 23    | 35    | 71    | —     | 69    | 69    | 31     | 29    | 31    | 30    | 29   |
| AvaO3  | 24    | 23    | 25    | 43    | 66    | 69    | —     | 88    | 30     | 30    | 31    | 30    | 28   |
| AviO2  | 23    | 22    | 25    | 27    | 66    | 69    | 88    | —     | 32     | 36    | 32    | 32    | 28   |
| EvdMO1 | 26    | 24    | 24    | 23    | 29    | 31    | 30    | 32    | —      | 73    | 74    | 72    | 29   |
| EveO3  | 30    | 27    | 25    | 25    | 30    | 29    | 30    | 36    | 73     | —     | 66    | 65    | 28   |
| AviO1  | 28    | 30    | 29    | 29    | 29    | 31    | 31    | 32    | 74     | 66    | —     | 93    | 32   |
| AvaO1  | 28    | 30    | 29    | 30    | 30    | 30    | 30    | 32    | 72     | 65    | 93    | —     | 35   |
| HygX   | 24    | 24    | 25    | 23    | 36    | 29    | 28    | 28    | 29     | 28    | 32    | 35    | —    |

Oxygenase Requirement for Everninomicin Biosynthesis

In order to determine the role of the putative oxygenases in orthosomycin biosynthesis, gene replacements of evdO1, evdO2, and evdMO1 were created from the everninomicin pathway in *M. carbonacea* var *aurantiaca*. Targeted gene replacements of evdO1, evdO2, and evMO1 were accomplished using a two-step PCR targeting strategy described herein. To select for double crossover mutants, exconjugants which were apramycin resistant and kanamycin sensitive were chosen for further analysis. These mutant strains were then analyzed via PCR amplification of the apramycin and kanamycin resistance genes to verify the double-crossover. Using this method of verification, evdO1, evdO2, and evdMO1 appeared to have been successfully disrupted in *M. carbonacea* var *aurantiaca*.

However, as PCR cannot verify the position of the crossover, Southern blot analysis was used to confirm the replacement mutants (FIG. 18). Digoxigenin (DIG) probes were designed upstream of each putative gene replacement. Genomic DNA from wildtype and each mutant strain was isolated and digested with appropriate endonucleases to give predictably sized fragments. Blots were analyzed for specific shifts of probe-labeled fragments for wildtype *M. carbonacea* and each mutant strain. Gene replacements were confirmed for evdO1 and evdMO1 predictable band shifts were observed. However, although PCR analysis suggested that evdO2 had been successfully replaced, Southern blot analysis revealed that replacement of evdO2 in fact was not successful as the predicted band shifts were not observed. Likely the apramycin cassette was integrated into a different region of the genome. Further efforts to generate an evdO2 replacement were unsuccessful. This results underscores the importance of thoroughly analyzing each mutant strain by not only PCR but also Southern blot analysis.

To assess the effect of the oxygenase gene replacements on everninomicin production, tandem liquid chromatography mass spectral (LC/MS) analysis of the crude extracts of mutant strains was employed. Analysis of LC/MS data revealed abolished production of everninomicins D-G in both evdO1 and evdMO1 gene replacement strains (FIG. 4). Consistent with the Southern blot analysis of the evdO2 mutant strains, everninomicin production was not affected in any of these mutants. These results confirm that evdO1 and evdMO1 are indeed involved in everninomicin biosynthesis and constitutes the first confirmation of the everninomicin gene cluster in *M. carbonacea* var *aurantiaca*.

Genetic Complementation of ΔevdO1::Aac(3)IV and ΔevdMO1::Aac(3)IV Strains

To determine if polar effects were influencing everninomicin production in the gene replacements, ΔevdO1::aac(3)IV and ΔevdMO1::aac(3)IV were genetically complemented to generate strains: ΔevdO1::aac(3)IV_GC and ΔevdMO1::aac(3)IV_GC. In the case of ΔevdMO1::aac(3)IV_GC, eveminomicin production was not restored by genetic complementation. This result was consistent with polar effects causing disruption of other critical genes in the gene cluster leading to abolished production. However in the case of ΔevdO1::aac(3)IV_GC, while genetic complementation did not restore production of eveminomicins D-G, intriguingly, production of the truncated eveminomicin-rosaramicin conjugate was observed. Although this conjugate is a degradation product of a larger metabolite, the C-1 position of ring C is consistent with the oxidation state of an orthoester linkage. Given that this conjugate was not observed in ΔevdO1::aac(3)IV, this data is highly suggestive that evdO1 is responsible for forming the orthoester linkage between the C and D rings.

Structural Characterization of Orthosomycin-Related Oxygenases

To further understand the role of these oxygenases in orthosomycin biosynthesis, crystal structures were determined for a representative oxygenase from each of the phylogenetic subgroups (AviO1, EvdO1, EvdO2, and HygX). Each enzyme adopted a double stranded β-helix motif with the active site housing a metallocenter between β-sheets containing antiparallel β-strands. Although the fold was conserved among these enzymes, the oligomerization state varied, with AviO1 and EvdO2 as monomers, EvdO1 as a dimer, and HygX as a tetramer. Consistent with our sequence analysis, structural similarity searches revealed that the orthosomycin-associated oxygenases are related to the PhyH subfamily of non-heme iron, α-ketoglutarate dependent oxygenases.

Previous research has suggested that loop insertions between the β-strands of the double stranded β-helix of non-heme iron, α-ketoglutarate dependent oxygenases control substrate specificity. Indeed, all of the oxygenases characterized here contain loop inserts to form large binding clefts. Notably, all loop insertions have high crystallographic temperature factors which are commonly interpreted as a metric of flexibility. This flexibility is suggestive of substrate binding loops that change conformation upon substrate binding. Consistent with this proposal, upon α-ketoglutarate binding to HygX, comparison of the loops of the four protomers showed that the loops moved nearly 20 Å to promote active site closure.

In the majority of non-heme iron, α-ketoglutarate dependent oxygenases, iron coordination in the active site involves two histidines and one acidic residue to form a conserved H-X-D/E . . . H motif known as the facial triad. Although the crystal structures described here contained catalytically inactive $Ni^{2+}$ rather than $Fe^{2+}$ in the active site, it was verified that $Ni^{2+}$ retained the octahedral coordination geometry typical of $Fe^{2+}$ coordination in the orthosomycin-associated oxygenases. Whereas, AviO1, EvdO1, and EvdO2 retained the canonical facial triad, HygX contained a variation where the acidic residue was substituted with a glycine and a glutamic acid located four residues before the distal histidine completes the metal coordination sphere to form a novel H-X-G . . . E-$X_3$-H motif. As expected, costructures of the oxygenases with α-ketoglutarate or succinate revealed that α-ketoglutarate binds directly to the metal with the 2-keto group trans to the acidic ligand.

Unfortunately, the substrates for the orthosomycin-associated oxygenases are not known and synthesis of a library of possible substrates is impractical. However, as enzymes have affinity for their products, binding of hygromycin B to HygX was measured using tryptophan fluorescence quenching ($K_d$=3.4±0.5 μM). This low-micromolar affinity is consistent with affinities observed between enzymes and their products and suggests that HygX catalyzes the last step in hygromycin B biosynthesis. The costructure of HygX was determined with α-ketoglutarate and hygromycin B to 1.6-Å resolution. Unambiguous electron density for hygromycin B showed one of the bridging oxygens of the orthoester approaching the metal center. The binding was highly specific with the position stabilized by 10 direct and 5 water-mediated interactions. Hygromycin B was oriented with the anomeric carbon of destomic acid 5.2 Å from the metal, close enough for oxygenation of the anomeric carbon. Interestingly, structural comparison of the HygX-hygromycin B costructure with EvdO1, EvdO2, and AviO1 structures shows that the hygromycin B ligand geometry would result in a steric clash if HygX retained the canonical facial triad. Because EvdO1, EvdO2, and AviO1 likely catalyze the same chemical reaction as HygX, the facial triad was most likely modified for substrate accommodation. The fact that HygX was able to bind hygromycin B in a chemically productive orientation for oxygenation of the anomeric carbon is highly suggestive that this family of enzymes forms the orthoester linkages of the orthosomycins.

Method of Use

The compounds disclosed herein can be used to treat infections and inhibit the growth of bacteria. In certain examples, disclosed are methods of treating an infection in a patient, comprising administering to the patient a therapeutically effective amount of any of the compounds disclosed herein. Specific examples of infections that can be treated include, but are not limited to, leprosy bacteria, Mycobacteria, *Neisseria*, tuberculosis bacteria, actinomycetes, Corynebacteria, *Listeria*, clostridia, bacilli, enterococci, Bortedellen, pseudomonads, *Helicobacter, Haemophilus*, vibrios, *Shigella, Yersinia*, and *Salmonella*.

Examples include the following diseases include: tuberculosis; Pneumonia; Typhoid; Paratyphoid; Syphilis, Gastritis; Gastroenteritis; Ruhr; Pestilence; Enteritis; extraintestinal infections, peritonitis and appendicitis with *E. coli* and intestinal infections with EHEC, EPEC, ETEC and EIEC; Cholera, Legionnaires' disease, whooping cough, brucellosis, Lyme disease, leptospirosis, typhus, trachoma, gonorrhea, meningitis, septicemia, leprosy etc.

A further subject of the disclosed methods is the treatment of infectious diseases involving, in particular of *Staphylococcus aureus*, in a human or animal by administering a compound disclosed herein to the human or animal.

In other examples, disclosed herein are methods of treating an infection in a patient, comprising administering to the patient a therapeutically effective amount of any of the modified organisms disclosed herein. These organisms can be administered neat, or in lyophilized form, or in a suspension. The organisms can act as a probiotic and be administered with other probiodiotics and/or nutritional supplements.

In these disclosed methods, one can treat humans with infections, but also can treat livestock (horses, cows, pigs, sheep, goats etc.), poultry, and companion animals (dogs, cats, rabbits, etc.). The compositions or organisms can be administered alone or in combination with other therapeutics or nutritional supplements, for example the composition can be combined into a feed.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

E. coli strains were grown in LB broth. M. carbonacea var aurantiaca NRRL 2997 and replacement mutants were grown on TSB (Tryptone Soy Broth) agar and in TSB liquid. Intergeneric conjugations were performed on solid AS1 media (0.1% yeast extract, 0.5% soluble starch, 0.02% L-alanine, 0.02% L-arginine, 0.05% L-asparagine, 0.25% NaCl, 1% Na2SO4, 2% agarose at pH 7.5, supplemented with 10 mM $MgCl_2$). Apramycin (50 µg/mL), nalidixic acid (25 µg/mL), chloramphenicol (30 µg/mL), and kanamycin (50 µg/mL) were used when required for selection as described below.

Production of Everninomicins from M. carbonacea Var Aurantiaca

Seed cultures were generated by inoculating a loop of mycelia from TSB agar into 100 mL of 2997 Germination Medium (0.3% beef extract, 0.5% tryptose, 0.1% dextrose, 2.4% soluble starch, 0.5% yeast extract, and 0.1% calcium carbonate) for 5 days at 30° C. in a 500 mL Erlenmeyer flask with shaking. For everninomicin production, 25 mL of the seed culture was added to 500 mL Production Medium (0.5% yeast extract, 0.1% corn steep solids, 0.1% calcium carbonate, 3% glucose) in a 2 L baffled Fernbach flask and grown with shaking at 30° C. for 10 days. Diaion HP-20 resin (100 mL, previously pre-equilibrated with methanol and washed with water) was added to the fermentation cultures and incubated for 60 minutes with shaking. The combined resin and mycelia were collected by centrifugation at 3000×g, extracted successively with 250 mL methanol and 250 mL acetone, and evaporated to dryness by rotary evaporation. The resulting crude extract was resuspended in 300 mL solvent grade methanol and filtered through a fritted glass funnel containing silica gel (9×2 cm) via vacuum filtration and concentrated to dryness. Extracts were resuspended at a final concentration of 200 mg/mL in HPLC grade methanol prior to analysis by LC/MS.

Isolation of Everninomicin-Rosaramicin Conjugates

The first dimension of separation for crude extracts was size-exclusion chromatography using a Sephadex LH20 column in methanol. Fractions were analyzed by LC/MS, and the fractions containing the everninomicins were combined and separated on a RP-HPLC using a linear gradient. Mobile phases were: (A) 99% water/1% acetonitrile with 10 mM ammonium acetate, pH=8 and (B) 5% water/95% acetonitrile with 10 mM ammonium acetate, pH=8.

Degradation of Everninomicin-Rosaramicin Conjugate

Purified, full-length everninomicin-rosaramicin conjugate (9) (concentration of 0.2 mg/mL in 90% water/10% DMSO) was incubated at 30° C. with shaking for 48 hours. Aliquots were taken at designated time points and subjected to LC/MS analysis.

Mass Spectral Analysis of Everninomicins

Extracts were analyzed in both negative and positive ion modes using a TSQ Quantum Access Max triple stage quadrupole mass spectrometer (Thermo Scientific, Waltham, Mass.) equipped with a HESI electrospray ionization source. Injections of 20 μl were separated on an Accucore C18 column (particle size: 2.6 μm, 150×4.6 mm, Thermo Scientific, Waltham, Mass.) or a Luna C18(2) column (particle size: 5 μm, 250×4.6 mm, Phenomenex, Torrance, Calif.) using a Finnigan Surveyor LC Pump Plus (Thermo Scientific, Waltham, Mass.). Mobile phases were: (A) 95% water/5% acetonitrile with 10 mM ammonium acetate and (B) 5% water/95% acetonitrile with 10 mM ammonium acetate. Gradient conditions for the Accucore C18 column were: 0-1 min, 100% A; 1-20 min, linear gradient to 100% B; 20-26 min, 100% B; 26-7 min, linear gradient to 100% A; 27-30 min, 100% A. Gradient conditions for the Luna C18 column were: 0-1 min, 100% A; 1-30 min, linear gradient to 100% B; 30-45 min, 100% B; 45-47, linear gradient to 100% A; 47-50 min, 100% A. The flow rate was maintained at 1 mL/min with 15 μL sent to an Accela PDA detector (Thermo Scientific) and 5 μL subjected to mass spectral analysis. Nitrogen was used for both the auxiliary and sheath gas set to 10 psi and 54 psi respectively. For analysis in positive ion mode: capillary temperature 275° C.; spray voltage 4.5 kV; capillary offset 35V; tube lens voltage 133V; skimmer offset 5V. For analysis in negative ion mode: capillary temperature 275° C.; spray voltage 3.0 kV; capillary offset −35V; tube lens voltage −132V; skimmer offset 5V. For fragmentation studies, a collision energy or 20, 30 35, or 40 V were used with a collision energy of 35 V producing the best results.

Bioactivity Testing Against *S. aureus* Subsp. *Aureus* Rosenbach

The antibacterial activity of purified everninomicins and conjugates was determined by the broth microdilution assay according to NCCLS guidelines using *Staphyloccocus aureus* subsp. *aureus* Rosenbach (ATCC 6538P) as the test organism.

*M. carbonacea* Var *Aurantiaca* Conjugation without Membrane

*M. carbonacea* was grown on TSB agar (Oxoid™ Tryptone Soy Broth, 2% agarose) for 7 days at 30° C. Conjugal acceptor mycelia were prepared by inoculating a loop of mycelia into 10 mL of TSB medium in a 50 mL Falcon tube and incubating with shaking at 30° C. for 5 days. The culture was then centrifuged at 3000×g for 10 minutes and the pellet resuspended in 2 mL fresh TSB. 150 μL aliquots were transferred into sterile 1.5 mL Eppendorf tubes and homogenized using a sterile plastic cell homogenizer. Donor *E. coli* ET12567/pUZ8002 cells containing the gene replacement were prepared by inoculating 1% of a freshly prepared overnight LB culture into 10 mL LB medium in a 50 mL Falcon tube containing apramycin and kanamycin and grown to an $OD_{600}$ of 0.4 at 37° C. with shaking. The culture was centrifuged at 3000×g for 10 minutes, and the pellet was washed three times with 10 mL fresh LB. After the final wash, the pellet was resuspended in 150 μL LB. 50 μL of donor *E. coli* was added to 150 μL of recipient *M. carbonacea*. The bacterial mixture was plated on AS1 agar (0.1% yeast extract, 0.5% soluble starch, 0.02% L-alanine, 0.02% L-arginine, 0.05% L-asparagine, 0.25% NaCl, 1% $Na_2SO_4$, 2% agarose at pH 7.5, supplemented with 10 mM MgCl2). The plates were then incubated at 37° C. for 1-2 hours until thoroughly dried. After 16-20 hours of incubation at 30° C., apramycin (50 μg/mL) and nalidixic acid (12.5 μg/mL) were spread on the plates. The plates were then incubated for an additional at 30° C. for an additional 6-9 days until colonies were clearly visible. Conjugation colonies were then picked using a sterile pipette tip onto a fresh TSB plate containing apramycin (50 μg/mL) and nalidixic acid (12.5 μg/mL). This process was repeated until pure *M. carbonacea* colonies were isolated.

*M. carbonacea* Var *Aurantiaca* Conjugation with Membrane

Donor and recipient cultures were prepared as above. Prior to plating, a sterile 0.4 m membrane (EMD Millipore, Item No. HTTP04700) was attached to a sterile plastic washer using Dow Corning™ 732 multipurpose sealant (100% silicon rubber). After drying, each membrane-washer apparatus was placed on an AS1 agar plate. Then the mixture of bacteria was plated on top of the membrane. Each plate was incubated at 37° C. for 1-2 hours until completely dried. After 16 hours of incubation at 30° C., apramycin (50 μg/mL) was added to the bacteria mixture on top of the washer to select for apramycin-resistant exconjugants. After 7-9 days of incubation at 30° C., membranes were removed and pure colonies were streaked onto TSB plates containing apramycin.

Improvements in Everninomicin Production Parameters

Figure 5:
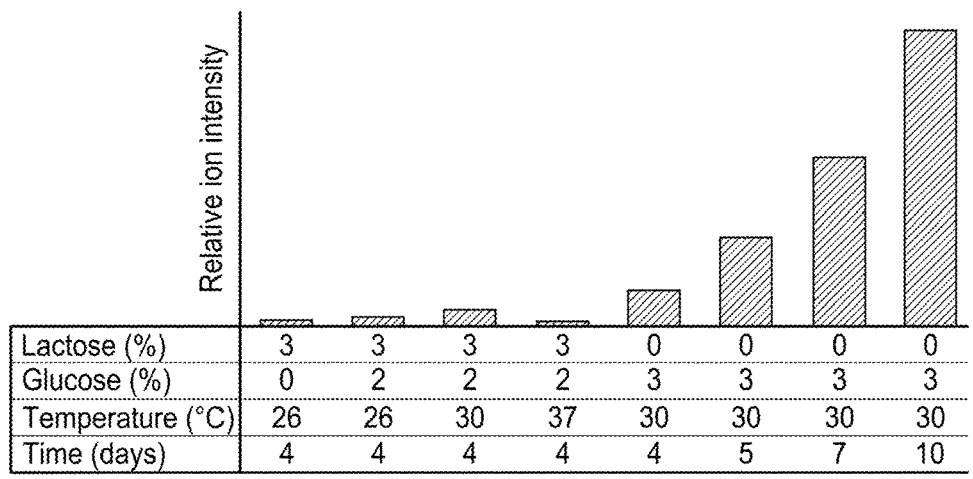
FIG. 5 is a graph showing relative levels of everninomicin F produced by each culture condition are shown.

Initially, production of everninomicins was extremely low rendering analysis of wild-type everninomicins difficult and analysis of metabolites from mutant strains, where production was even lower, impossible. To improve everninomicin titers, production parameters including media components, temperature, and time were modified. Original production parameters, which were extracted from a patent, were media components of 3% lactose, 0.5% yeast extract, 0.1% corn steep solids, and 0.1% calcium carbonate with an incubation temperature of 26° C. and a production time of 4 days. As glucose is the precursor to most of the sugars of everninomicin, glucose was added to increase production levels. Indeed the addition of 2% glucose to the media increased everninomicin production slightly, and increasing the temperature to 30° C. produced even greater everninomicin levels (35% and 133% improvements respectively, FIG. 5). However, increasing the temperature to 37° C. had a negative impact on production. Adding additional glucose and removing the disaccharide lactose from the media resulted in another substantial (384%) improvement in everninomicin production. The final parameter that was modified was time.

The length of time the culture spent in the production phase was directly linked with everninomicin production levels with a length of 10 days producing the highest titers of everninomicin, an increase of over 3,000%.

Identification of Everninomicins Produced by *M. carbonacea* Var *Aurantiaca*

To characterize the everninomicins produced by *M. carbonacea* var *aurantiaca*, mass spectrometric fragmentation was employed. Using this method, the major everninomicin analogs that were produced by *M. carbonacea* var *aurantiaca*, termed everninomicins D-G (1-4), were identified (extracted ion chromatogram from LC/MS analysis of everninomicins in negative mode: ever D, m/z=1534.5 [M−H]−; ever D, m/z=1504.5, [M−H]−; ever F, m/z=1522.5 [M−H]−; ever G, m/z=1520.5 [M−H]−). Each of these congeners differ in the oxidation state of the nitrogen providing a ladder of biosynthetic intermediates moving from the amino through the hydroxyl amino and nitroso stages to the fully oxidized nitro. Based solely on relative ion intensity, the hydroxyl amino oxidation state is the major everninomicin congener produced by *M. carbonacea* var *aurantiaca* (Scheme 2, "R" is the oxidation state of the nitrogen).

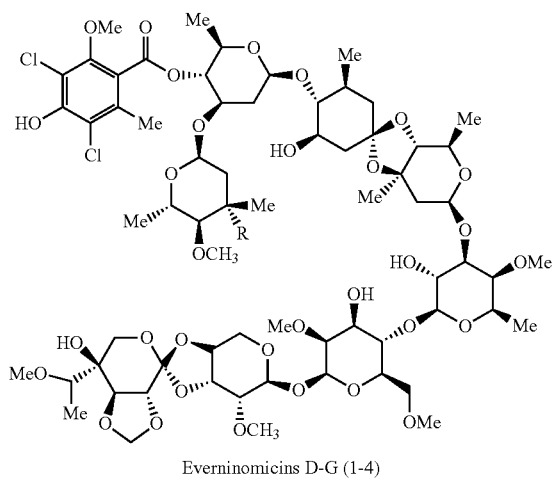

Everninomicins D-G (1-4)

The lability of the glycosidic linkages was exploited to generate a predictable fragmentation pattern where each transition represents the loss of a sugar residue. Of note, loss of the A ring to give a positively charged ion is used to diagnose the N-oxidation state. Fragmentation of everninomicin F (3), the most abundant everninomicin, reveals that the highly labile orthoester linkage between rings C and D fragments first to give a pentasaccharide fragment. The sequential loss of sugar residues E-H then occurs in a predictable fashion. On the western portion of the molecule, fragments are observed for $A_1$-(A)-B-C-D rings with loss of the $A_1$ and B residues as a unit and sequential loss of other residues. A similar fragmentation pattern is observed for everninomicin E (2) although not as many fragments were identified due to lower production levels. This predictable fragmentation pattern allowed for the facile identification of wild type everninomicins and was essential for the characterization of metabolites produced by mutant strains.

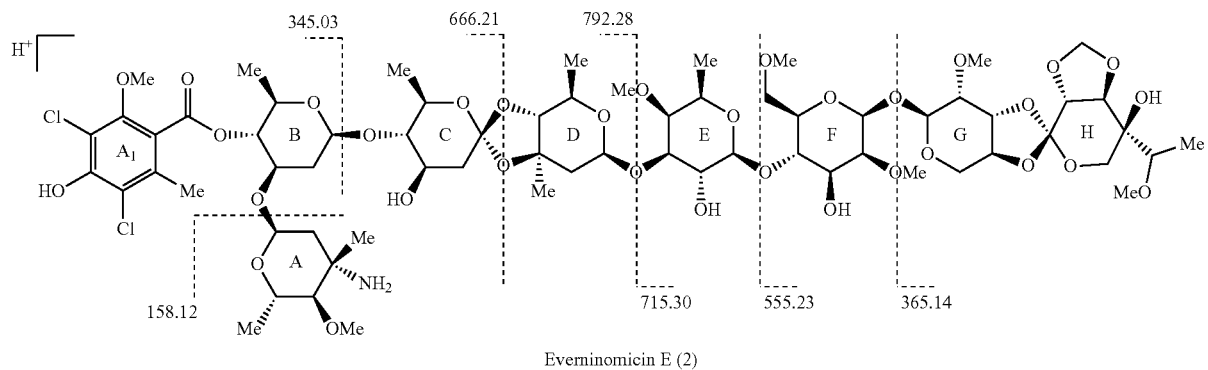

Everninomicin E (2)

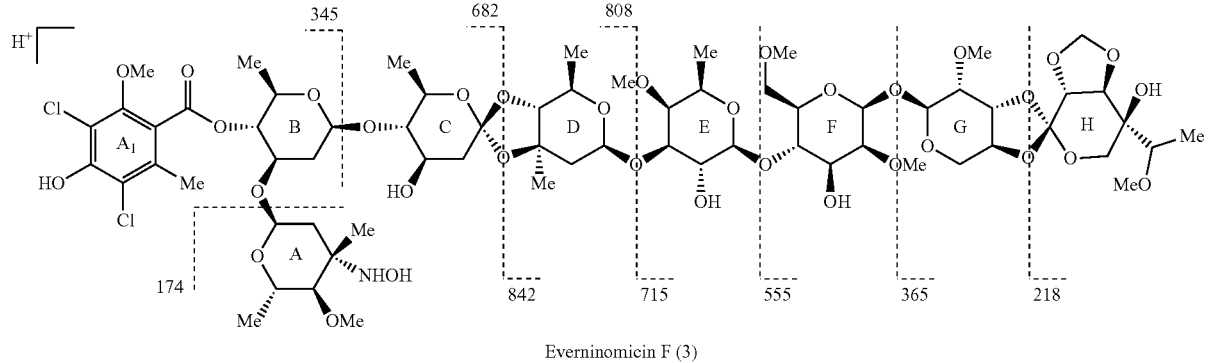

Everninomicin F (3)

Identification of a Bifunctional Antibiotic

Figure 6A:
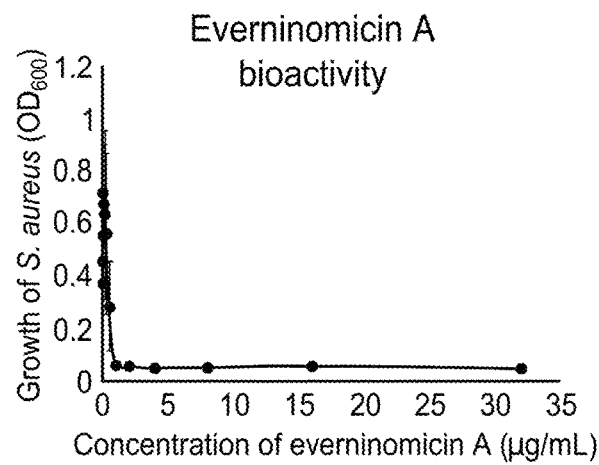
FIGS. 6A-6C are graphs showing the minimal inhibitory concentration of each everninomicin analog was tested against *S. aureus* subsp. *aureus* Rosenbach.
Figure 6B:
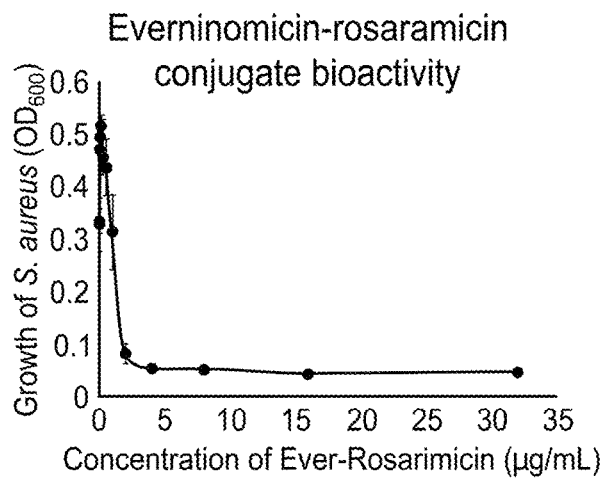
Figure 6C:
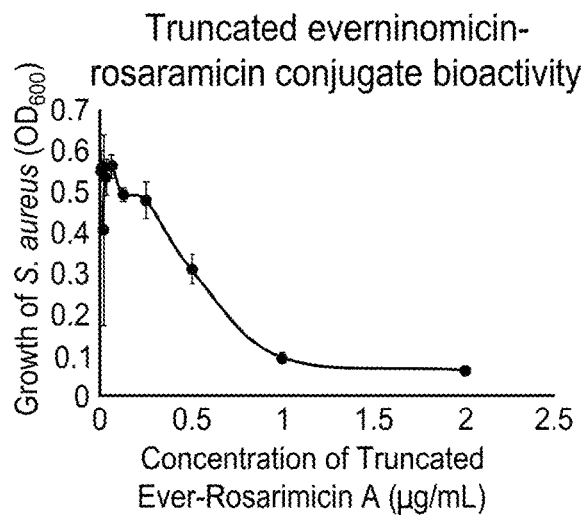
Figure 19:
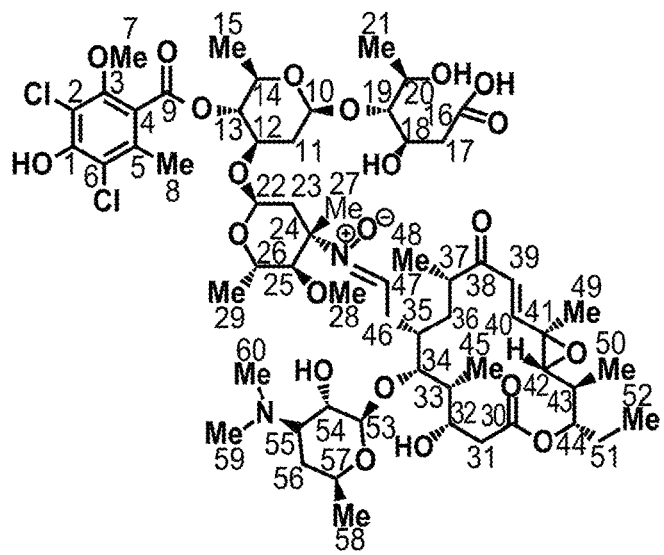
FIG. 19 shows the truncated everninomicin-rosaramicin conjugate (8) NMR data.
Figure 20:
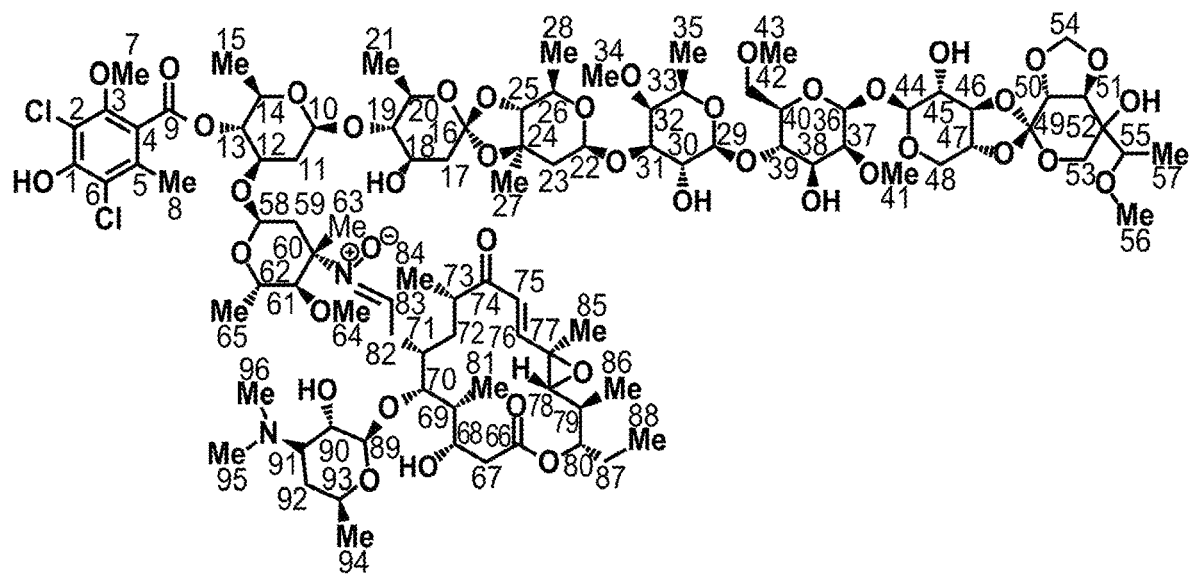
FIG. 20 shows the everninomicin-rosaramicin conjugate (9) NMR data

A surprising discovery while evaluating the everninomicins produced by this variant is that everninomicin F reacts with another natural product, rosaramicin (5), also produced by M. carbonacea. Specifically, the hydroxyl amino functionality of everninomicin F reacts with the aldehyde of rosaramicin to produce a nitrone that tethers the two metabolites together. Rosaramicin (also known as rosamicin) is a 16-membered macrolide antibiotic which has previously been characterized from M. rosaria and has activity against a variety of organisms including S. aureus, Neisseria gonorrhoeae, and Chlamydia trachomatis. In addition to the full-length everninomicin-rosaramicin conjugate (6), a truncated version is also present in the crude extracts of wild type M. carbonacea. Structures of both the truncated and full-length conjugate were solved by NMR (FIG. 19 and FIG. 20). The full-length everninomicin-rosaramicin conjugate degrades under normal culture conditions to an everninomicin-trisaccharide which is still tethered through the nitrone linkage to rosaramicin (7). When these two conjugates were tested against S. aureus subsp. aureus Rosenbach in a broth microdilution assay, both everninomicin-rosaramicin conjugates were found to have an MIC equal to that of everninomicin A (FIG. 6A, 1 µg/mL). The unexpected discovery of this everninomicin-rosaramicin conjugate provides an interesting study of a bifunctional antibiotic composed of members of two distinct classes of molecules.

Transformation of M. carbonacea Var Aurantiaca Via Conjugation

In order to interrogate the biosynthesis of the everninomicins and to create new analogs by alteration of the biosynthetic machinery, a robust procedure for genetic manipulation of M. carbonacea was required. Previous reports of transformation of M. carbonacea and other Micromonospora species relied on intergeneric conjugation although few details were reported. Unfortunately, classical methods for intergeneric conjugation did not produce efficient transformation results. Therefore, an alternative method for the transformation of M. carbonacea by intergeneric conjugation was developed. Typically, nalidixic acid is used to remove the E. coli from the conjugation mixture. However, at concentrations that effectively kill E. coli, M. carbonacea cannot survive. Different concentrations of nalidixic acid were tested to find the best balance between killing of E. coli and survival of M. carbonacea. At 50 µg/mL, M. carbonacea was not viable. A nalidixic acid concentration of 25 µg/mL, stunted the growth of E. coli but also stunted the growth of M. carbonacea. Lowering the concentration of nalidixic acid to 12.5 µg/mL still stunted E. coli growth but allowed for substantially more M. carbonacea growth. Subsequent transformations were conducted with 12.5 µg/mL nalidixic acid.

To further improve conjugation efficiencies, excess E. coli were gently washed from the conjugation plates after 16 hours of incubation immediately before application of antibiotics. As conjugation requires physical interaction between the donor and recipient organisms, M. carbonacea cultures were mechanically homogenized to create a greater surface area for conjugation between the donor E. coli and the recipient M. carbonacea. Additionally, since conjugation between bacteria happens most efficiently on solid surfaces rather than in liquid, thoroughly drying the plates at 37° C. after initial plating of the bacteria resulted in higher conjugation efficiencies. Finally, conjugation efficiencies were evaluated at both 30° C. and 37° C. with incubation at 30° C. yielding the greatest number of colonies.

Figures 7A, 7B:
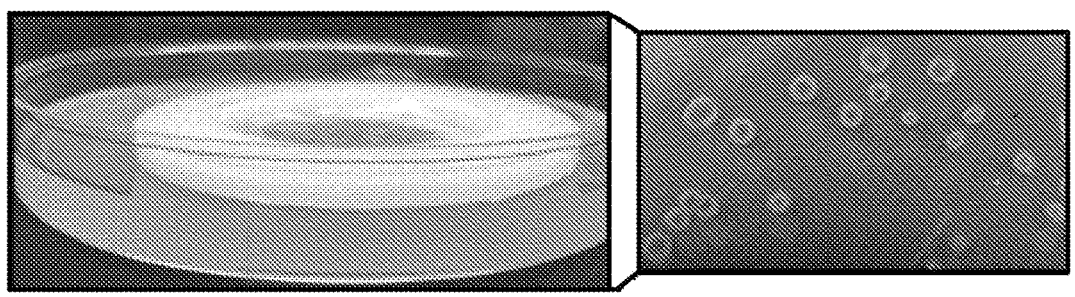
FIG. 7A is a photograph of a washer/membrane assembly with conjugation mixture plate in the center.
FIG. 7B is a photograph showing that after 9 days the washer/membrane assembly was removed, pure colonies of apramycin-resistant exconjugants remained.

Although the above modifications to the conjugation procedure yielded sufficient conjugation efficiencies, a nalidixic acid-free method for the removal of E. coli has been developed allowing easier and faster isolation of pure M. carbonacea exconjugants. The conjugation mixture of the donor and recipient bacteria is plated on a 0.4 µm membrane surrounded by a sterile plastic washer on AS1 agar (FIG. 7A). Prior to plating, the membrane is attached to the washer by silicon glue. The washer contains the bacterial mixture while the membrane allows selective penetration of M. carbonacea but not the E. coli to the agar beneath. After 9 days the washer/membrane assembly is removed revealing pure colonies of apramycin-resistant exconjugants on the agar (FIG. 7B).

Development of a Genetic Complementation System

Figure 8:
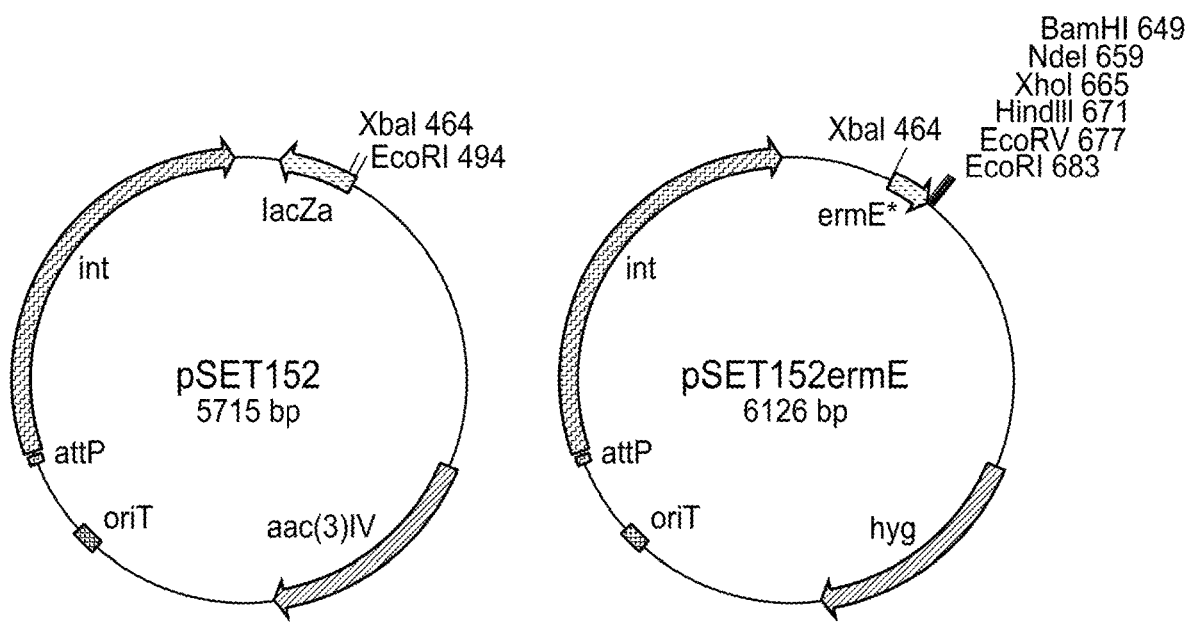
FIG. 8 contains maps of pSET152 and pSET152ermE. aac(3)IV is the apramycin resistance marker; hyg is the hygromycin resistance marker hph; oriT is the origin of transfer; int is the phage φC31 integrase; attP is the phage φC31 attachment site; ermE* encodes a constitutively active promoter directly upstream of the multiple cloning site.

As no suitable genetic complementation plasmid was available, a new vector, pSET152ermE, was created by modifying pSET152, a commonly used integrative vector for use in actinomycetes (FIG. 8). The modified vector was designed in our lab and then ordered from Mutagenex. Requirements for a genetic complementation plasmid included an appropriate resistance marker, a constitutively active promoter for expression of the gene of interest, an origin of transfer site (oriT) for conjugation into an actinomycete, and an integrase for stable incorporation into the host chromosome. pSET152 already contained an integrase and oriT but lacked the appropriate resistance marker and promoter. pSET152 was first modified by replacing the apramycin resistance element (aac(3)IV) with a hygromycin B phosphotransfersase, hph, conferring resistance to hygromycin B. Additionally, ermE*, which encodes a constitutively active promoter, in combination with a downstream multiple cloning site was cloned into the XbaI and EcoRI sites of pSET152. The newly created pSET152ermE was readily transformed into wild type M. carbonacea via conjugation. Successful transformation was confirmed by PCR amplification of the hygromycin resistance gene. pSET152ermE is not restricted to use in only M. carbonacea. pSET152ermE can be successfully transformed into Nocardiopsis FU40, an unrelated soil actinomycete.

Annotation of the Evd, Eve, and Ava Gene Clusters

Figure 10:
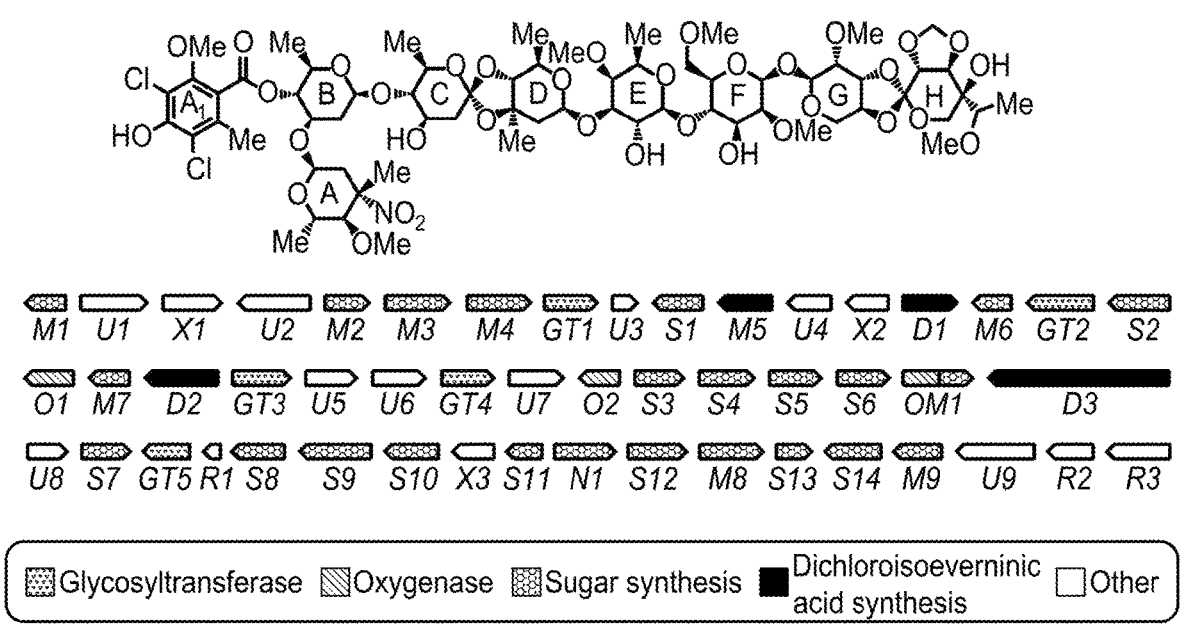
FIG. 10 is a depiction and deduced functional assignment of ORFs from the evd gene cluster of *M. carbonacea* var *aurantiaca*.
Figure 11:
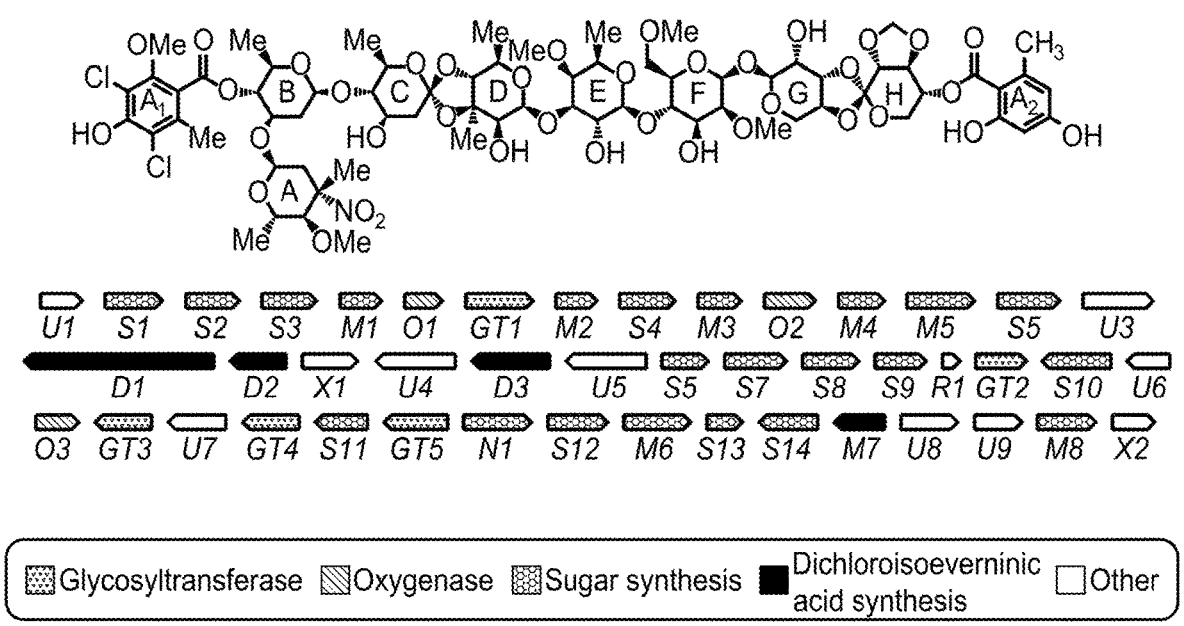
FIG. 11 is a depiction and deduced functional assignment of ORFs from the eve gene cluster of *M. carbonacea* var *africana*.

Five orthosomycin gene clusters are available in GenBank: ava (avilamycin biosynthesis from Streptomyces mobaraensis), avi (avilamycin biosynthesis from S. viridochromogenes Tü57), evd (everninomicin biosynthesis from Micromonospora carbonacea var aurantiaca), eve (everninomicin biosynthesis from M. carbonacea var africana), and hyg (hygromycin B biosynthesis from S. hygroscopicus). However, only two of these clusters, avi and hyg, include functional annotation. Therefore, translated sequence similarities and comparative genomics were used to propose functions for the ava, evd, and eve gene clusters. FIG. 10, FIG. 11, and FIG. 12 depict the arrangement and deduced functions of the evd, eve, and ava gene clusters respectively.

Using antiSMASH, open reading frames (ORFs) were identified from GenBank nucleotide sequences. Each ORF was analyzed using Translated BLAST (BlastX). Based on the function of homologous proteins, gene names were assigned and functions were proposed.

Generation of Gene Replacements in E. coli

The genes evdM2, evdM3, and evdN1 were individually deleted on cosmids CA or CG using a PCR-targeted gene replacement strategy. Lambda Red competent cells were prepared by inoculating 1% of a fresh overnight culture of E. coli BW25113/pIJ790 containing either cosmid CA or cosmid CG into 10 mL LB medium containing 20 mM MgSO$_4$, 50 µg/mL kanamycin, 30 µg/mL chloramphenicol, and 10 mM L-arabinose. The culture was grown with shaking at 30° C. to an OD$_{600}$ of 0.6. The cells were recovered by centrifugation at 3000×g for 10 minutes at 4° C. The pellet was washed three times with 10 mL ice-cold 10% glycerol. The pellet was then resuspended in 100 µL ice-cold 10% glycerol and kept on ice until transformation.

The gene replacement cassette containing the apramycin resistance marker (aac(3)IV), oriT, and FRT regions was amplified by PCR using the primers listed in Table 1. The 1.4 kb PCR products were then directly transformed via electroporation into the arabinose-induced strain BW25113/pIJ790 containing the cosmid where lambda Red mediated homologous recombination enabled replacement of the gene of interest. Transformed *E. coli* were plated on LB agar containing apramycin and incubated overnight at 37° C. to promote loss of the temperature sensitive plasmid pIJ790. Colonies from these plates were inoculated into liquid LB containing apramycin and grown with shaking overnight at 37° C. The gene replacements were confirmed by PCR using primers DelUp and DelDn and sequencing. The resultant cosmids were transformed via electroporation into the non-methylating *E. coli* strain ET12567 containing plasmid pUZ8002, which contains the genes necessary for conjugal transfer of the cosmid. The gene replacements in *E. coli* were maintained at 37° C. in liquid LB medium containing kanamycin, apramycin, and chloramphenicol.

The second step of the PCR-targeted *Streptomyces* gene-replacement strategy was replacement of the gene(s) of interest in the everninomicin-producing organism. Transformation of *M. carbonacea* var *aurantiaca* was accomplished using the methods described herein. Two rounds of homologous recombination were necessary to generate in-frame double crossovers. After 7-9 d of incubation at 30° C., exconjugants were streaked onto solid TSB medium containing either apramycin or kanamycin to identify double-crossover mutants. Double crossovers were confirmed by PCR amplification of the kanamycin and apramycin resistance genes using the primers AprUp and AprDn for amplifying the apramycin resistance gene and NeoUp and NeoDn for amplifying the kanamycin resistance gene (sequences can be found in Table 1).

Double-crossover mutants in *M. carbonacea* were confirmed by Southern hybridization. Gene specific probes were designed upstream of the genes of interest (primer sequences can be found in Table 1). The evdM2 probe (782 bp) was amplified using primers EvdM2-Southern-For and EvdM2-Southern-Rev. The evdM3 probe (574 bp) was amplified using primers EvdM3 Southern-For and EvdM3-Southern-Rev. The evdN1 probe (700 bp) was amplified using primers EvdN1-Southern-For and EvdN1-Southern-Rev. An 884 bp probe specific to the apramycin resistance gene was also designed and amplified using primers Apr-Southern-For and Apr Southern-Rev. All probes were labeled with digoxigenin using the DIG High Prime DNA Labeling and Detection Starter Kit II (Roche, Cat No: 11585614910). Hybridization and detection were performed using the aforementioned DIG Starter Kit.

TABLE 1

Primer Sequences

| Primer Name | Purpose | Sequence (5'-3') | SEQ ID. |
|---|---|---|---|
| RED-N1-For | ΔevdN1::aac(3)IV | ATGGTCGACCTGCTGACCGGCGTACTCCCGCAGATCCGGATTCCGGGGATCCGTCGACC | 1 |
| RED-N1-Rev | ΔevdN1::aac(3)IV | ATTCCGGCAGGTAGTCCCACACTCGGATGGTCATGTTCATGTAGGCTGGAGCTGCTTC | 2 |
| RED-M2-For | ΔevdM2::aac(3)IV | GACACCGCCGGTCCACCGTGGGCAGGAGCCCCGGCGGTGATTCCGGGGATCCGTCGACC | 3 |
| RED-M2-Rev | ΔevdM2::aac(3)IV | CCACGCTCTCGTCATACGCTGATGCGGTCCGACTCACGTTGTAGGCTGGAGCTGCTTC | 4 |
| RED-M3-For | ΔevdM3::aac(3)IV | CGCCCGGAAACCCCACACGAAGGAGACCGCTACGTGAGTATTCCGGGGATCCGTCGACC | 5 |
| RED-M3-Rev | ΔevdM3::aac(3)IV | CCGCCGCGGCGAGCAGCCGCTGGACGAGCGAGCCGGTCATGTAGGCTGGAGCTGCTTC | 6 |
| EvdM2-Southern-For | EvdM2 Southern Probe | CGTTCGGGTAGTCGTAGACC | 7 |
| EvdM2-Southern-Rev | EvdM2 Southern Probe | ACTAGGGTTTCCCCCACAAC | 8 |
| EvdM3-Southern-For | EvdM3 Southern Probe | TACGCGCACTTCATCGATCT | 9 |
| EvdM3-Southern-Rev | EvdM3 Southern Probe | GATACGTGTCCAGGGAGCTG | 10 |
| EvdN1-Southern-For | EvdN1 Southern Probe | ACGACGAGCACTTCTTCCTG | 11 |
| EvdN1-Southern-Rev | EvdN1 Southern Probe | GAAGACCGAGTCCAGGTACG | 12 |
| Apr-Southern-For | Apramycin Southern Probe | ACCGACTGGACCTTCCTTCT | 13 |
| Apr-Southern-Rev | Apramycin Southern Probe | TCGCTATAATGACCCCGAAG | 14 |
| EvdM2-GC-For | pSET152ermE*-evdM2 | CATATGGTGATCGGCTTGCTGGGC | 15 |
| EvdM2-GC-Rev | pSET152ermE*-evdM2 | AGTACTGTAGCGGTCTCCTTCGTGTG | 16 |
| EvdN1-GC-For | pSET152ermE*-evdN1 | CATATGAGCGAATTCATGGTCGACCTG | 17 |

TABLE 1-continued

Primer Sequences

| Primer Name | Purpose | Sequence (5'-3') | SEQ ID. |
|---|---|---|---|
| EvdN1-GC-Rev | pSET152ermE*-evdN1 | GATATCCACTCGGATGGTCATGTTCA | 18 |
| EvdM3-GC-For | pSET152ermE*-evdM3 | CATATGGTGAGTCGGACCGCATCA | 19 |
| EvdM3-GC-Rev | pSET152ermE*-evdM3 | GATATCTCACGACCCCACCCGCGA | 20 |
| HygBCheck-For | Confirm GC vectors | GATTCGGATGATTCCTACGC | 21 |
| HygBCheck-Rev | Confirm GC vectors | GAAGGCGTTGAGATGCAGTT | 22 |
| Apr-For | Confirm gene replacements | ATTCCGGGGATCCGTCGACC | 23 |
| Apr-Rev | Confirm gene replacements | TGTAGGCTGGAGCTGCTTC | 24 |
| Neo-For | Confirm gene replacements | TGAATGAACTGCAGGACGAG | 25 |
| Neo-Rev | Confirm gene replacements | AATATCACGGGTAGCCAA | 26 |

Complementation of Gene Replacement Mutants

Figure 9:
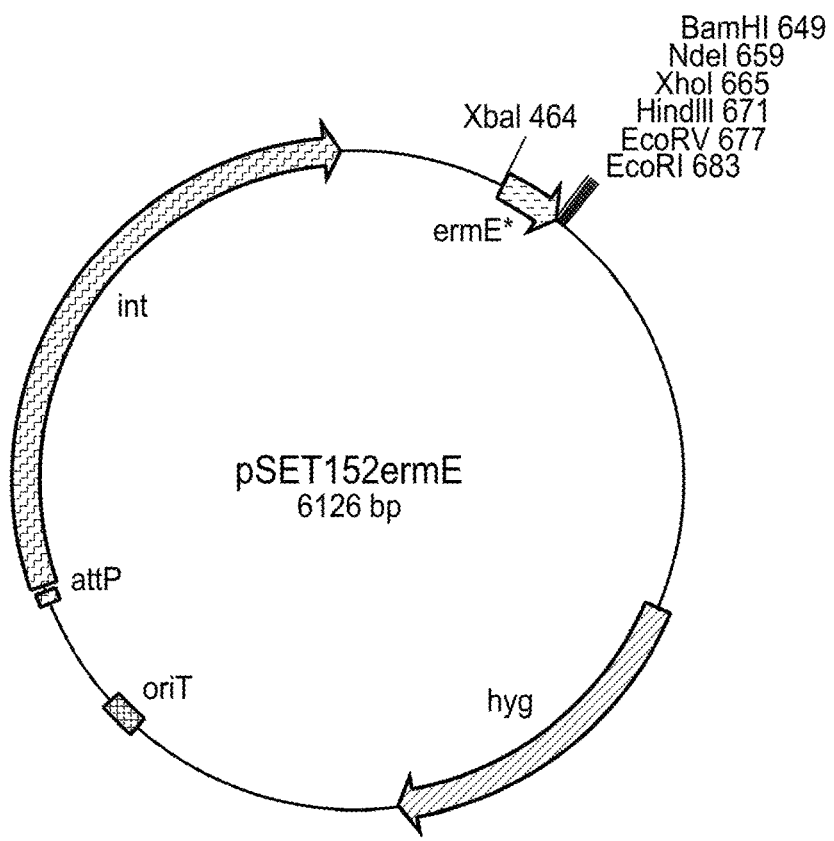
FIG. 9 is a map of pSET152ermE, the genetic complementation plasmid. Plasmid map was generated using Savvy (Scalable Vector Graphics & Plasmid Map Copyright© 2001, Malay K Basu) at http://www.bioinformatics.org/savvy/. Hyg is the hygromycin resistance marker hph; oriT is the origin of transfer; int is the phage φC31 integrase; attP is the phage φC31 attachment site; ermE* is the constitutively active promoter directly upstream of the multiple cloning site.

To generate a suitable complementation plasmid for use in M. carbonacea var aurantiaca, a pSET152 derivative was designed and ordered from Mutagenex. Starting with pSET152, the constitutive promoter ermE* was inserted upstream of the multiple cloning site. Next, the apramycin resistance gene (aac(3)IV) was replaced with the hygromycin B resistance marker hyg to generate the new complementation plasmid, pSET152ermE (map in FIG. 9). For complementation of ΔevdM2::aac(3)IV, ΔevdM3::aac(3)IV, and ΔevdN1::aac(3)IV, evdM2, evdM3, and evdN1 were amplified by PCR using the primers listed in Table 1. The PCR products were subsequently cloned into the NdeI and EcoRV sites of pSET152ermE to generate complementation plasmids for each mutant strain.

Each of the complementation plasmids above were transformed into the conjugal E. coli strain ET12567/pUZ8002. Conjugation between the donor E. coli and recipient M. carbonacea was performed in the same manner as described previously except that apramycin and hygromycin were added after 16 hours of incubation to select for mutants that contained the gene replacement as well as the genetic complementation plasmid. Crude extracts of the complemented strains were prepared and analyzed by HPLC/MS as described herein.

Analysis of Metabolites from M. carbonacea Var Aurantiaca Mutants

Seed cultures were generated by inoculating a loop of mycelia from TSB agar into 100 mL of 2997 Germination Medium (0.3% beef extract, 0.5% tryptose, 0.1% dextrose, 2.4% soluble starch, 0.5% yeast extract, 0.1% calcium carbonate, 50 μg/ml apramycin) for 5 days at 30° C. in a 500 mL Erlenmeyer flask with shaking. For production, 25 mL of the seed culture was added to 500 mL apramycin-free Production Medium (0.5% yeast extract, 0.1% corn steep solids, 0.1% calcium carbonate, 3% glucose) in a 2 L baffled Fernbach flask and grown with shaking at 30° C. for 10 days. Diaion HP-20 resin (100 mL, previously pre-equilibrated with methanol and washed with water) was added to the fermentation cultures and incubated for 60 minutes with shaking. The combined resin and mycelia were collected by centrifugation at 3000×g, extracted successively with 250 mL methanol and 250 mL acetone, and evaporated to dryness by rotary evaporation. The resulting crude extract was resuspended in 300 mL solvent grade methanol and filtered through a fritted glass funnel containing silica gel (9×2 cm) via vacuum filtration and concentrated to dryness. Extracts were resuspended at a final concentration of 200 mg/mL in HPLC grade methanol prior to analysis by LC/MS. Mass spectral analysis of crude extracts was accomplished using the methods described herein.

Isolation of Everninomicin H

The first dimension of separation for crude extracts was size-exclusion chromatography using a Sephadex LH20 column in methanol. Fractions were analyzed by LC/MS, and the fractions containing everninomicin H were combined and separated using reverse phase HPLC using a linear gradient. Mobile phases were: (A) 99% water/1% acetonitrile with 10 mM ammonium acetate, pH=8 and (B) 5% water/95% acetonitrile with 10 mM ammonium acetate, pH=8.

Structural Analysis of Everninomicin Analogs

Figures 20, 21:
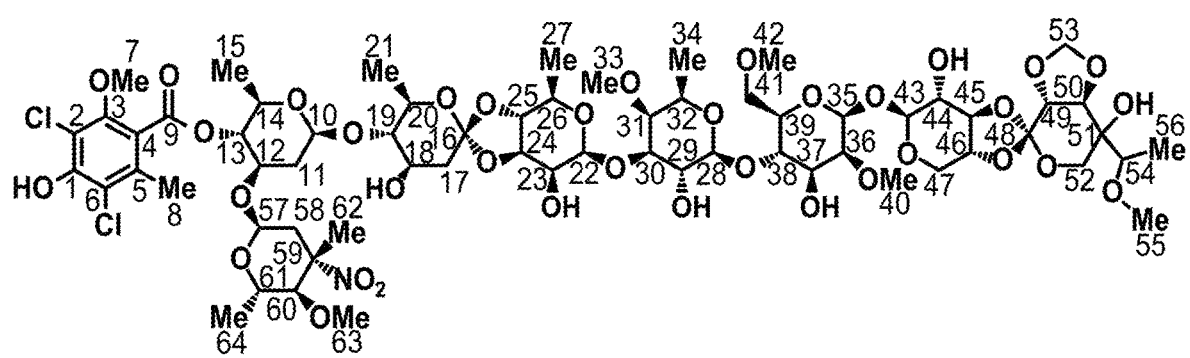
FIG. 21 shows the everninomicin H (11) NMR data.

The structure of Ever-2 was confirmed using the TSQ Quantum Access Max triple stage quadrupole mass spectrometer and parameters described herein. Collision energies of 20 V-40 V with a skimmer offset of 5 V were employed in positive mode to fragment Ever-2. The structure of eveminomicin H was determined by NMR analysis. Structures of everninomicins H, J, and K were determined using a 15T Bruker FTICR (FIG. 21).

LC/MS analysis of wild type M. carbonacea var aurantiaca, gene replacement of evdN1 (ΔevdN1::aac(3)IV), and genetic complementation of evdN1 gene replacement (ΔevdN1::aac(3)IV_GC). The chromatogram ion intensities for eveminomicins D-G and the truncated everninomicin-rosaramicin conjugate: Negative mode ever D (1), m/z=1,534.5 $[M-H]^-$; ever E (2), m/z=1,504.5 $[M-H]^-$; ever F (3), m/z=1,520.5 $[M-H]^-$; and ever G (4), m/z=1,518.5 $[M-H]^-$; conjugate (6) 1261.5 $[M-H]^-$; ever-2, m/z=1347.5 $[M-H]^-$. Positive mode (solid lines): ever D, m/z=1,536.5 $[M+H]^+$; ever E, m/z=1,506.5 $[M+H]^+$; ever F, m/z=1,522.5 $[M+H]^+$; and ever G, m/z=1,520.5 $[M+H]^+$; conjugate 1261.5 $[M+H]^+$; ever-2 (5), m/z=1349.5 $[M+H]^+$.

LC/MS analysis of wild type M. carbonacea var aurantiaca, gene replacement of evdM3 (ΔevdM3::aac(3)IV), and genetic complementation of evdM3 gene replacement (Δevd3::aac(3)IV_GC). The chromatogram ion intensities for everninomicins D-G and the truncated everninomicin-rosaramicin conjugate: Negative mode (dotted lines): ever D (1), m/z=1,534.5 $[M-H]^-$; ever E (2), m/z=1,504.5 $[M-H]^-$; ever F (3), m/z=1,520.5 $[M-H]^-$; and ever G (4), m/z=1,518.5 $[M-H]^-$; conjugate (6) 1261.5 $[M-H]^-$; ever H, m/z=1521.5 $[M-H]^-$. Positive mode (solid lines): ever D, m/z=1,536.5 $[M+H]^+$; ever E, m/z=1,506.5 $[M+H]^+$; ever F, m/z=1,522.5 $[M+H]^+$; and ever G, m/z=1,520.5 $[M+H]^+$; conjugate 1261.5 $[M+H]^+$; ever J, m/z=1494.5 $[M+H]^+$; ever K, m/z=1508.5 $[M+H]^+$; ever L, m/z=1555.5 $[M+H_2O]^+$.

LC/MS analysis of wild type M. carbonacea var aurantiaca, gene replacement of evdM2 (ΔevdM2::aac(3)IV), and genetic complementation of evdM3 gene replacement (ΔevdM2::aac(3)IV_GC) and structure of the truncated everninomicin-rosaramicin conjugate. The chromatogram ion intensities for everninomicin D-G and the truncated everninomicin-rosaramicin conjugate: Negative mode (dotted lines): ever D (1), m/z=1,534.5 $[M-H]^-$; ever E (2), m/z=1,504.5 [M−H]⁻; ever F (3), m/z=1,520.5 [M−H]⁻; and ever G (4), m/z=1,518.5 [M−H]⁻; conjugate (6), m/z=1261.5 [M−H]⁻. Positive mode (solid lines): ever D, m/z=1,536.5 [M+H]⁺; ever E, m/z=1,506.5 [M+H]⁺; ever F, m/z=1,522.5 [M+H]⁺; and ever G, m/z=1,520.5 [M+H]⁺; conjugate 1261.5 [M+H]⁺.

Phylogenetic Analysis

Sequences of oxygenases from each of the known orthosomycin pathways and related oxidases were analyzed with MEGA 5 using the neighbor-joining statistical method. Test of phylogeny was the bootstrap method with 1000 replicates.

Construction and Analysis of Gene Replacement Mutants

The genes evdO1, evdO2, and evdMO1 were individually deleted in M. carbonacea var aurantiaca using a modification of the PCR-targeted Streptomyces gene-replacement strategy described in detail herein. The gene replacement cassette containing the aac(3)IV resistance marker, oriT, and flippase recombinase target (FRT) regions was amplified by PCR using primers EvdO1-Red-F and EvdO1-Red-R for the evdO1 gene replacement, EvdO2-Red-F and EvdO2-Red-R for the evdO2 gene replacement, and EvdMO1-Red-F and EvdMO1-Red-R for the evdMO1 gene replacement (primer sequences are found in Table 2). PCR products were then directly transformed via electroporation into the arabinose-induced strain E. coli BW25113/pIJ790 containing cosmid CA in which gene replacement of evdO1, evdO2, or evdMO1 was enabled via λ Red-mediated homologous recombination. The resultant cosmids were transformed via electroporation into the non-methylating E. coli strain ET12567 containing plasmid pUZ8002, which contains the genes necessary for conjugal transfer of the cosmid. The gene replacements in E. coli were maintained at 37° C. in liquid LB medium containing kanamycin, apramycin, and chloramphenicol.

TABLE 2

Primer Sequences

| Primer Name | Purpose | Sequence (5'-3') | SEQ ID |
| --- | --- | --- | --- |
| EvdO1-Red-For | ΔevdO1::aac(3)IV | CGGGCCCGCGACCGCTGATCAGAAGGGTGTGGACTGATGATTCCGGGGATCCGTCGACC | 27 |
| EvdO1-Red-Rev | ΔevdO1::aac(3)IV | CTGTCGCCCGGAACGCTCATCGGATGCCCCCCGAGCTCATGTAGGCTGGAGCTGCTTC | 28 |
| EvdO2-Red-For | ΔevdO2::aac(3)IV | TCGTGACTGTCGAGGTCATCCCTTGAAGGAGACGGCATGATTCCGGGGATCCGTCGACC | 29 |
| EvdO2-Red-Rev | ΔevdO2::aac(3)IV | TGGCCTTCTTCGGGTAGGGGGGCGTGGTCGGGCCGGCTATGTAGGCTGGAGCTGCTTC | 30 |
| EvdMO1-Red-For | ΔevdMO1::aac(3)IV | TTTCCCGCGCGCACCCGAACACTAGGCTTGAATCCATGATTCCGGGGATCCGTCGACC | 31 |
| EvdMO1-Red-Rev | ΔevdMO1::aac(3)IV | GTGGGGTCGCCGCAGGCGGCATCCGCGTCCGGCCGGTCATGTAGGCTGGAGCTGCTTC | 32 |
| AprUp | Confirm Gene Replacements | ATTCCGGGGATCCGTCGACC | 33 |
| AprDn | Confirm Gene Replacements | TGTAGGCTGGAGCTGCTTC | 34 |
| NeoUp | Confirm Gene Replacements | TGAATGAACTGCAGGACGAG | 35 |
| NeoDn | Confirm Gene Replacements | AATATCACGGGTAGCCAA | 36 |
| EvdO1-Southern-For | EvdO1 Southern Probe | TCAGTCCACACCCTTCTGAT | 37 |
| EvdO1-Southern-Rev | EvdO1 Southern Probe | GGCCTGTACCTGATGACGAG | 38 |
| EvdO2-Southern-For | EvdO2 Southern Probe | TGCTGCACTGTCGTTCCTAC | 39 |
| EvdO2-Southern-Rev | EvdO2 Southern Probe | ATACCAGCGCTTTCACGAGT | 40 |
| EvdMO1-Southern-For | EvdMO1 Southern Probe | GTATGGCTCACTGCCTGGTC | 41 |
| EvdMO1-Southern-Rev | EvdOM1 Southern Probe | GGTGCACGATCGGATGAT | 42 |
| Apr-Southern-For | Apramycin Southern Probe | ACCGACTGGACCTTCCTTCT | 43 |
| Apr-Southern-Rev | Apramycin Southern Probe | TCGCTATAATGACCCCGAAG | 44 |
| EvdMO1-GC-For | EvdMO1 Genetic Complementation | CATATGATGGACCGTAGGGAGATTCA | 45 |
| EvMO1-GC-Rev | EvdMO1 Genetic Complementation | GATATCTCAGGACGGGAGGCTCG | 46 |

Construction of gene replacements in M. carbonacea was performed as described herein using the genetic manipulation methods described above. After 7-9 days of incubation at 30° C., membranes were removed and colonies were streaked onto TSB plates containing apramycin. Double-crossover mutants were identified by PCR amplification of kanamycin and apramycin resistance genes using primers Apr-For and Apr-Rev for amplifying the apramycin resistance gene and Neo-For and Neo-Rev for amplifying the kanamycin resistance gene (sequences of primers found in Table 2). Double-crossover mutants in M. carbonacea were confirmed by Southern hybridization. Gene specific probes were designed upstream of the genes of interest (primer sequences can be found in Table 2). The evdO1 probe (785 bp) was amplified using primers EvdO1-Southern-For and EvdO1-Southern-Rev. The evdO2 probe (719 bp) was amplified using primers EvdO2-Southern-For and EvdO2-Southern-Rev. The evdMO1 probe (798 bp) was amplified using primers EvdMO1-Southern-For and EvdMO1-Southern-Rev. An apramycin cassette probe was designed which hybridized to the apramycin resistance gene. The apramycin probe (884 bp) was amplified using primers: Apr-Southern-For and Apr-Southern-Rev. All probes were labeled with digoxigenin (DIG) using DIG High Prime DNA Labeling and Detection Starter Kit II (catalog no. 11585614910; Roche). Hybridization and detection were performed using the aforementioned DIG Starter Kit. Everninomicins produced by the mutant strains were produced and analyzed via HPLC/MS as described above.

Genetic Complementation of Oxygenase Replacements

Genetic complementation was performed as described in above. For complementation of ΔevdO1::aac(3)IV, an additional plasmid was ordered from Mutagenex that included evdO1 cloned into the EcoRV and EcoRI sites of pSET152ermE to generate pSET152ermE+evdO1. For complementation of ΔevdOM1::aac(3)IV, evdMO1 was amplified by PCR using primers EvdMO1-GC-For and EvdMO1-GC-Rev (sequences can be found in Table 2). The PCR product was subsequently cloned into the NdeI and EcoRV sites of pSET152ermE.

Protein Expression and Purification

All genes were synthesized (Mr. Gene for EvdO1 and EvdO2, Genscript for AviO1, GeneArt for HygX) and subcloned into either pET28a(+) (EvdO1, EvdO2, HygX) or pET23 (AviO1). The resulting vector transformed into E. coli BL21(DE3). Cultures were grown at 37° C. in LB (40 µg/mL kanamycin) with shaking to an $OD_{600}$ of 0.4, when the temperature was lowered to 18° C. Protein expression was induced 45 min later at an $OD_{600}$ of 0.6-0.9 by the addition of 0.5 mM IPTG. The cultures continued to shake at low temperature for 16 h and then were harvested by centrifugation at 5,000×g for 15 min and stored at −20° C. Cell pellets were thawed and resuspended in 15 mL of lysis buffer (50 mM $NaH_2PO_4$, 300 mM NaCl, 10 mM imidazole; pH 8.0) per liter of culture and supplemented with one Complete EDTA-free protease inhibitor mixture tablet (Roche Applied Science). The sample was lysed by sonication. After cell lysis, all purification steps were performed at 4° C. Crude lysate was clarified by centrifugation at 40,000×g for 1 h. The supernatant was passed over a Ni-NTA column (Qiagen) equilibrated with lysis buffer. The column was then washed with lysis buffer containing 20 mM imidazole. Protein was eluted using lysis buffer with 250 mM imidazole and immediately diluted 1:1 with lysis buffer. The sample was dialyzed into storage buffer (25 mM Tris, 75 mM NaCl at pH 7.4). To incorporate $Fe^{2+}$, HygX was first incubated with 0.5 mM EDTA for 1 h to remove any $Ni^{2+}$ and then dialyzed extensively against PBS. The sample was then buffer-exchanged to 50 mM Mops (pH 7.0) using a PD-10 column (GE Healthcare Life Sciences). $(NH4)_2Fe(SO4)_2$ was added to a final concentration of 1 mM and allowed to incubate for 30 min. The sample was then run over the PD-10 column to remove excess iron. HygX-Fe was concentrated to 12 mg/mL, flash frozen, and stored at −80° C. The histidine tag was removed from EvdO2 and AviO1 before crystallization. Thrombin (20 U) was added and incubated overnight at 4° C. to remove the N-terminal hexahistidine tag. Cleaved proteins were passed over a Ni-NTA column to separate unprocessed sample, and the flow-through was collected. Samples were further purified through size-exclusion chromatography on a Superdex 200 10/300 GL column equilibrated in storage buffer. Fractions were analyzed using SDS/PAGE, pooled, and concentrated to 18 mg/mL (EvdO1), 6 mg/mL (EvdO2), 16 mg/mL (AviO1), or 16 mg/mL (HygX). Proteins were flash-frozen and stored at −80° C. in aliquots.

Tryptophan Fluorescence Quenching Assay

The $K_d$ of hygromycin B binding to HygX was determined by monitoring the quenching of intrinsic fluorescence from the single tryptophan residue of HygX upon hygromycin B binding. Using a Cary Eclipse Varian fluorescence spectrometer, sample fluorescence was measured at 20° C. with both emission and excitation slits set at 10 nm and detector voltage set to 800 V. The emission wavelength was set to 280 nm, and spectra collected were from 300 to 400 nm, with 350 nm used for calculating binding affinity. Each sample contained 990 µL of 0.5 µM HygX in 25 mM Tris (pH 7.4), 75 mM NaCl, 0.05 mM AKG, and 0.05 mM $NiCl_2$, which was then mixed with 10 µL of hygromycin B (diluted in the above buffer) of varying concentrations. Spectra were measured in triplicate, and the experiment repeated three times. Because hygromycin B at higher concentrations has background fluorescence between 300 and 400 nm, the experiment was repeated using only buffer and subtracted from the measurement taken with HygX present. Change in fluorescence resulting from changing hygromycin B concentration was plotted against hygromycin B concentration and fit to a single binding-site model using Kaleidagraph Version 4.0.

Crystallization

Crystals were grown using the hanging-drop vapor diffusion method at room temperature in 3-µL drops containing an equal ratio of protein to reservoir solution. Crystals of EvdO1 (18 mg/mL in storage buffer plus 0.4 mM $NiCl_2$) appeared after 3 d with a reservoir solution of 100 mM sodium citrate tribasic (pH 5.1) and 13% (wt/wt) PEG8000. EvdO2 (6 mg/mL in storage buffer) crystallized in 100 mM imidazole (pH 8.0), 38% (wt/wt) PEG8000, and 250 mM NaCl. The EvdO2-AKG cocrystals used fully formed EvdO2 crystals soaked with freshly prepared 200 mM AKG in 100 mM imidazole (pH 8.0). AviO1 (16 mg/mL in storage buffer) crystallized in 100 mM CAPS (pH 10.5), 1.2 M $NaH_2PO_4$, 0.8 M $K_2HPO_4$, and 200 mM $Li_2SO_4$. HygX (16 mg/mL in storage buffer) crystallized from 100 mM Bis-Tris (pH 6.8), 100 mM MgCl2, and 12% (wt/wt) PEG8000. HygX-AKG crystals were grown by incubating HygX (16 mg/mL in storage buffer) with 3 mM AKG for 30 min before setting up drops; crystallization conditions consisted of 50 mM CsCl, 100 mM Mes (pH 6.5), and 30% (wt/wt) Jeffamine M-600. HygX-AKG-hygromycin B crystals were grown from HygX (16 mg/mL in storage buffer plus 1 mM $NiCl_2$, 3 mM AKG, and 5 mM hygromycin B) using a reservoir containing 100 mM Mes (pH 6.3) and 18% (wt/wt) PEG20000. HygX-Fe crystallized in 0.6 M succinic acid (pH 7). All crystals except those grown from Jeffamine M-600 were cryoprotected by creating an artificial mother liquor of the reservoir solution containing a cryoprotectant and soaking the crystals for one minute before cryocooling by plunging into liquid nitrogen. For EvdO1 and AviO1, the crystallization conditions were supplemented by 20% of a 50/50 (vol/vol) glycerol/ethylene glycol mix. For EvdO2 and HygX, the crystallization conditions were supplemented 17% (vol/vol) ethylene glycol.

Crystallographic Data Collection, Processing, Structure Determination, and Refinement Diffraction data were collected on the LS-CAT beamlines of the Advanced Photon Source (Argonne, Ill.) on Mar300 CCD detectors. All data were processed and scaled using the HKL2000 suite of programs. Structures of EvdO1, AviO1, and HygX were determined through single wavelength anomalous diffraction (SAD)-phasing from anomalous signal from bound nickel ions using data collected in wedges at 1.484 Å. This wavelength was experimentally determined using X-ray fluorescence scans around the Fe and Ni K-edges using an XFlash 1001 SD detector (Bruker-AXS). The HygX-Fe2+ dataset was collected at 1.739 Å, a wavelength identified through X-ray fluorescence scans as maximizing the anomalous signal from $Fe^{2+}$. Nickel-binding sites were determined using the program HKL2MAP and SHELXC/D/E and input into the AutoSol routine of PHENIX for phasing and density modification. EvdO2 was determined using molecular replacement with PHASER. To develop the search model for EvdO2, human phytanoyl-CoA dioxygenase phyhdl (PDB ID code 3OBZ) was structurally aligned with human phytanoyl-CoA 2 of 17 2-hydroxylase (PDB ID code 2A1X), and all nonconserved secondary structure, ligands and water molecules were removed. Costructures of EvdO2 with AKG and HygX with hygromycin B were determined by isomorphous replacement from the unliganded structure. All structures were improved using AutoBuild of PHENIX. Model building was performed in COOT with composite omit maps calculated in CNS. Refinement was performed using phenix.refine. The costructure of HygX-AKG-hygromycin B contains significant disorder at the N termini in two of the four protomers. Omit maps and additional refinement with strict restraints were used to minimize model bias during refinement of this structure. Importantly, clear electron density of a quality expected for a 1.6-Å resolution structure are observed for two chains and these were the chains used for computational docking controls and all figures.

Analogs Based on Modifications to DCE

The importance of the dichloroisoeverninic (DCE) acid moiety in the mechanism of action of the everninomicins was recently clarified via work from the Wilson group (*Proc. Natl. Acad. Sci. USA* 2016, 113:7527). The aromatic ring A1 forms a vital interaction with the ribosomal protein L16 via stacking with arginine residues. Mutations of the ribosome at this position result in complete everninomicin resistance (Aarestrup, et al., *Antimicrobial Agents and Chemotherapy* 2000, 44:3425; Zarazaga, et al. *Antimicrobial Agents and Chemotherapy* 2002, 46:3657; Adrian, et al., *Antimicrobial Agents and Chemotherapy* 2000, 44:732). In addition, mutations observed at this position are not associated with the resistance encoded by the rRNA methyltranferases present in the everninomicin biosynthetic gene cluster (Mosbacher, et al. *J. Mol. Biol.* 2003, 329:147; Weitnauer, et al. *Antimicrobial Agents and Chemotherapy* 2001, 45:690). Therefore, the vital interaction between the DCE ring and the L16 protein can provide an opportunity for directed everninomicin derivatization targeted to prevent the emergence of resistance. Due to the difficulty in synthetically obtaining everninomicin analogs, the bacterial machinery can be used to make novel everninomicin metabolites. This first requires a more detailed understanding of the biosynthesis of the DCE moiety. The four genes putatively associated with DCE biosynthesis include an acyltransferase (evdD1), an iterative type I polyketide synthase (evdD3), a flavin-dependent halogenase (evdD2), and an o-methyltransferase (evdM5). A functional analysis of the four DCE genes was accomplished by targeted gene replacement using the lambda-RED method combined with a microporous bacterial conjugation method. The genes of interest were replaced with an apramycin resistance cassette in the producer organism *Micromonaspora carbonacea* var. *aurantiaca*. Analysis of the mutant strain extracts provided us with a number of novel everninomicin metabolites, as well as a more complete understanding of eveminomicin biosynthesis.

Figures 21, 22A:
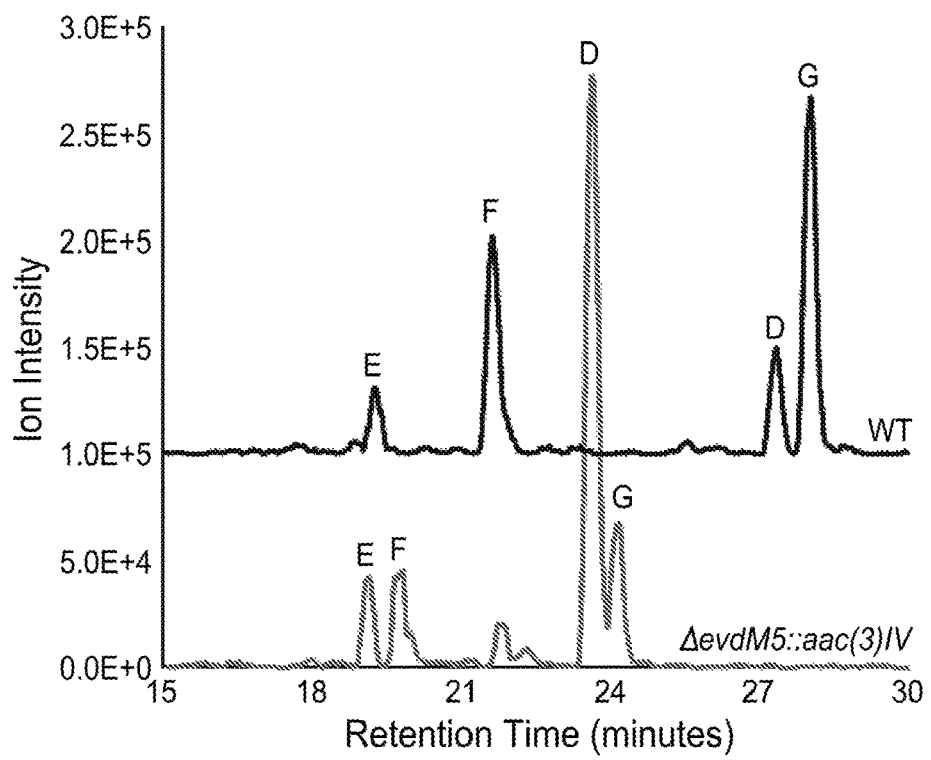
FIGS. 22A-22C show LC/MS chromatograms of wild type *M. carbonacea* var. *aurantiaca* and gene replacements of evdM5 (ΔevdM5::aac(3)IV).
Figure 22B:
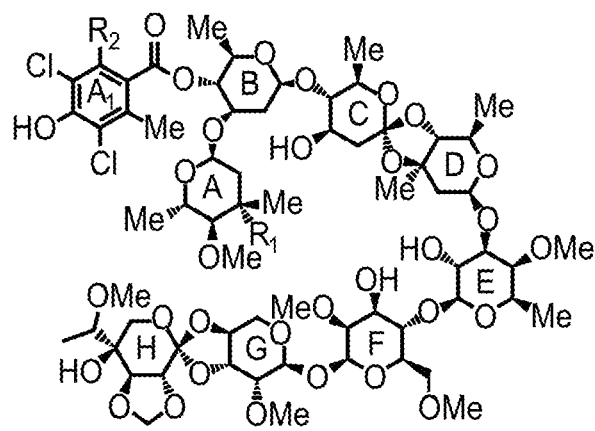
Figure 22C:
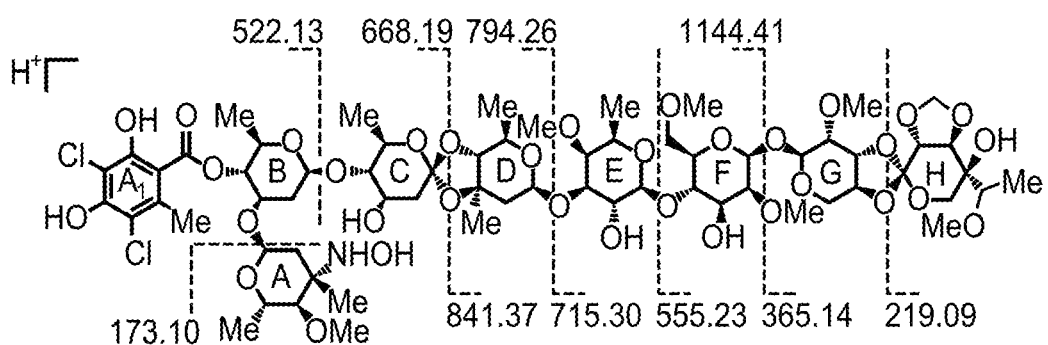

The extracts of the o-methyltransferase mutant strain ΔevdM5::aac(3)IV were evaluated by liquid chromatography-mass spectrometry (LC/MS). The mutant strain did not produce the wildtype eveminomicins D-G. However, the ΔevdM5::aac(3)IV extracts did produce four novel halogenated metabolites with exact masses 1521.5, 1491.5, 1507.5, and 1505.5. These masses differ by exactly 14.0 from the wildtype everninomicins (Ever D—1535.5; Ever E—1505.5; Ever F—1521.5; Ever G—1519.5), indicating the loss of a methyl group (FIG. 22A and FIG. 22B). In order to confirm that the genetic deletion resulted in the loss of the o-methyl group on the DCE, the metabolites were further evaluated by tandem LC/MS.9 Fragmentation (MS2) allowed for more detailed analysis of these novel metabolites to confirm the loss of the o-methyl group from the DCE ring (FIG. 22C). The remainder of the everninomicin structures were unchanged. Overall, four des-methyl everninomicin structures that differ only in the oxidation state of the amine group of the evernitrose sugar were identified. The loss of the o-methyl group is expected to increase the water solubility of the everninomicins, which may alter their in vivo pharmacokinetics (Weitnauer, et al. *Chem. Biol.* 2004, 11:1403).

Figure 23A:
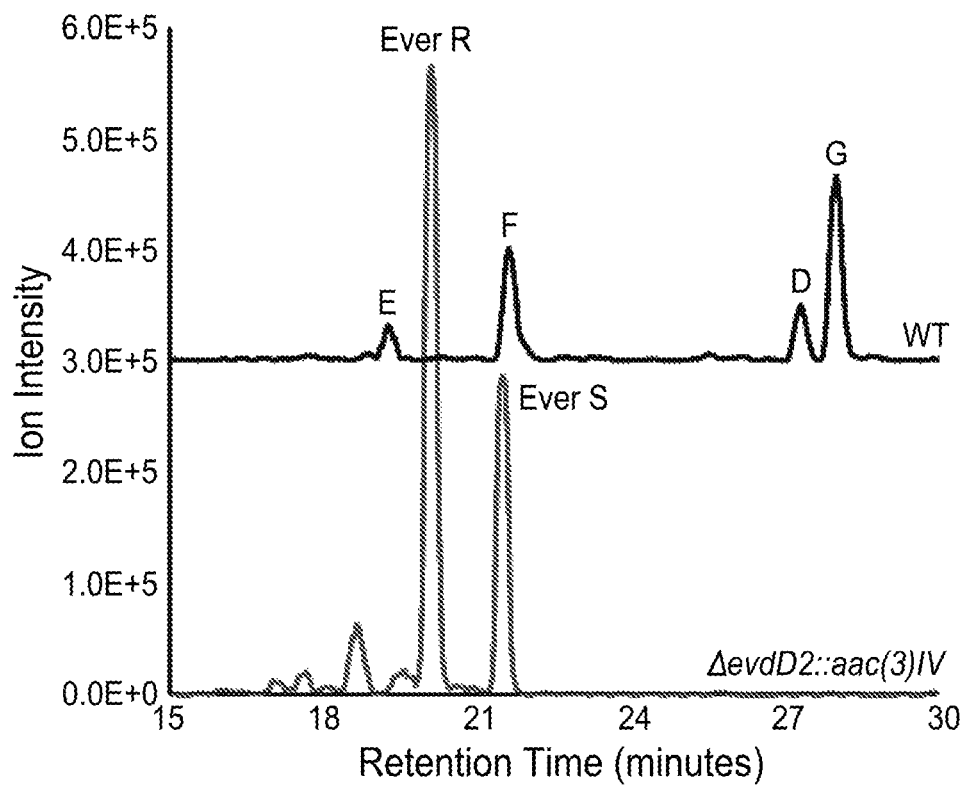
FIGS. 23A and 23B show LC/MS chromatograms of wild type *M. carbonacea* var. *aurantiaca* and gene replacements of evdD2 (ΔevdD2::aac(3)IV).
Figure 23B:
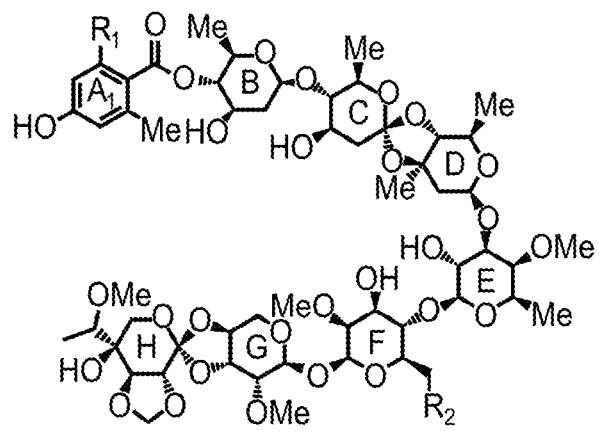

Next targeted genetic deletion of the putative flavin-dependent halogenase (evdD2) was analyzed. Given the results from the deletion of the o-methyltransferase, it was hypothesized that deletion of the halogenase would produce four everninomicin metabolites lacking the two chlorines from the DCE ring but otherwise retaining the octasaccharide backbone. As expected, LC/MS evaluation of the ΔevdD2::aac(3)IV extracts showed the complete loss of production of the wildtype everninomicins. However, the predicted metabolites were also not present. Instead two apparently non-halogenated metabolites with exact masses 1252.3 and 1266.3 were observed (FIGS. 23A and 23B). These metabolites were further evaluated via tandem LC/MS as previously described. This revealed that the metabolites were everninomicin-related molecules lacking the two chlorines and the methyl group on the DCE moiety. Additionally, the metabolites also appeared to lack the entire evernitrose sugar (ring A). The metabolites were designated as everninomicin R (mass 1252.3) and everninomicin S (mass 1266.3). The mass difference of 14.0 between Ever R and Ever S indicated the difference of a methyl group between the two metabolites. Fragmentation data showed that the additional methyl group is mostly likely located on the 2,6-di-O-methyl-d-mannose (ring F). Previous functional analysis and genetic homology comparison performed in our lab allowed for the assignment of all nine methyltransferases in the everninomicin biosynthetic pathway. A review of this work shows the gene encoding for the o-methyltransferase (evdM7) responsible for methylation at the C-6 hydroxyl of ring F is directly downstream of the deleted halogenase gene. It is therefore likely that the deletion of the halogenase resulted in the malfunction of o-methyltransferase evdM7 due to polar effects.

Figure 24A:
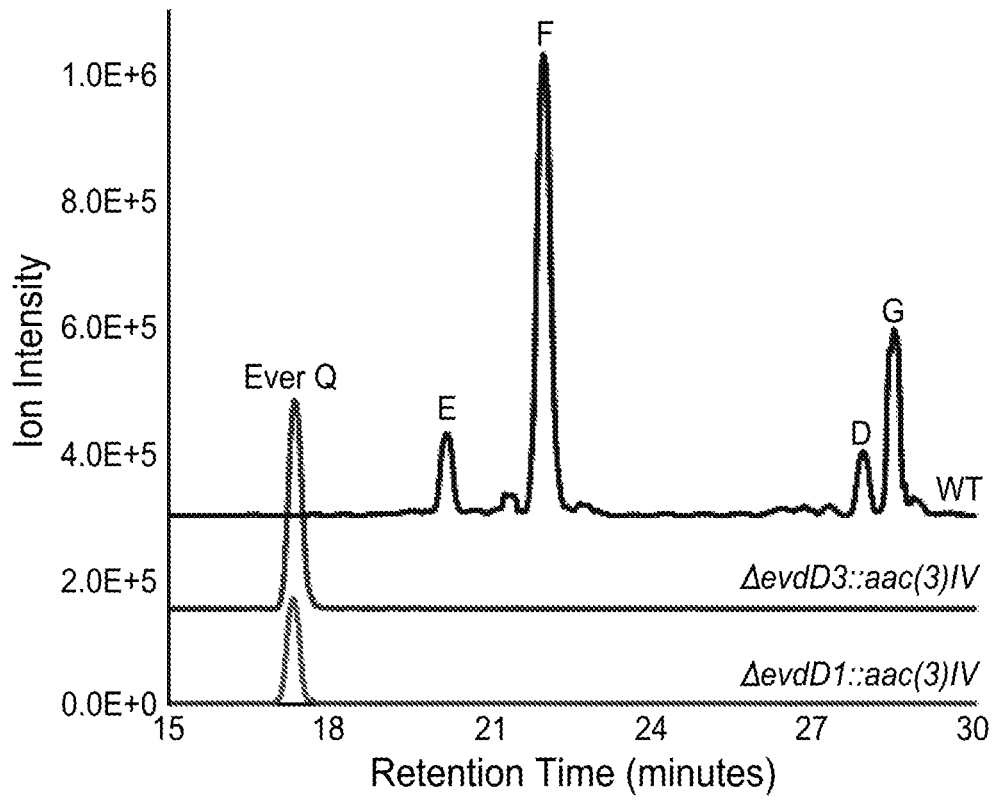
FIGS. 24A and 24B show LC/MS chromatograms of wild type *M. carbonacea* var. *aurantiaca* and gene replacements of evdD1 (ΔevdD1::aac(3)IV) and evdD3 (ΔevdD3::aac(3)
Figure 24B:
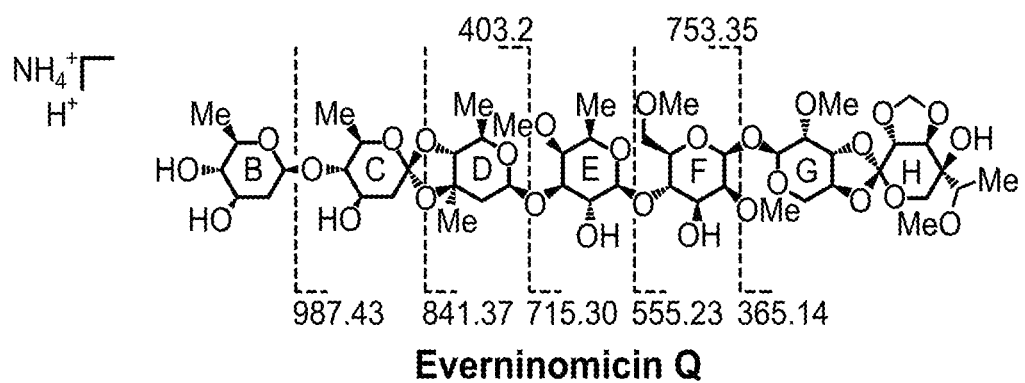

The putative acyltransferase (evdD1) and the iterative type I polyketide synthase (evdD3) were also deleted to confirm their role in the biosynthesis of DCE. It was expected that the deletion of either of these genes would provide eveminomicin analogs completely lacking the DCE ring. However, based on the results from the deletion of the flavin-dependent halogenase (evdD2), it was also hypothesized that any new metabolites may also lack the evernitrose sugar due to its apparent reliance on the presence of the DCE ring. Extracts from both mutant strains ΔevdD1::aac(3)IV and ΔevdD3::aac(3)IV showed a complete loss of production of the wildtype everninomicins. A single novel metabolite with an exact mass of 1116.4 was observed in the extracts of both mutant strains with the same elution time. The fragmentation pattern from tandem MS confirmed the metabolite to be an everninomicin shunt product lacking the dichloroisoeverninic acid (ring A1) and the evernitrose sugar (ring A). This metabolite was termed everninomicin Q (FIGS. 24A and 24B). The loss of evernitrose indicates that its attachment to d-olivose (ring B) by a glycosyltransferase is dependent on the presence of the fully elaborated DCE component.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A compound having the structure:

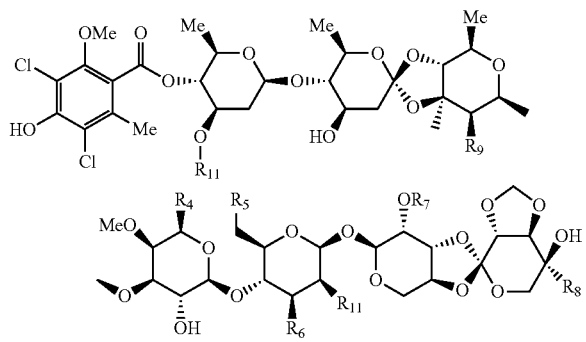

wherein $R_5$-$R_6$ are each, individually, H, OH, OCH$_3$, CH$_2$OH, CHO, CO$_2$H, CO$_2$R$_{12}$, C(O)R$_{12}$, or C$_1$-C$_6$ alkyl;

$R_7$ is H or CH$_3$;

$R_8$ is H, OCH$_3$, CH$_2$OH, CO$_2$H, CO$_2$R$_{12}$, C(O)R$_{12}$, or substituted C$_1$-C$_6$ alkyl that is substituted with alkyl, alkoxy, halide, or hydroxy;

$R_9$ is H, OH, OCH$_3$, or C$_1$-C$_6$ alkyl;

each $R_{11}$ is, independently, H, OCH$_3$, C$_1$-C$_6$ alkyl, or a 1-20 atom linker bound to rosaramicin; and $R_{12}$ is C$_1$-C$_6$ alkyl, or a pharmaceutically acceptable salt thereof, wherein the compound is not

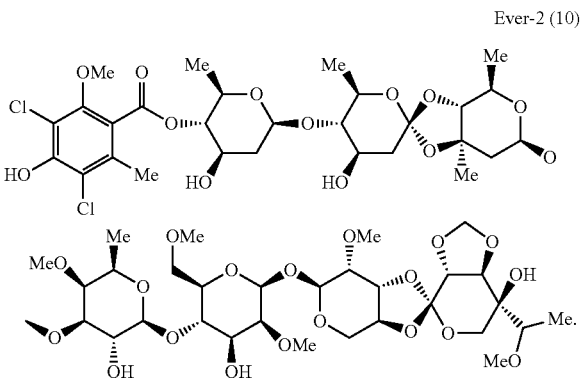

2. A method of treating infection comprising administering to a patient in need thereof a therapeutically effective amount of a compound of claim 1.

3. A compound of claim 1, wherein the compound has the structure:

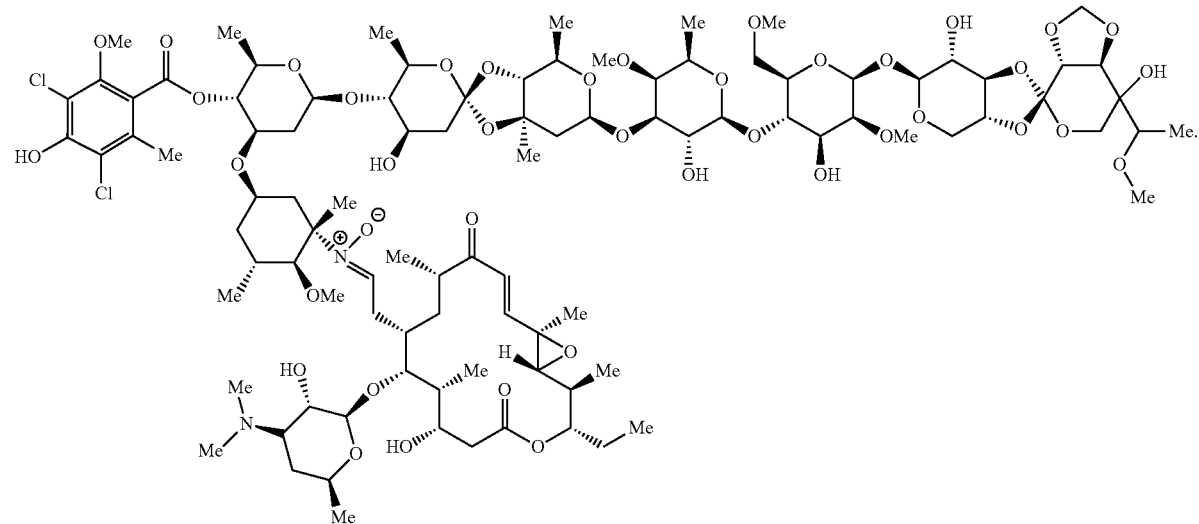

4. The method of claim 2, wherein the infection is a *S. aureus* infection.

* * * * *

```
                        SEQUENCE LISTING

<160> NUMBER OF SEQ ID NOS: 46

<210> SEQ ID NO 1
<211> LENGTH: 59
<212> TYPE: DNA
<213> ORGANISM: Artificial Sequence
<220> FEATURE:
<223> OTHER INFORMATION: synthetic construct

<400> SEQUENCE: 1
atggtcgacc tgctgaccgg cgtactcccg cagatccgga ttccggggat ccgtcgacc      59

<210> SEQ ID NO 2
<211> LENGTH: 58
<212> TYPE: DNA
<213> ORGANISM: Artificial Sequence
<220> FEATURE:
<223> OTHER INFORMATION: synthetic construct

<400> SEQUENCE: 2
attccggcag gtagtcccac actcggatgg tcatgttcat gtaggctgga gctgcttc       58

<210> SEQ ID NO 3
<211> LENGTH: 59
<212> TYPE: DNA
<213> ORGANISM: Artificial Sequence
<220> FEATURE:
<223> OTHER INFORMATION: synthetic construct

<400> SEQUENCE: 3
gacaccgccg gtccaccgtg ggcaggagcc ccggcggtga ttccggggat ccgtcgacc      59

<210> SEQ ID NO 4
<211> LENGTH: 58
<212> TYPE: DNA
<213> ORGANISM: Artificial Sequence
<220> FEATURE:
<223> OTHER INFORMATION: synthetic construct

<400> SEQUENCE: 4
ccacgctctc gtcatacgct gatgcggtcc gactcacgtt gtaggctgga gctgcttc      58

<210> SEQ ID NO 5
<211> LENGTH: 59
<212> TYPE: DNA
<213> ORGANISM: Artificial Sequence
<220> FEATURE:
<223> OTHER INFORMATION: synthetic construct

<400> SEQUENCE: 5
cgcccggaaa ccccacacga aggagaccgc tacgtgagta ttccggggat ccgtcgacc      59

<210> SEQ ID NO 6
<211> LENGTH: 58
<212> TYPE: DNA
<213> ORGANISM: Artificial Sequence
<220> FEATURE:
<223> OTHER INFORMATION: synthetic construct
```

<400> SEQUENCE: 6
ccgccgcggc gagcagccgc tggacgagcg agccggtcat gtaggctgga gctgcttc    58

<210> SEQ ID NO 7
<211> LENGTH: 20
<212> TYPE: DNA
<213> ORGANISM: Artificial Sequence
<220> FEATURE:
<223> OTHER INFORMATION: synthetic construct

<400> SEQUENCE: 7
cgttcgggta gtcgtagacc    20

<210> SEQ ID NO 8
<211> LENGTH: 20
<212> TYPE: DNA
<213> ORGANISM: Artificial Sequence
<220> FEATURE:
<223> OTHER INFORMATION: synthetic construct

<400> SEQUENCE: 8
actagggttt cccccacaac    20

<210> SEQ ID NO 9
<211> LENGTH: 20
<212> TYPE: DNA
<213> ORGANISM: Artificial Sequence
<220> FEATURE:
<223> OTHER INFORMATION: synthetic construct

<400> SEQUENCE: 9
tacgcgcact tcatcgatct    20

<210> SEQ ID NO 10
<211> LENGTH: 20
<212> TYPE: DNA
<213> ORGANISM: Artificial Sequence
<220> FEATURE:
<223> OTHER INFORMATION: synthetic construct

<400> SEQUENCE: 10
gatacgtgtc cagggagctg    20

<210> SEQ ID NO 11
<211> LENGTH: 20
<212> TYPE: DNA
<213> ORGANISM: Artificial Sequence
<220> FEATURE:
<223> OTHER INFORMATION: synthetic construct

<400> SEQUENCE: 11
acgacgagca cttcttcctg    20

<210> SEQ ID NO 12
<211> LENGTH: 20
<212> TYPE: DNA
<213> ORGANISM: Artificial Sequence
<220> FEATURE:
<223> OTHER INFORMATION: synthetic construct

<400> SEQUENCE: 12
gaagaccgag tccaggtacg    20

<210> SEQ ID NO 13

```
<211> LENGTH: 20
<212> TYPE: DNA
<213> ORGANISM: Artificial Sequence
<220> FEATURE:
<223> OTHER INFORMATION: synthetic construct

<400> SEQUENCE: 13
accgactgga ccttccttct                                               20

<210> SEQ ID NO 14
<211> LENGTH: 20
<212> TYPE: DNA
<213> ORGANISM: Artificial Sequence
<220> FEATURE:
<223> OTHER INFORMATION: synthetic construct

<400> SEQUENCE: 14
tcgctataat gaccccgaag                                               20

<210> SEQ ID NO 15
<211> LENGTH: 24
<212> TYPE: DNA
<213> ORGANISM: Artificial Sequence
<220> FEATURE:
<223> OTHER INFORMATION: synthetic construct

<400> SEQUENCE: 15
catatggtga tcggcttgct gggc                                          24

<210> SEQ ID NO 16
<211> LENGTH: 26
<212> TYPE: DNA
<213> ORGANISM: Artificial Sequence
<220> FEATURE:
<223> OTHER INFORMATION: synthetic construct

<400> SEQUENCE: 16
agtactgtag cggtctcctt cgtgtg                                        26

<210> SEQ ID NO 17
<211> LENGTH: 27
<212> TYPE: DNA
<213> ORGANISM: Artificial Sequence
<220> FEATURE:
<223> OTHER INFORMATION: synthetic construct

<400> SEQUENCE: 17
catatgagcg aattcatggt cgacctg                                       27

<210> SEQ ID NO 18
<211> LENGTH: 26
<212> TYPE: DNA
<213> ORGANISM: Artificial Sequence
<220> FEATURE:
<223> OTHER INFORMATION: synthetic construct

<400> SEQUENCE: 18
gatatccact cggatggtca tgttca                                        26

<210> SEQ ID NO 19
<211> LENGTH: 24
<212> TYPE: DNA
<213> ORGANISM: Artificial Sequence
<220> FEATURE:
<223> OTHER INFORMATION: synthetic construct

<400> SEQUENCE: 19
```
catatggtga gtcggaccgc atca                                              24

<210> SEQ ID NO 20
<211> LENGTH: 24
<212> TYPE: DNA
<213> ORGANISM: Artificial Sequence
<220> FEATURE:
<223> OTHER INFORMATION: synthetic construct

<400> SEQUENCE: 20
gatatctcac gaccccaccc gcga                                              24

<210> SEQ ID NO 21
<211> LENGTH: 20
<212> TYPE: DNA
<213> ORGANISM: Artificial Sequence
<220> FEATURE:
<223> OTHER INFORMATION: synthetic construct

<400> SEQUENCE: 21
gattcggatg attcctacgc                                                   20

<210> SEQ ID NO 22
<211> LENGTH: 20
<212> TYPE: DNA
<213> ORGANISM: Artificial Sequence
<220> FEATURE:
<223> OTHER INFORMATION: synthetic construct

<400> SEQUENCE: 22
gaaggcgttg agatgcagtt                                                   20

<210> SEQ ID NO 23
<211> LENGTH: 20
<212> TYPE: DNA
<213> ORGANISM: Artificial Sequence
<220> FEATURE:
<223> OTHER INFORMATION: synthetic construct

<400> SEQUENCE: 23
attccgggga tccgtcgacc                                                   20

<210> SEQ ID NO 24
<211> LENGTH: 19
<212> TYPE: DNA
<213> ORGANISM: Artificial Sequence
<220> FEATURE:
<223> OTHER INFORMATION: synthetic construct

<400> SEQUENCE: 24
tgtaggctgg agctgcttc                                                    19

<210> SEQ ID NO 25
<211> LENGTH: 20
<212> TYPE: DNA
<213> ORGANISM: Artificial Sequence
<220> FEATURE:
<223> OTHER INFORMATION: synthetic construct

<400> SEQUENCE: 25
tgaatgaact gcaggacgag                                                   20

<210> SEQ ID NO 26
<211> LENGTH: 18
<212> TYPE: DNA

<213> ORGANISM: Artificial Sequence
<220> FEATURE:
<223> OTHER INFORMATION: synthetic construct

<400> SEQUENCE: 26
aatatcacgg gtagccaa                                              18

<210> SEQ ID NO 27
<211> LENGTH: 59
<212> TYPE: DNA
<213> ORGANISM: Artificial Sequence
<220> FEATURE:
<223> OTHER INFORMATION: synthetic construct

<400> SEQUENCE: 27
cgggcccgcg accgctgatc agaagggtgt ggactgatga ttccggggat ccgtcgacc    59

<210> SEQ ID NO 28
<211> LENGTH: 58
<212> TYPE: DNA
<213> ORGANISM: Artificial Sequence
<220> FEATURE:
<223> OTHER INFORMATION: synthetic construct

<400> SEQUENCE: 28
ctgtcgcccg gaacgctcat cggatgcccc ccgagctcat gtaggctgga gctgcttc     58

<210> SEQ ID NO 29
<211> LENGTH: 59
<212> TYPE: DNA
<213> ORGANISM: Artificial Sequence
<220> FEATURE:
<223> OTHER INFORMATION: synthetic construct

<400> SEQUENCE: 29
tcgtgactgt cgaggtcatc ccttgaagga gacggcatga ttccggggat ccgtcgacc    59

<210> SEQ ID NO 30
<211> LENGTH: 58
<212> TYPE: DNA
<213> ORGANISM: Artificial Sequence
<220> FEATURE:
<223> OTHER INFORMATION: synthetic construct

<400> SEQUENCE: 30
tggccttctt cgggtagggg ggcgtggtcg gccggctat gtaggctgga gctgcttc      58

<210> SEQ ID NO 31
<211> LENGTH: 59
<212> TYPE: DNA
<213> ORGANISM: Artificial Sequence
<220> FEATURE:
<223> OTHER INFORMATION: synthetic construct

<400> SEQUENCE: 31
tttcccgcgc gcacccgaac actaggcttg gaatccatga ttccggggat ccgtcgacc    59

<210> SEQ ID NO 32
<211> LENGTH: 58
<212> TYPE: DNA
<213> ORGANISM: Artificial Sequence
<220> FEATURE:
<223> OTHER INFORMATION: synthetic construct

<400> SEQUENCE: 32
gtggggtcgc cgcaggcggc atccgcgtcc ggccggtcat gtaggctgga gctgcttc     58

```
<210> SEQ ID NO 33
<211> LENGTH: 20
<212> TYPE: DNA
<213> ORGANISM: Artificial Sequence
<220> FEATURE:
<223> OTHER INFORMATION: synthetic construct

<400> SEQUENCE: 33
attccgggga tccgtcgacc                                               20

<210> SEQ ID NO 34
<211> LENGTH: 19
<212> TYPE: DNA
<213> ORGANISM: Artificial Sequence
<220> FEATURE:
<223> OTHER INFORMATION: synthetic construct

<400> SEQUENCE: 34
tgtaggctgg agctgcttc                                                19

<210> SEQ ID NO 35
<211> LENGTH: 20
<212> TYPE: DNA
<213> ORGANISM: Artificial Sequence
<220> FEATURE:
<223> OTHER INFORMATION: synthetic construct

<400> SEQUENCE: 35
tgaatgaact gcaggacgag                                               20

<210> SEQ ID NO 36
<211> LENGTH: 18
<212> TYPE: DNA
<213> ORGANISM: Artificial Sequence
<220> FEATURE:
<223> OTHER INFORMATION: synthetic construct

<400> SEQUENCE: 36
aatatcacgg gtagccaa                                                 18

<210> SEQ ID NO 37
<211> LENGTH: 20
<212> TYPE: DNA
<213> ORGANISM: Artificial Sequence
<220> FEATURE:
<223> OTHER INFORMATION: synthetic construct

<400> SEQUENCE: 37
tcagtccaca cccttctgat                                               20

<210> SEQ ID NO 38
<211> LENGTH: 20
<212> TYPE: DNA
<213> ORGANISM: Artificial Sequence
<220> FEATURE:
<223> OTHER INFORMATION: synthetic construct

<400> SEQUENCE: 38
ggcctgtacc tgatgacgag                                               20

<210> SEQ ID NO 39
<211> LENGTH: 20
<212> TYPE: DNA
<213> ORGANISM: Artificial Sequence
<220> FEATURE:
```

<223> OTHER INFORMATION: synthetic construct

<400> SEQUENCE: 39
tgctgcactg tcgttcctac                                           20

<210> SEQ ID NO 40
<211> LENGTH: 20
<212> TYPE: DNA
<213> ORGANISM: Artificial Sequence
<220> FEATURE:
<223> OTHER INFORMATION: synthetic construct

<400> SEQUENCE: 40
ataccagcgc tttcacgagt                                           20

<210> SEQ ID NO 41
<211> LENGTH: 20
<212> TYPE: DNA
<213> ORGANISM: Artificial Sequence
<220> FEATURE:
<223> OTHER INFORMATION: synthetic construct

<400> SEQUENCE: 41
gtatggctca ctgcctggtc                                           20

<210> SEQ ID NO 42
<211> LENGTH: 18
<212> TYPE: DNA
<213> ORGANISM: Artificial Sequence
<220> FEATURE:
<223> OTHER INFORMATION: synthetic construct

<400> SEQUENCE: 42
ggtgcacgat cggatgat                                             18

<210> SEQ ID NO 43
<211> LENGTH: 20
<212> TYPE: DNA
<213> ORGANISM: Artificial Sequence
<220> FEATURE:
<223> OTHER INFORMATION: synthetic construct

<400> SEQUENCE: 43
accgactgga ccttccttct                                           20

<210> SEQ ID NO 44
<211> LENGTH: 20
<212> TYPE: DNA
<213> ORGANISM: Artificial Sequence
<220> FEATURE:
<223> OTHER INFORMATION: synthetic construct

<400> SEQUENCE: 44
tcgctataat gacccccgaag                                          20

<210> SEQ ID NO 45
<211> LENGTH: 26
<212> TYPE: DNA
<213> ORGANISM: Artificial Sequence
<220> FEATURE:
<223> OTHER INFORMATION: synthetic construct

<400> SEQUENCE: 45
catatgatgg accgtaggga gattca                                    26

```
<210> SEQ ID NO 46
<211> LENGTH: 23
<212> TYPE: DNA
<213> ORGANISM: Artificial Sequence
<220> FEATURE:
<223> OTHER INFORMATION: synthetic construct

<400> SEQUENCE: 46
gatatctcag gacgggaggc tcg                                              23
```

UNITED STATES PATENT AND TRADEMARK OFFICE
CERTIFICATE OF CORRECTION

PATENT NO. : 10,696,996 B2
APPLICATION NO. : 16/060467
DATED : June 30, 2020
INVENTOR(S) : Brian O. Bachmann, Emilianne M. Limbrick and Kasia Derewacz It is certified that error appears in the above-identified patent and that said Letters Patent is hereby corrected as shown below:

On the Title Page

Item (73), the assignee "Vanderbilt Univeristy" should read --Vanderbilt University--.

Signed and Sealed this
Sixth Day of October, 2020

Andrei Iancu
*Director of the United States Patent and Trademark Office*